(12) United States Patent
Musini et al.

(10) Patent No.: US 11,351,093 B2
(45) Date of Patent: Jun. 7, 2022

(54) HEALTHCARE MANAGEMENT SERVICES

(71) Applicant: Stanley Black & Decker, Inc., New Britain, CT (US)

(72) Inventors: Emanuele Musini, Boston, MA (US); Aiden Y. Feng, Somerville, MA (US); James Malcolm Andrew Wyman, Boston, MA (US); Emanuele Baglini, Chiavari (IT); Antonello Scalmato, Genoa (IT); Paolo Vernazza, Chiavari (IT); Simone Denei, Genoa (IT); Andrea Dulach, Rome (IT); Alfonso Desiderio, Cogoleto (IT); Luca Petacchi, Ortonovo (IT)

(73) Assignee: Stanley Black & Decker, Inc., New Britain, CT (US)

( * ) Notice: Subject to any disclaimer, the term of this patent is extended or adjusted under 35 U.S.C. 154(b) by 0 days.

(21) Appl. No.: 16/722,990

(22) Filed: Dec. 20, 2019

(65) Prior Publication Data

US 2020/0222284 A1 Jul. 16, 2020

Related U.S. Application Data

(63) Continuation of application No. 15/620,546, filed on Jun. 12, 2017, now Pat. No. 10,555,874.
(Continued)

(51) Int. Cl.
*A61J 7/04* (2006.01)
*G06F 3/01* (2006.01)
(Continued)

(52) U.S. Cl.
CPC ........... *A61J 7/0427* (2015.05); *A61J 7/0084* (2013.01); *A61J 7/0418* (2015.05); *A61J 7/0454* (2015.05);
(Continued)

(58) Field of Classification Search
CPC ...... A61J 7/0427; A61J 7/0418; A61J 7/0454; A61J 7/0463; A61J 7/0084; A61J 7/0481; A61J 2200/30; G06F 3/01; G16H 20/13; G16H 50/20; G16H 40/63; G16H 40/67; G07F 11/52
See application file for complete search history.

(56) References Cited

U.S. PATENT DOCUMENTS 4,573,606 A * 3/1986 Lewis .................. A61J 7/0481
221/15
5,582,323 A * 12/1996 Kurtenbach .......... A61J 7/0481
221/2
(Continued)

FOREIGN PATENT DOCUMENTS

EP        3 469 503 A2     4/2019
WO   WO 2017/218425 A2   12/2017

OTHER PUBLICATIONS

Invitation to Pay Additional Fees dated Nov. 14, 2017 in connection with International Application No. PCT/US2017/037048.
(Continued)

*Primary Examiner* — Michael Collins
(74) *Attorney, Agent, or Firm* — Wolf, Greenfield & Sacks, P.C.

(57) ABSTRACT

Systems, methods, and computer-readable media for a healthcare management service are provided.

19 Claims, 54 Drawing Sheets

Related U.S. Application Data

(60) Provisional application No. 62/464,598, filed on Feb. 28, 2017, provisional application No. 62/349,257, filed on Jun. 13, 2016.

(51) Int. Cl.

| | | |
|---|---|---|
| *G16H 20/13* | (2018.01) | |
| *G16H 50/20* | (2018.01) | |
| *G16H 40/63* | (2018.01) | |
| *A61J 7/00* | (2006.01) | |
| *G07F 11/52* | (2006.01) | |
| *G16H 40/67* | (2018.01) | |

(52) U.S. Cl.
CPC .......... *A61J 7/0463* (2015.05); *A61J 7/0481* (2013.01); *G06F 3/01* (2013.01); *G07F 11/52* (2013.01); *G16H 20/13* (2018.01); *G16H 40/63* (2018.01); *G16H 40/67* (2018.01); *G16H 50/20* (2018.01); *A61J 2200/30* (2013.01)

(56) References Cited

U.S. PATENT DOCUMENTS

| | | | |
|---|---|---|---|
| 5,915,589 A | 6/1999 | Lim | |
| 6,510,962 B1* | 1/2003 | Lim | A61J 7/0481 221/15 |
| 6,702,146 B2 | 3/2004 | Varis | |
| 6,732,884 B2* | 5/2004 | Topliffe | G07F 11/54 221/3 |
| 7,002,476 B2 | 2/2006 | Rapchak | |
| 7,048,141 B2 | 5/2006 | Abdulhay et al. | |
| 7,213,721 B2 | 5/2007 | Abdulhay et al. | |
| 7,295,890 B2 | 11/2007 | Jean-Pierrre | |
| 7,711,449 B2 | 5/2010 | Abdulhay et al. | |
| 7,844,361 B2 | 11/2010 | Jean-Pierre | |
| 8,032,397 B2* | 10/2011 | Lawless | G16H 10/60 705/3 |
| 8,068,934 B2 | 11/2011 | Saltsov | |
| 8,108,068 B1* | 1/2012 | Boucher | G01G 17/00 700/236 |
| 8,874,260 B2* | 10/2014 | Saltsov | A61J 7/0076 700/244 |
| 9,218,458 B2 | 12/2015 | Baarman et al. | |
| 9,439,835 B2 | 9/2016 | DiMartino et al. | |
| 9,579,264 B1 | 2/2017 | Litton | |
| 9,603,776 B2 | 3/2017 | Bunker et al. | |
| 9,731,853 B2 | 8/2017 | Akdogan et al. | |
| 9,836,583 B2* | 12/2017 | Garcia | A61J 7/0481 |
| 10,073,954 B2* | 9/2018 | Chen | A61J 7/0418 |
| 10,106,283 B2 | 10/2018 | Akdogan et al. | |
| 10,555,874 B2 | 2/2020 | Feng et al. | |
| 10,780,023 B2 | 9/2020 | Musini et al. | |
| 2003/0023146 A1 | 1/2003 | Shusterman | |
| 2003/0024943 A1* | 2/2003 | MacDonald | A61J 7/0084 221/92 |
| 2004/0172163 A1 | 9/2004 | Varis | |
| 2005/0087255 A1* | 4/2005 | Humphrey | B67D 1/1236 141/94 |
| 2006/0180600 A1 | 8/2006 | Talyor | |
| 2007/0093935 A1 | 4/2007 | Fu | |
| 2008/0119958 A1 | 5/2008 | Bear et al. | |
| 2008/0283542 A1 | 11/2008 | Lanka et al. | |
| 2010/0030374 A1 | 2/2010 | Saltsov | |
| 2012/0006847 A1 | 1/2012 | Coe | |
| 2013/0151274 A1 | 6/2013 | Bage et al. | |
| 2013/0197693 A1* | 8/2013 | Kamen | G16H 20/17 700/244 |
| 2014/0025199 A1* | 1/2014 | Berg | A61J 7/0084 700/232 |
| 2014/0058560 A1 | 2/2014 | Kanagala | |
| 2014/0131378 A1 | 5/2014 | Shih et al. | |
| 2014/0243749 A1 | 8/2014 | Edwards et al. | |
| 2014/0277702 A1 | 9/2014 | Shaw | |
| 2014/0277707 A1* | 9/2014 | Akdogan | G07C 9/32 700/237 |
| 2014/0277710 A1* | 9/2014 | Akdogan | A61J 1/03 700/241 |
| 2014/0278508 A1* | 9/2014 | Akdogan | H04N 7/188 705/2 |
| 2014/0358278 A1* | 12/2014 | Zhang | G16H 20/13 700/240 |
| 2015/0278475 A1 | 10/2015 | Shor | |
| 2016/0042151 A1 | 2/2016 | Akdogan et al. | |
| 2016/0081883 A1 | 3/2016 | Saltsov | |
| 2016/0132660 A1 | 5/2016 | Barajas et al. | |
| 2016/0151246 A1* | 6/2016 | Sotelo | A61J 7/04 221/1 |
| 2016/0158107 A1 | 6/2016 | Dvorak et al. | |
| 2016/0220180 A1* | 8/2016 | Fateh | A61B 5/4833 |
| 2016/0228333 A1* | 8/2016 | Bukstein | G01P 15/00 |
| 2016/0376140 A1* | 12/2016 | Tansey, Jr. | A47J 31/44 700/236 |
| 2017/0043896 A1 | 2/2017 | Fernandez | |
| 2017/0058846 A1 | 3/2017 | Heaps et al. | |
| 2017/0083687 A1 | 3/2017 | Josyula et al. | |
| 2017/0172850 A1 | 6/2017 | Cahan et al. | |
| 2017/0228520 A1 | 8/2017 | Kidd et al. | |
| 2017/0354574 A1 | 12/2017 | Feng et al. | |
| 2019/0133888 A1 | 5/2019 | Lam | |
| 2019/0282450 A1* | 9/2019 | Lam | A61J 7/0427 |
| 2020/0230027 A1 | 7/2020 | Musini et al. | |

OTHER PUBLICATIONS

International Search Report and Written Opinion dated Feb. 23, 2018 in connection with International Application No. PCT/US2017/037048.

International Preliminary Report on Patentability dated Dec. 27, 2018 in connection with International Application No. PCT/US2017/037048.

Ulanoff, Hands on with Hero, the pill-dispensing robot. Mar. 8, 2016; 12 pages. Retrieved from the Internet, http://mashable.com/2016/03/08/hero-pill-dispensing-robot-hands-on/#tIHBS4aiuqS.

International Search Report and Written Opinion dated Jan. 21, 2020 in connection with International Application No. PCT/US2019/058520.

International Preliminary Report on Patentability dated May 14, 2021 in connection with International Application No. PCT/US2019/058520.

U.S. Appl. No. 17/289,663, filed Apr. 28, 2021, Feng et al.

PCT/US2019/058520, May 14, 2021, International Preliminary Report on Patentability.

\* cited by examiner

HEALTHCARE MANAGEMENT SERVICES

CROSS-REFERENCE TO RELATED APPLICATIONS

This Application is a Continuation of and claims priority under 35 U.S.C. § 120 of U.S. application Ser. No. 15/620,546, filed Jun. 12, 2017, and entitled "HEALTHCARE MANAGEMENT SERVICES", which claims the benefit under 35 U.S.C. § 119 to U.S. Provisional Application Ser. No. 62/464,598, filed Feb. 28, 2017, and entitled "HEALTHCARE MANAGEMENT SERVICES," and U.S. Provisional Application Ser. No. 62/349,257, filed Jun. 12, 2016, and entitled "HEALTHCARE MANAGEMENT SERVICES," each of which is incorporated herein by reference in its entirety.

TECHNICAL FIELD

This disclosure relates to healthcare management services with robotic devices and, more particularly, to healthcare management services with artificially intelligent robotic companion devices that help users manage their healthcare needs, for example, by engaging users in a social manner through voice interaction to provide healthcare-focused content and services.

BACKGROUND OF THE DISCLOSURE

Conventional medication adherence systems fail to provide secure authentication of appropriate end users, to notify relevant caretakers of successful or unsuccessful adherence by end users, and/or to dispense of medication while also addressing the social and/or emotional needs of end users.

SUMMARY OF THE DISCLOSURE

This document describes systems, methods, and computer-readable media for a healthcare management service.

For example, a robotic interface system is provided that may include a communications component, at least one sensor, at least one input/output (I/O) component, a processor in operative communication with the communications component, the at least one sensor, and the at least one I/O component, and a main body including an inlet port, an outlet port, a container assembly including a plurality of compartments, and a motor coupled to the container assembly and operative to rotate the container assembly about an axis within the main body to align any one of the plurality of compartments with either the inlet port or the outlet port, wherein the processor is operative to communicate with a user via the at least one I/O component during an assisted pill insertion procedure in which at least one pill is inserted into at least one of the plurality of compartments via the inlet port and communicate with the user via the at least one I/O component during a pill dispersal procedure in which at least one pill is dispersed out of one of the plurality of compartments via the outlet port.

As another example, a robotic interface system is provided that may include a main body including an inlet port, an outlet port, a container assembly including a plurality of compartments, and a motor coupled to the container assembly and operative to rotate the container assembly about a rotation axis within the main body to align any one of the plurality of compartments with either the inlet port or the outlet port, a stand that supports the main body and that is constructed to hold a receptacle under the outlet port, and a processor that is operative to control rotation of the motor to align a selected one of the plurality of compartments with the inlet port or the outlet port in accordance with a pill insertion procedure or a pill dispersal procedure.

As yet another example, a robotic interface system is provided that may include a main body including an inlet port, an outlet port, a container assembly including a container member including a plurality of compartments, and a ring member including a pill window, a first motor operative to selectively couple or decouple the ring member to the container member, a second motor coupled to the container member and operative to rotate both the container member and the ring member in concert with each other about a rotation axis within the main body to align the pill window with the inlet port, the outlet port, or any location between the inlet and outlet ports when the container member is coupled to the ring member, and rotate the container member independently of the ring member about the rotation axis within the main body to align any one of the plurality of compartments with the pill window when the container member is decoupled from the ring member, a stand that supports the main body and that is constructed to hold a receptacle under the outlet port, and a processor that is operative to control operation of the first and second motors in accordance with a pill insertion procedure or a pill dispersal procedure.

As yet another example, a method for loading pills with assistance of a robotic interface system including a container assembly is provided, where the method may include determining whether a user desires to manually load the container assembly or requires assisted loading of the container assembly, in response to determining that the user desires to manually load the container assembly, instructing the user to remove the container assembly from the robotic interface system, displaying manual insertion instructions on the robotic interface system that provide step-by-step instructions for populating a plurality of compartments of the container assembly according to a pill schedule, detecting whether the container assembly has been inserted into the robotic interface system, and verifying that the container assembly has been filled according to the pill schedule, and, in response to determining that the user requires assisted loading of the container assembly, displaying assisted loading instructions on the robotic interface system that specify which pill to insert into an inlet port of the robotic interface system, verifying that a pill is received into one of the plurality of compartments, and repeating the displaying of assisted loading instructions and the verifying until it is determined that the plurality of compartments are filled according to the pill schedule.

As yet another example, a method for dispensing pills with assistance of a robotic interface system including a container assembly and receptacle region is provided, where the method may include verifying an identity of a user before commencing a pill dispensing procedure, determining whether the pill dispensing procedure is for pills contained inside the container assembly or outside the container assembly, in response to determining that the pill dispensing procedure is for pills contained inside the container assembly, displaying a list of pills to be dispensed according to a pill schedule for the verified user, and dispensing each pill in the displayed list of pills out of the container assembly into the receptacle.

As yet another example, a method for dispensing pills with assistance of a robotic interface system including a container assembly is provided, where the method may include receiving a wake signal, activating the robotic interface system in response to the received wake signal, determining whether an identity of a user is verified, in response to determining that the user is not verified, transmitting mobile reminders to the user if a time duration past a scheduled dose time is less than a fixed period of time, and marking the scheduled dose as missed if the time duration past the scheduled dose time is equal to or greater than the fixed period of time.

As yet another example, a method for managing missed dosages with assistance of a robotic interface system is provided, where the method may include receiving a wake signal, activating the robotic interface system in response to the received wake signal, determining that a scheduled dose time has been missed, receiving a user interaction with the robotic interface system after it has been determined that the scheduled dose time has been missed, displaying a first set of user selectable options when the user interaction is received during a same day as the scheduled dose time, and displaying a second set of user selectable options when the user interaction is received at a day subsequent to the scheduled dose time.

As yet another example, a method for rescheduling admission of dosages with assistance of a robotic interface system is provided, where the method may include receiving a wake signal with a pill schedule, activating the robotic interface system in response to the received wake signal, receiving an indication from a user that a dosage requires rescheduling, receiving a user specified rescheduling of a time to take the dosage, and updating the pill schedule based on the user specified rescheduling of a time to take the dosage.

As yet another example, a system is provided that may include a plurality of robotic interface (RI) subsystems, a plurality of user caretaker (UC) subsystems, and a healthcare management service (HMS) subsystem operative to communicate with the plurality of RI subsystems and the plurality of UC subsystems to facilitate and supervise a user's medication adherence.

This Summary is provided merely to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters may refer to like parts throughout, and in which.

DETAILED DESCRIPTION OF THE DISCLOSURE

Systems, methods, and computer-readable media for a healthcare management service are provided. Hardware and software system elements may be combined for providing a robotic interface subsystem (e.g., an artificially intelligent robotic companion device) that may function as a healthcare companion for an end user of a healthcare management service platform. The robotic interface subsystem may be operative to interact with end users via voice to assist with their healthcare needs and answer healthcare questions for educational purposes. The robotic interface subsystem may be configured with the capability to store medications and dispense medications according to a schedule associated with an end user. At the specified times of the schedule for the user's medication doses, the robotic interface subsystem may issue voice reminders and confirm the user's identity and presence using facial recognition and/or any other suitable biometric sensors (e.g., voice recognition and/or a fingerprint sensor and/or a password entry mechanism). If a medication dose is missed, the robotic interface subsystem may be operative to alert a personal electronic device of the end user and/or of a user caretaker associated with the end user (e.g., via both text message and/or mobile app notifications). The robotic interface subsystem may be operative to track each of the end user's medications and automatically reorder medications before they run out. At the user's request, the robotic interface subsystem may be operative to export medication adherence reports via e-mail or any other suitable communication mechanism to both caretakers and physicians and end users alike. The robotic interface subsystem may feature a software platform that may host third-party applications, such as telehealth services for further enhancing the healthcare management services of the robotic interface subsystem.

Figure 1:
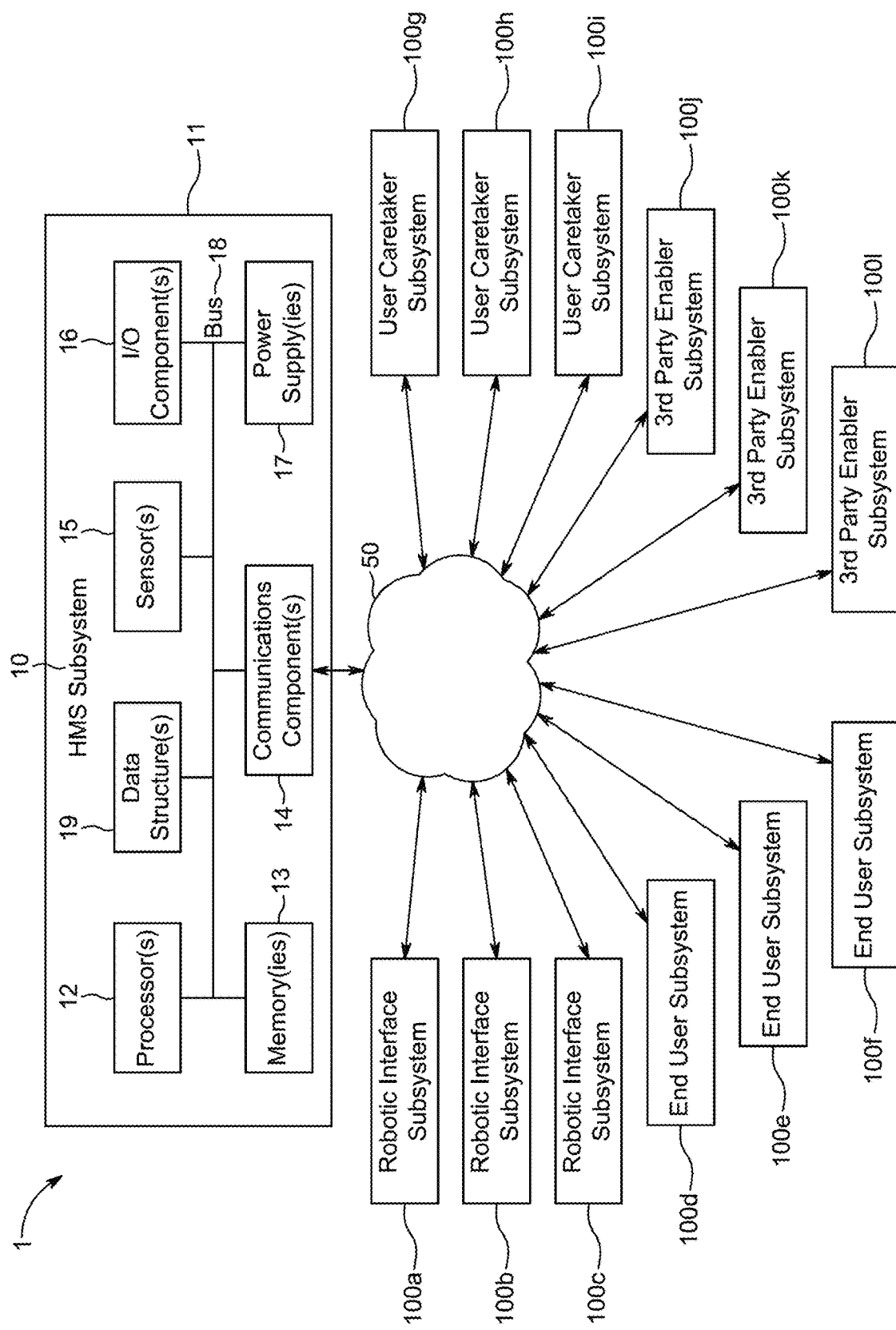
FIG. 1 is a schematic view of an illustrative system that may provide a healthcare management service of the disclosure.
Figure 1A:
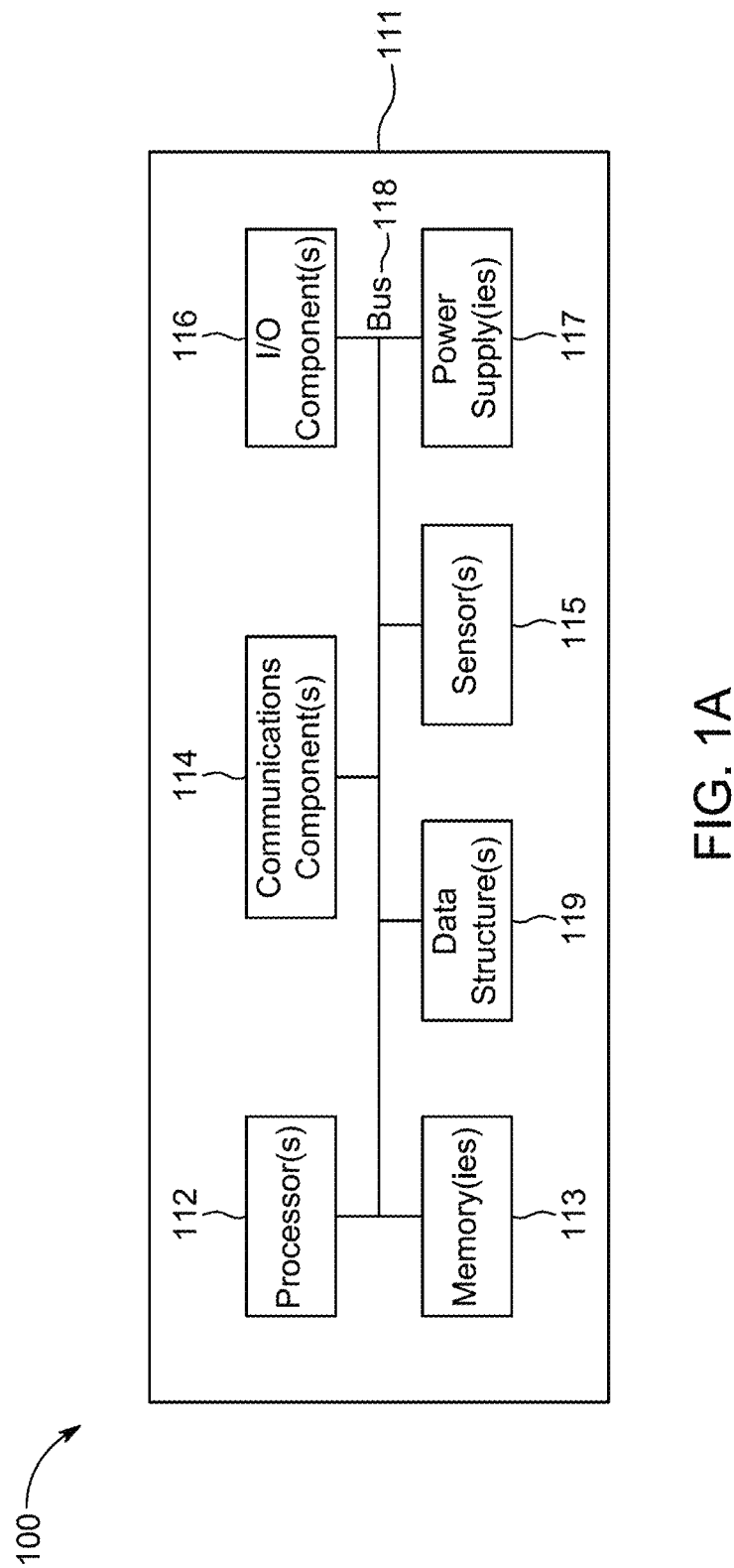
FIG. 1A is a more detailed schematic view of a subsystem of the system of FIG. 1.
Figure 2:
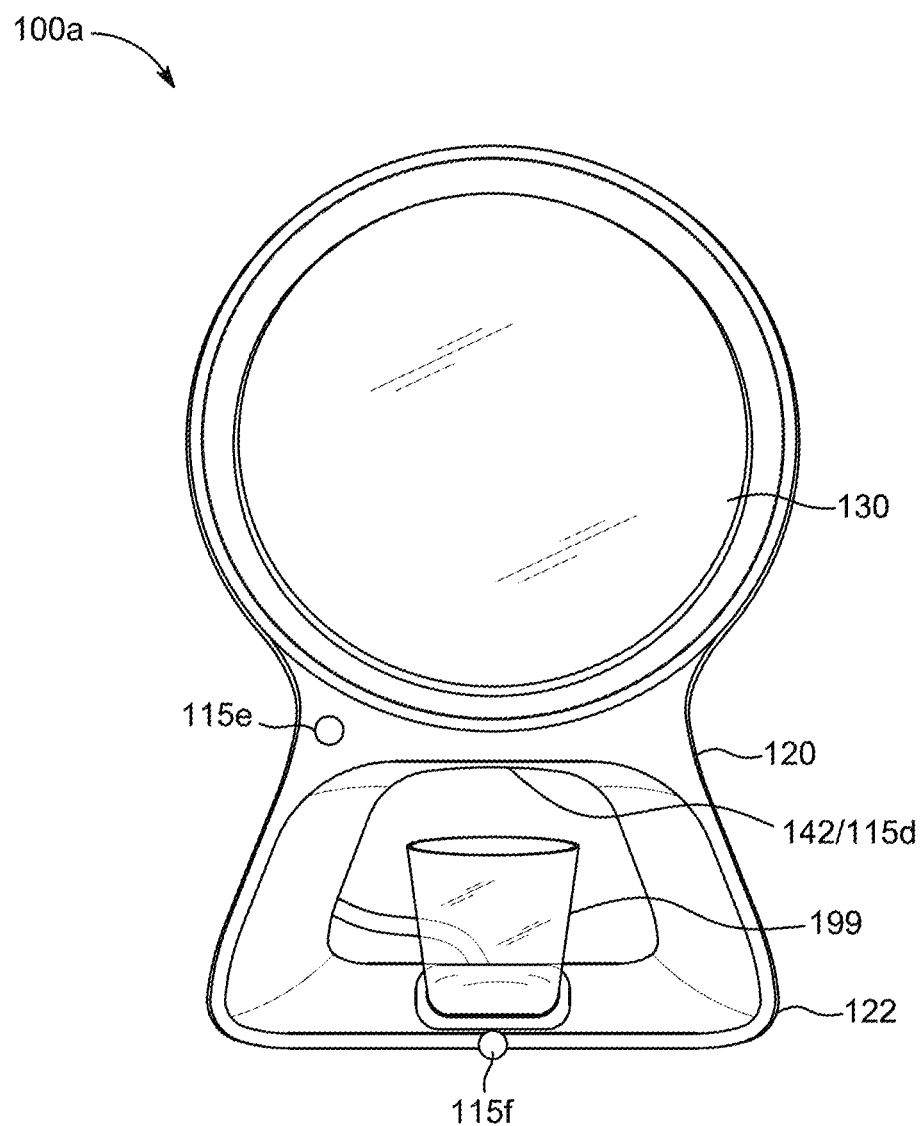
FIG. 2 is a front view of a robotic interface subsystem of the system of FIG. 1.
Figure 3:
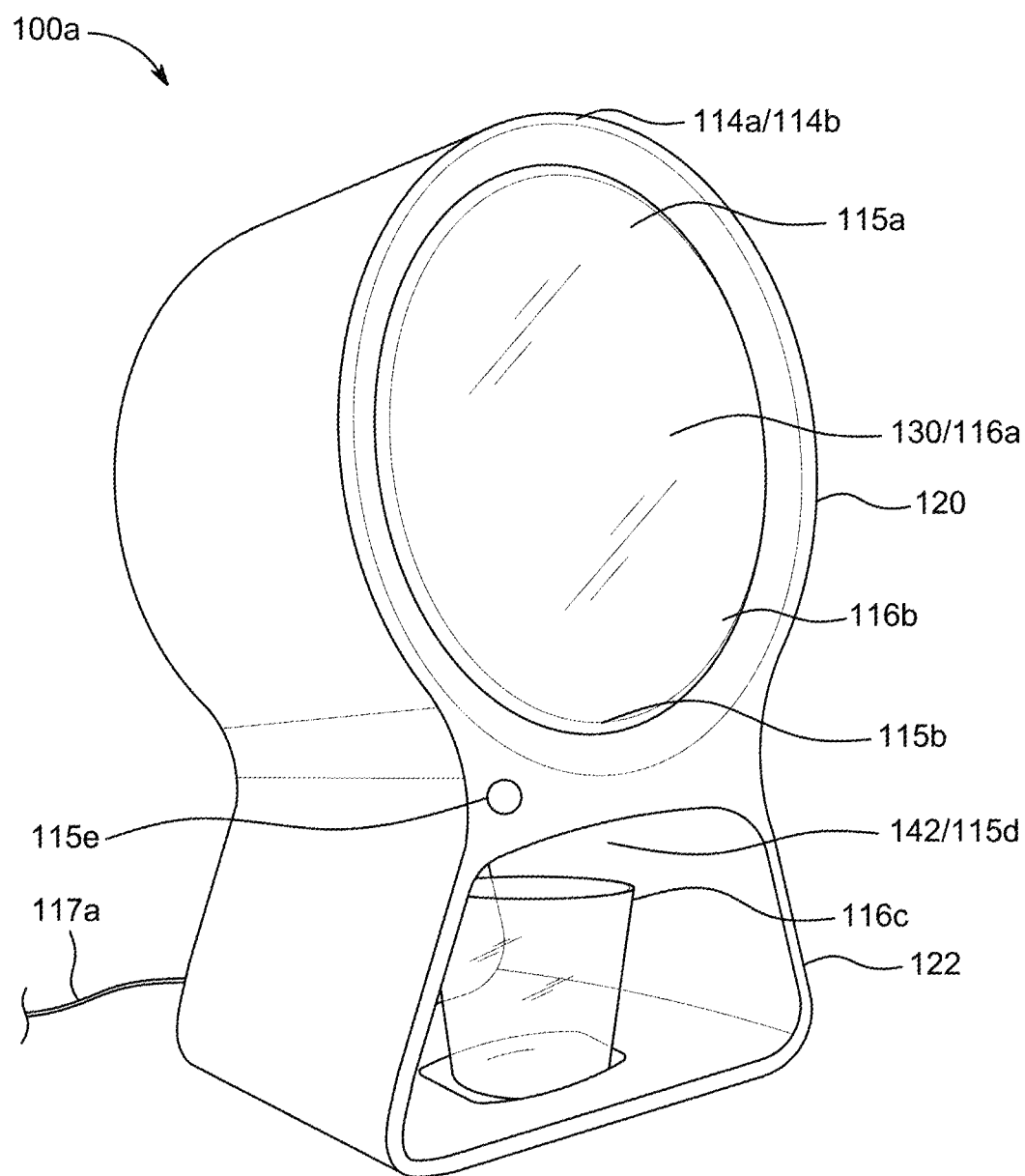
FIG. 3 is a front, right perspective view of the robotic interface subsystem of FIGS. 1-2.
Figure 4:
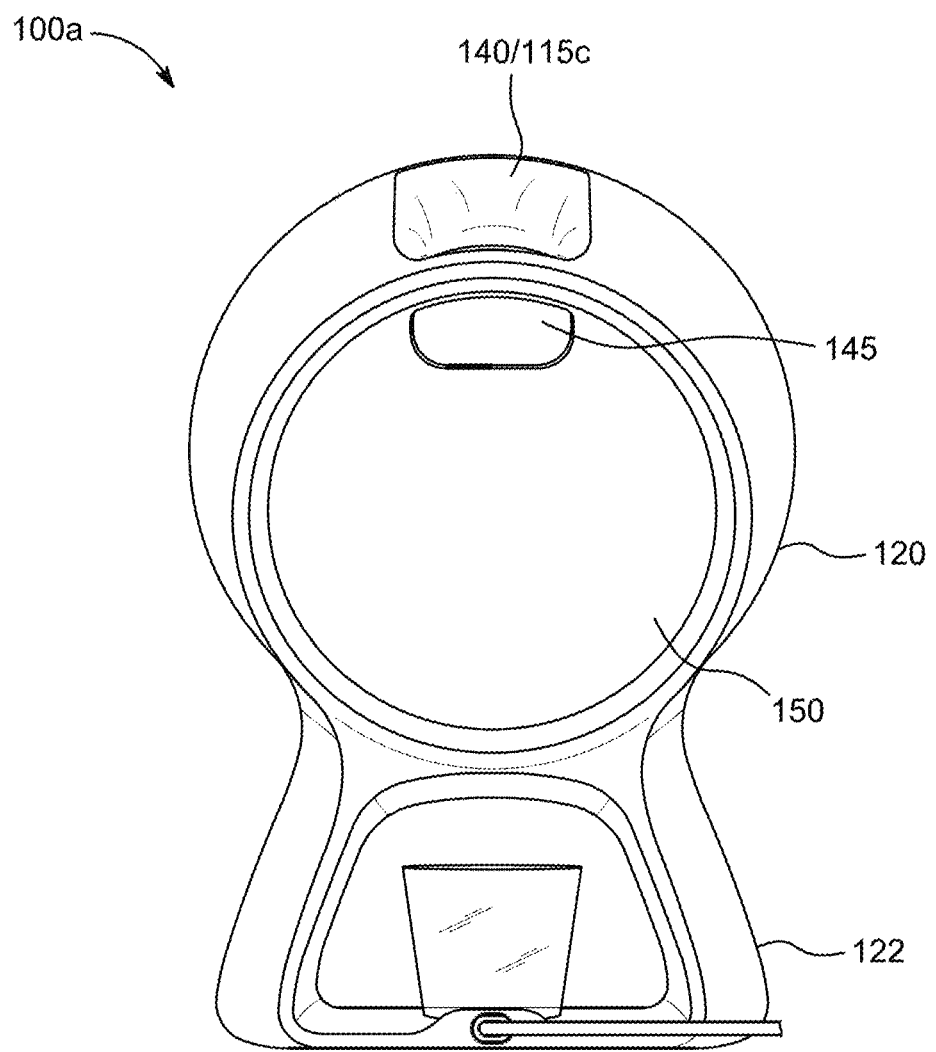
FIG. 4 is a back view of the robotic interface subsystem of FIGS. 1-3.
Figure 5:
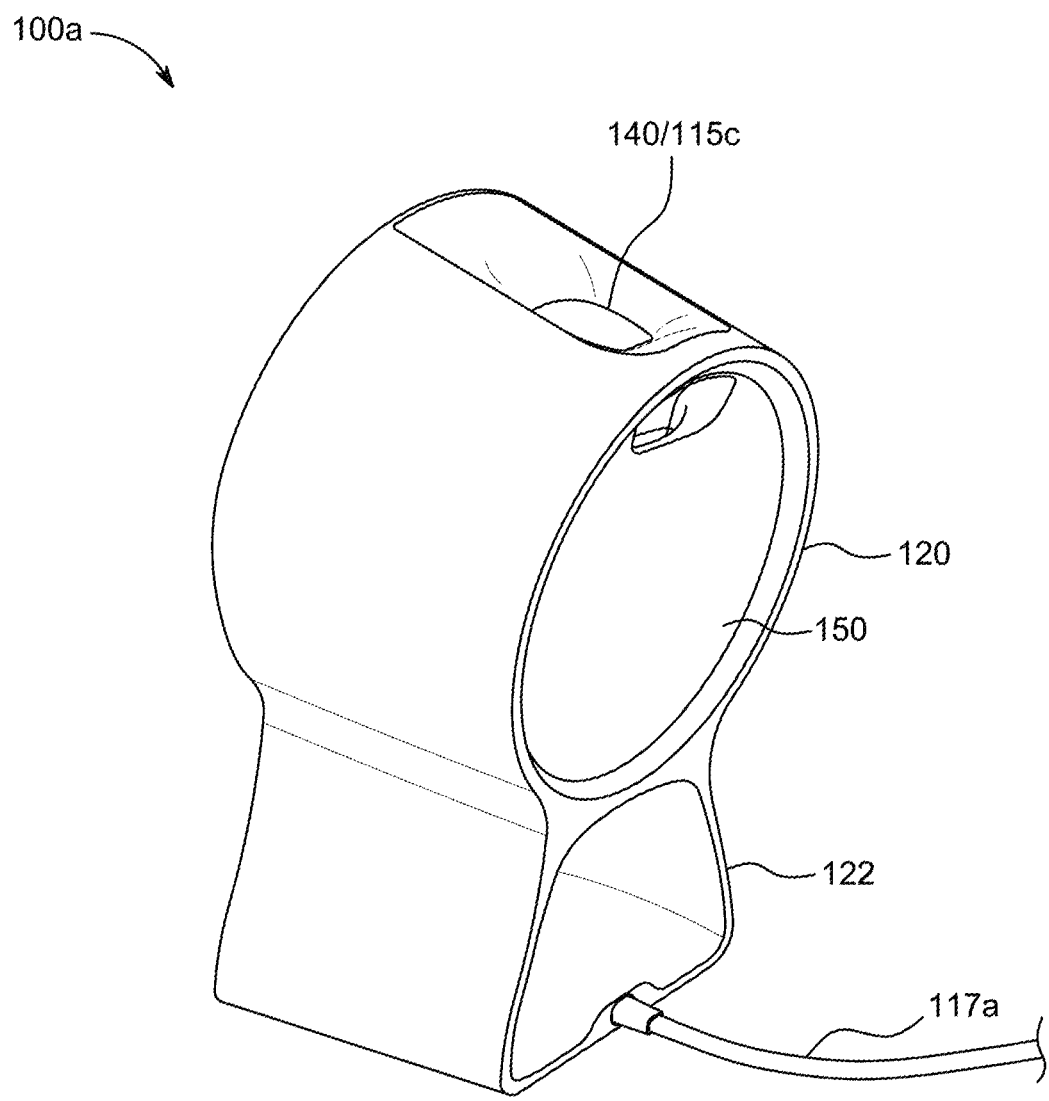
FIG. 5 is a back, left, top perspective view of the robotic interface subsystem of FIGS. 1-4.
Figure 6:
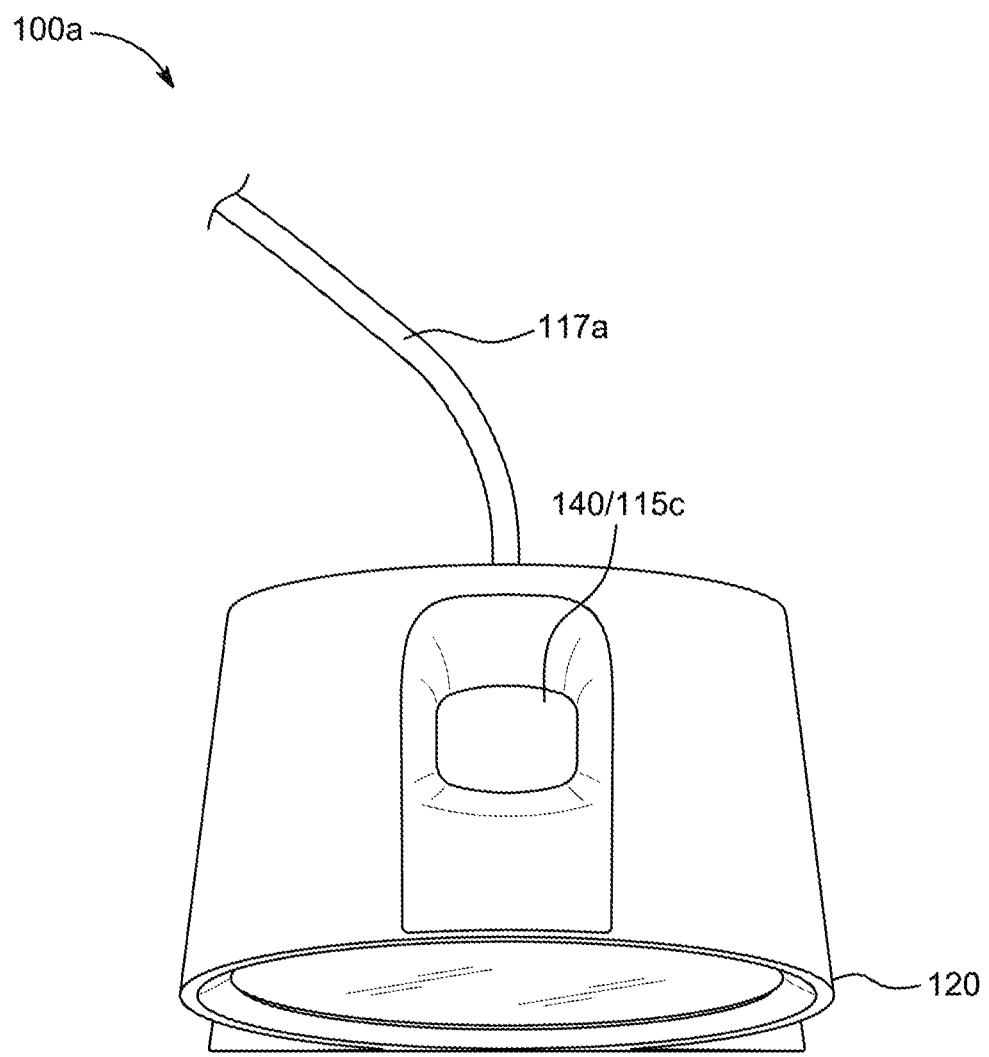
FIG. 6 is a front, top perspective view of the robotic interface subsystem of FIGS. 1-5.

Description of FIG. 1 and FIG. 1A

FIG. 1 is a schematic view of an illustrative system 1 in which a healthcare management service may be facilitated amongst various entities. For example, as shown in FIG. 1, system 1 may include a healthcare management service ("HMS") subsystem 10, various subsystems 100 (e.g., one or more robotic interface ("RI") subsystems 100a-100c, one or more end user ("EU") subsystems 100d-100f, one or more user caretaker ("UC") subsystems 100g-100i, and/or one or more third party enabler ("TPE") subsystems 100j-100l), and at least one communications network 50 through which any two or more of the subsystems 10 and 100 may communicate. HMS subsystem 10 may be operative to interact with any of the various subsystems 100 to provide a healthcare management service platform ("HMSP") that may facilitate various healthcare management services, including, but not limited to, facilitating and supervising a user's medication adherence, providing positive reinforcement to a healthy lifestyle, and answering health-related questions.

As shown in FIG. 1A, and as described in more detail below, a subsystem 100 may include a processor component 112, a memory component 113, a communications component 114, a sensor component 115, an input/output ("I/O") component 116, a power supply component 117, and/or a bus 118 that may provide one or more wired or wireless communication links or paths for transferring data and/or power to, from, or between various other components of subsystem 100. I/O component 116 may include at least one input component (e.g., a button, mouse, keyboard, microphone, data input connector, etc.) to receive information from a user of subsystem 100 and/or at least one output component (e.g., an audio speaker, video display, haptic component, data output connector, etc.) to provide information to a user of subsystem 100, such as a touch screen that may receive input information through a user's touch on a touch sensitive portion of a display screen and that may also provide visual information to a user via that same display screen. Memory 113 may include one or more storage mediums, including for example, a hard-drive, flash memory, permanent memory such as read-only memory ("ROM"), semi-permanent memory such as random access memory ("RAM"), any other suitable type of storage component, or any combination thereof. Communications component 114 may be provided to allow one subsystem 100 to communicate with a communications component of one or more other subsystems 100 or subsystem 10 or servers using any suitable communications protocol (e.g., via communications network 50). Communications component 114 can be operative to create or connect to a communications network for enabling such communication. Communications component 114 can provide wireless communications using any suitable short-range or long-range communications protocol, such as Wi-Fi (e.g., a 802.11 protocol), Bluetooth, radio frequency systems (e.g., 1200 MHz, 2.4 GHz, and 5.6 GHz communication systems), infrared, protocols used by wireless and cellular telephones and personal e-mail devices, or any other protocol supporting wireless communications. Communications component 114 can also be operative to connect to a wired communications network or directly to another data source wirelessly or via one or more wired connections or a combination thereof. Such communication may be over the internet or any suitable public and/or private network or combination of networks (e.g., one or more networks 50). Sensor 115 may be any suitable sensor that may be configured to sense any suitable data from an external environment of subsystem 100 or from within or internal to subsystem 100 (e.g., light data via a light sensor, audio data via an audio sensor, location-based data via a location-based sensor system (e.g., a global positioning system ("GPS")), etc.). Power supply 117 can include any suitable circuitry for receiving and/or generating power, and for providing such power to one or more of the other components of subsystem 100. Subsystem 100 may also be provided with a housing 111 that may at least partially enclose one or more of the components of subsystem 100 for protection from debris and other degrading forces external to subsystem 100. Each component of subsystem 100 may be included in the same housing 111 (e.g., as a single unitary device, such as a laptop computer or portable media device) and/or different components may be provided in different housings (e.g., a keyboard input component may be provided in a first housing that may be communicatively coupled to a processor component and a display output component that may be provided in a second housing, and/or multiple servers may be communicatively coupled to provide for a particular subsystem). In some embodiments, subsystem 100 may include other components not combined or included in those shown or several instances of any of the components shown.

Processor 112 may be used to run one or more applications, such as an application that may be provided as at least a part of one data structure 119 that may be accessible from memory 113 and/or from any other suitable source (e.g., from HMS subsystem 10 via an active internet connection). Such an application data structure 119 may include, but is not limited to, one or more operating system applications, firmware applications, communication applications, internet browsing applications (e.g., for interacting with a website provided by HMS subsystem 10 for enabling subsystem 100 to interact with an online service of HMS subsystem 10 (e.g., a HMSP) and/or any of its partners), HMS applications (e.g., a web application or a native application or a hybrid application that may be at least partially produced by HMS subsystem 10 or any of its partners for enabling subsystem 100 to interact with an online service of HMS subsystem 10 (e.g., a HMSP)), or any other suitable applications. For example, processor 102 may load an application data structure 119 as a user interface program to determine how instructions or data received via an input component of I/O component 116 or via communications component 114 or via sensor component 115 or via any other component of subsystem 100 may manipulate the way in which information may be stored and/or provided to a user via an output component of I/O component 116 and/or to any other subsystem via communications component 114. As one example, an application data structure 119 of a subsystem 100 may provide a subsystem user or a communicatively coupled device (e.g., accessory or peripheral device) with the ability to interact with a healthcare management service or the HMSP of HMS subsystem 10, where such an application 119 may be a third party application that may be running on subsystem 100 (e.g., an application (e.g., software and/or firmware) associated with HMS subsystem 10 that may be loaded on subsystem 100 from HMS subsystem 10 or via an application market or partner of HMS subsystem 10) and/or that may be accessed via an internet application or web browser running on subsystem 100 (e.g., processor 112) that may be pointed to a uniform resource locator ("URL") whose target or web resource may be managed by HMS subsystem 10 or any other remote subsystem. One, some, or each subsystem 100 may be a portable media device (e.g., a smartphone), a laptop computer, a tablet computer, a desktop computer, an appliance, a wearable electronic device, a virtual reality device, a dongle device, at least one web or network server (e.g., for providing an online resource, such as a website or native online application, for presentation on one or more other subsystems) with an interface for an administrator of such a server, and/or the like.

HMS subsystem 10 may include a housing 11 that may be similar to housing 111, a processor component 12 that may be similar to processor 112, a memory component 13 that may be similar to memory component 113, a communications component 14 that may be similar to communications component 114, a sensor component 15 that may be similar to sensor component 115, an I/O component 16 that may be similar to I/O component 116, a power supply component 17 that may be similar to power supply component 117, and/or a bus 18 that may be similar to bus 118. Moreover, HMS subsystem 10 may include one or more data sources or data structures or applications 19 that may include any suitable data or one or more applications (e.g., any application similar to application 119) for facilitating a healthcare management service or HMSP that may be provided by HMS subsystem 10 in conjunction with one or more subsystems 100. Some or all portions of HMS subsystem 10 may be operated, managed, or otherwise at least partially controlled by an entity (e.g., administrator) responsible for providing a healthcare management service to one or more clients or other suitable entities.

HMS subsystem 10 may communicate with one or more subsystems 100 via communications network 50. Network 50 may be the internet or any other suitable communication network, such that when intercoupled via network 50, any two subsystems of system 1 may be operative to communicate with one another (e.g., a subsystem 100 may access information (e.g., from a data structure 19 of HMS subsystem 10, as may be provided as a healthcare management service via processor 12 and communications component 14 of HMS subsystem 10 or from a data structure of another subsystem 100) as if such information were stored locally at that subsystem 100 (e.g., in memory component 113)).

Various clients and/or partners may be enabled to interact with HMS subsystem 10 for enabling the healthcare management services and the HMSP. For example, at least one robotic interface subsystem of system 1 (e.g., each one of the one or more robotic interface subsystems 100a-100c) may be any suitable subsystem (e.g., robotic companion device) that may be interacted with by any suitable end user ("EU") that may own, rent, or otherwise have access to such a robotic interface subsystem. At least one end user subsystem of system 1 (e.g., each one of the one or more end user subsystems 100d-100f) may be any suitable subsystem (e.g., portable computing device) that may be communicatively coupled to a respective robotic interface subsystem (e.g., via any suitable network 50). For example, an end user subsystem may be any suitable personal computing device (e.g., laptop computer, desktop computer, telephone, smart watch, and/or the like) that may be used by a particular end user and, optionally, accessible to the end user at most times (e.g., a device worn by the end user or carried by the end user in a pocket or purse during most daily activities), which may be operative to communicate any suitable data with a robotic interface subsystem of the same end user (e.g., reminders and/or health information) and/or with HMS subsystem 10 via any suitable communications path (e.g., any suitable wired or wireless communications path using any suitable communications protocol). At least one user caretaker subsystem of system 1 (e.g., each one of the one or more user caretaker subsystems 100g-100i) may be any suitable subsystem (e.g., personal computing devices, servers, etc.) operated or managed by any suitable entity that may be interested in following the healthcare status of any particular end user of the HMSP (e.g., any suitable physician and/or healthcare professional associated with the end user and/or a friend or family member of the end user) by communicating appropriate information with various other subsystems of the HMSP. At least one third party enabler subsystem of system 1 (e.g., each one of the one or more third party enabler subsystems 100j-100l) may be operated by any suitable third party enabler ("TPE") that may be operative to enable at least partially any suitable operation provided by the HMSP, such as a third party application or service provider that may be operative to process or provide any suitable subject matter that may be used by any other suitable subsystem of system 1 for enabling the HMSP (e.g., any telehealth service providers or healthcare information databases that may be able to provide answers to any suitable healthcare related questions (e.g., what foods ought to be avoided when taking certain medication, what are the symptoms for a particular condition, etc.), any medication providers (e.g., pharmacy that may be able to fulfill and/or deliver medication to an end user), any home automation systems (e.g., any suitable subsystems that may automate any components of an end user's home or other surrounding environment), booking subsystems (e.g., transportation service subsystems (e.g., Uber Technologies, etc.), healthcare service subsystems (e.g., ZocDoc, Inc., etc.), wearable sensor subsystems (e.g., smart watches, medical devices, virtual and/or augmented reality devices, etc.), any social networks that may provide any suitable connection information between various parties, government agencies/regulators, licensing bodies, third party advertisers, owners of relevant data, sellers of relevant goods/materials, software providers, and/or any other suitable third party service provider distinct from an RI subsystem, EU subsystem, UC subsystem, and HMS subsystem 10).

Each subsystem 100 of system 1 (e.g., each one of subsystems 100a-100l) may be operated by any suitable entity for interacting in any suitable way with HMS subsystem 10 (e.g., via network 50) for deriving value from and/or adding value to a service of the HMSP of HMS subsystem 10. For example, a particular subsystem 100 may be a server operated by a client/partner entity that may receive any suitable data from HMS subsystem 10 related to any suitable healthcare management enhancement of the HMSP provided by HMS subsystem 10 (e.g., via network 50). Additionally or alternatively, a particular subsystem 100 may be a server operated by a client/partner entity that may upload or otherwise provide any suitable data to HMS subsystem 10 related to any suitable healthcare management service of the HMSP provided by HMS subsystem 10 (e.g., via network 50).

Description of FIGS. 2-12

System 1 may be utilized to manage the healthcare of at least one end user through interaction with an associated robotic interface subsystem in any suitable manner, including, but not limited to, facilitating and supervising the end user's medication adherence, providing the end user with positive reinforcement for a healthy lifestyle, and/or answering health-related questions of the end user. For example, as shown in FIGS. 2-12, an illustrative robotic interface subsystem 100a may be provided with at least certain hardware and may be configured to function as a healthcare companion for an end user. RI subsystem 100a may be operative to interact with an end user via voice to assist the user with its healthcare needs and answer simple healthcare questions for educational purposes. RI subsystem 100a may be configured to include the capability to store medications and dispense medications according to any suitable schedule accessible to RI subsystem 100a (e.g., a schedule that an end user may manually input into RI subsystem 100a via an I/O component 116 of RI subsystem 100a and/or a schedule that may be loaded onto RI subsystem 100a from a remote source (e.g., HMS subsystem 10 and/or any other suitable subsystem 100 of system 1). At the specified times of the schedule, RI subsystem 100a may be operative to issue voice or other audible or haptic or visual reminders to an end user and to confirm the user's identity and presence (e.g., using facial recognition functionality and/or any suitable biometric sensor (e.g., fingerprint sensor) before dispensing the appropriate medication. If a medication dose of the schedule is missed (e.g., not dispensed to an end user), RI subsystem 100a may be operative to alert the end user (e.g., at an end user subsystem) and/or any associated caretaker of the end user (e.g., at a user caretaker subsystem) with any suitable communication (e.g., text message and/or mobile app notification (e.g., via an app of the HMSP that may be available on the end user subsystem and/or on the user caretaker subsystem). RI subsystem 100a may be operative to track a user's medications and automatically reorder medications any suitable amount of time (e.g., seven days) before they run out. At the user's request or after any other suitable approval, RI subsystem 100a may be operative to export medication adherence reports via e-mail or any other suitable communication to any suitable caretaker subsystems of any suitable caretakers that may be associated with the end user. RI subsystem 100a may be operative to run any suitable firmware and/or software platform (e.g., of the HMSP) that may host third-party applications, such as telehealth service applications, to enhance the health management services of system 1.

Figure 10:
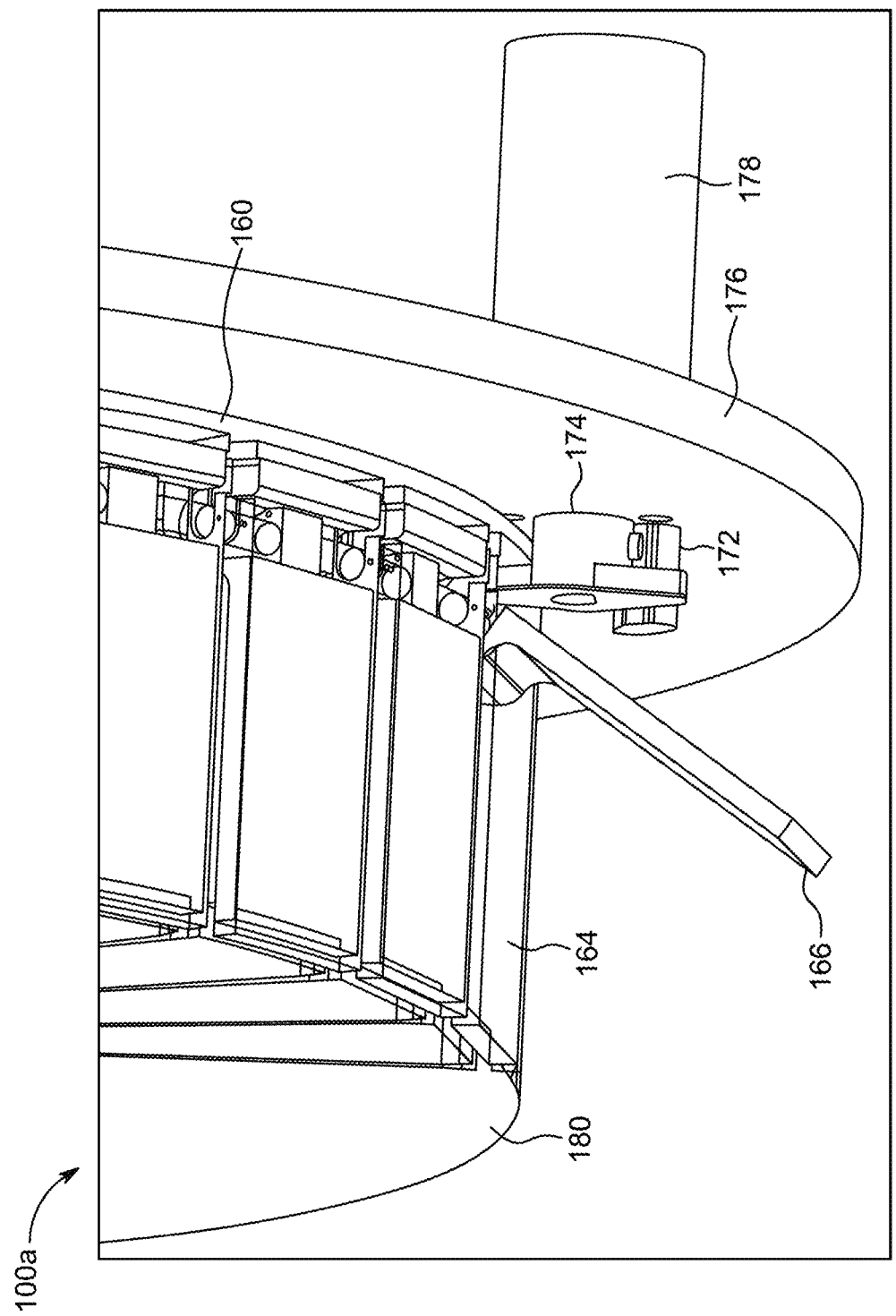
FIG. 10 is a back, right, bottom perspective view of another portion of the subsystem of FIGS. 1-9.
Figure 11:
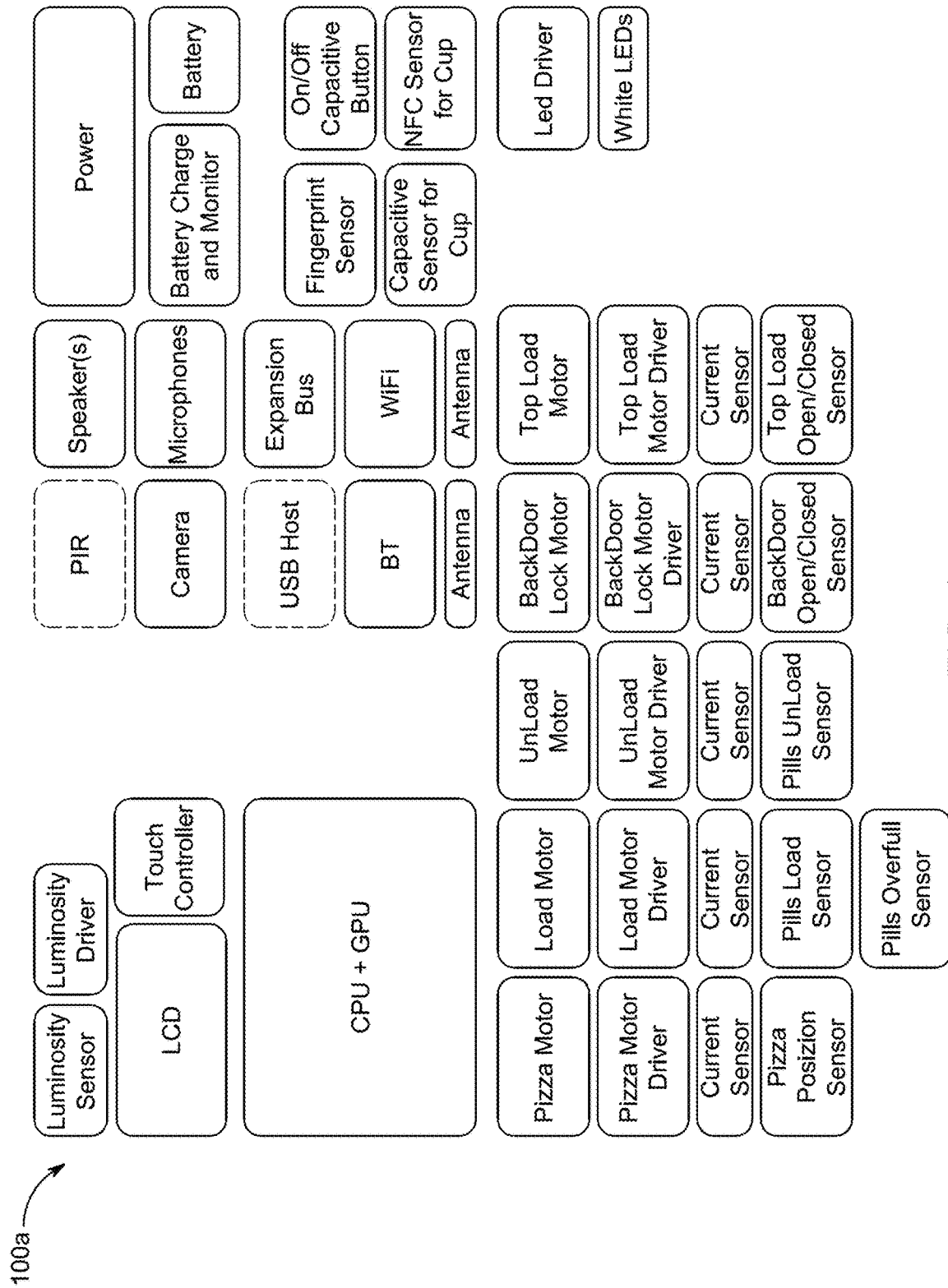
FIG. 11 is a schematic of additional components of the subsystem of FIGS. 1-10.
Figure 12:
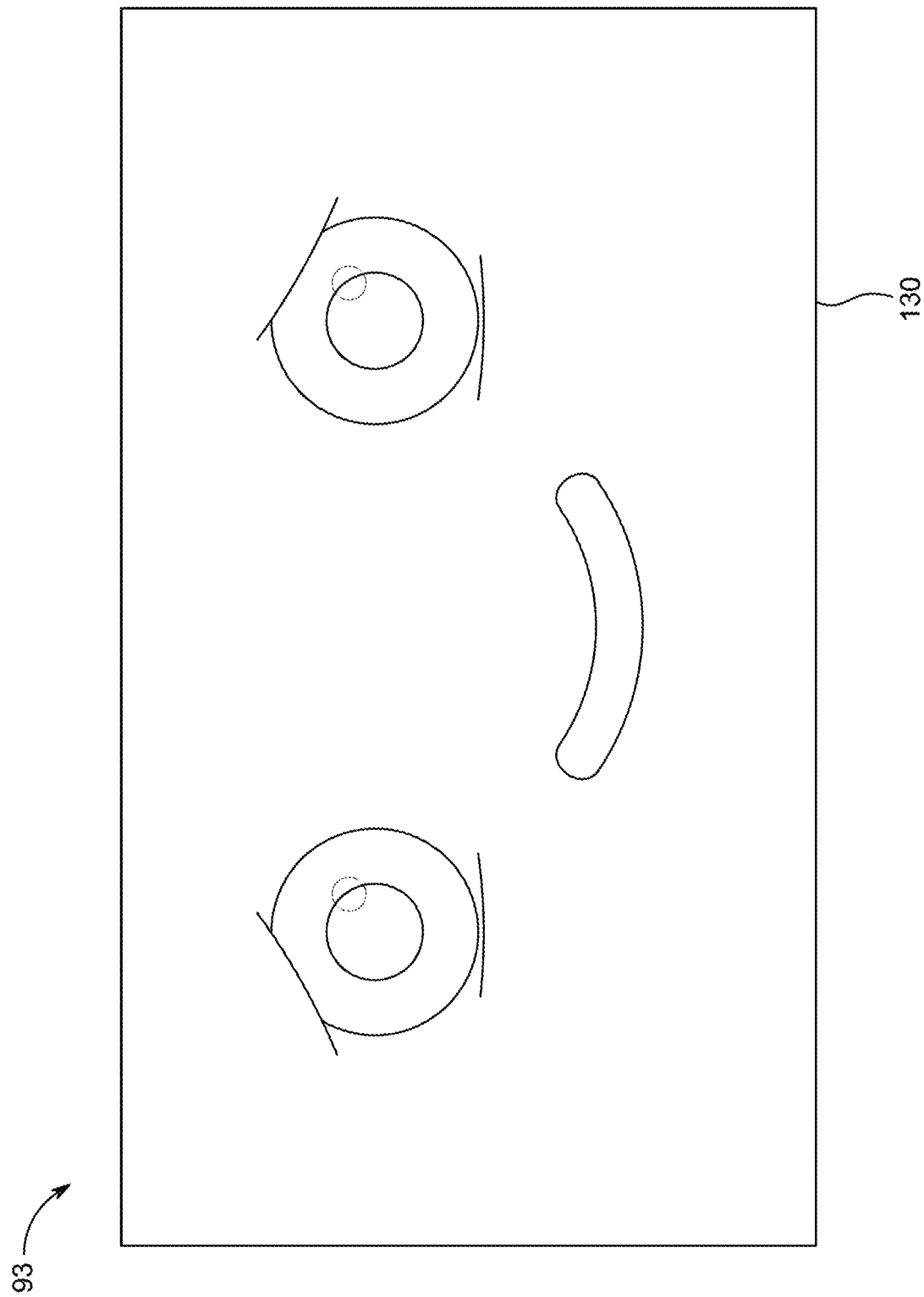
FIG. 12 is a front view of a display screen portion of the subsystem of FIGS. 1-11.

As shown in FIGS. 2-10, for example, RI subsystem 100a may be designed to be sleek and fashionable for the home or other environment of the end user. A main body 120 of RI subsystem 100a may feature curved edges and/or a high quality glossy finish. The form factor may represent an anthropomorphic assistant with a face 93 on a circular or any other suitably shaped screen 130 (see, e.g., FIG. 12). Screen 130 may be provided as a portion of a touchscreen or non-touchscreen I/O component 116 of RI subsystem 100a. For example, such a touchscreen may be exposed at a front of a circular portion of main body 120 (e.g., main body of housing 111 of RI subsystem 100a). On top of main body 120 may be a hatch 140 that may be configured to automatically open for enabling one or more internal compartments within main body 120 to be filled with medication or any other suitable content. For example, hatch 140 may be controlled by one or more motors (e.g., one or more motor(s) of FIG. 11) that may be operative to open or close hatch 140 when appropriate, such as when a load operation is appropriate. A load operation may trigger when a user interacts with RI subsystem 100a to load a medication or other material into an internal compartment, such that a container 160 may be rotated or otherwise moved to align a compartment with hatch or inlet port 140, and then RI subsystem 100a may be operative to open hatch 140 and instruct the user to load any suitable amount of material (e.g., one dose of medication) therein, after which container 160 may be rotated or otherwise moved to align another compartment with hatch 140 to repeat the process as appropriate. Hatch 140 may be closed once the filling process has been completed. On a bottom or downwardly facing surface of main body 120 may be a second hatch or outlet port 142 that may be configured to open for dispensing content (e.g., medications) from the internal compartment(s) of main body 120 for retrieval by an end user (e.g., into a receptacle 199 (e.g., drinking glass) that may be positioned underneath hatch 142 to receive contents from the compartment of main body 120 via hatch 142 and that may then be held and moved by an end user away from RI subsystem 100a for use of the contents). One or more sensors (e.g., capacitive and/or near-field communication ("NFC") sensor(s)) may be provided to determine if a particular container (e.g., a glass receptacle or a plastic receptacle or no receptacle) is positioned adjacent dispensing hatch 142. As shown in FIG. 11, one or more pill overfull sensors (e.g., an IR sensor or a camera) may be provided by RI subsystem 100a (e.g., positioned at or near the top of hatch 140) to detect when pills or other material have been loaded and/or to determine if the compartment is full or nearing capacity or is almost empty or completely empty.

A back of main body 120 may include a cover 150 with a handle 145 that may allow access to the internal receptacle(s) (e.g., medication container(s)) within main body 120). Cover 150 may be configured to be removed for enabling access to the internal receptacle(s) only upon user authentication via fingerprint verification or any other suitable authentication (e.g., using any suitable sensor of subsystem 100a), such that the contents may be protected from people other than the appropriate end user (e.g., meddling children or a thieves). For example, external-facing screws (not shown) may require a proprietary screwdriver to be removed from cover 150 and main body 120, ensuring the security of the internal contents of the internal receptacle(s) of main body 120.

Main body 120 may at least partially enclose or support an ARM-based mobile processor 112, an LCD touchscreen 130 of I/O component 116a (e.g., a high definition touchscreen display), external camera sensor 115a, at least one microphone sensor 115b (e.g., one or two omnidirectional microphones), at least one speaker I/O component 116b (e.g., tweeter and subwoofer), any suitable wireless communication adapters 114 (e.g., a Wi-Fi transceiver 114a and a Bluetooth transceiver 114b). One or more light emitting I/O components 116c (e.g., mood lights) may be provided adjacent hatch 142 for illuminating the space at which contents may be released from main body 120 for an end user. One or more motion sensors and/or image or camera sensors 115c and 115d may be provided hatch 140 and hatch 142, respectively, to detect filling and dispensing of contents with respect to the internal receptacle(s) of main body 120.

Figure 7:
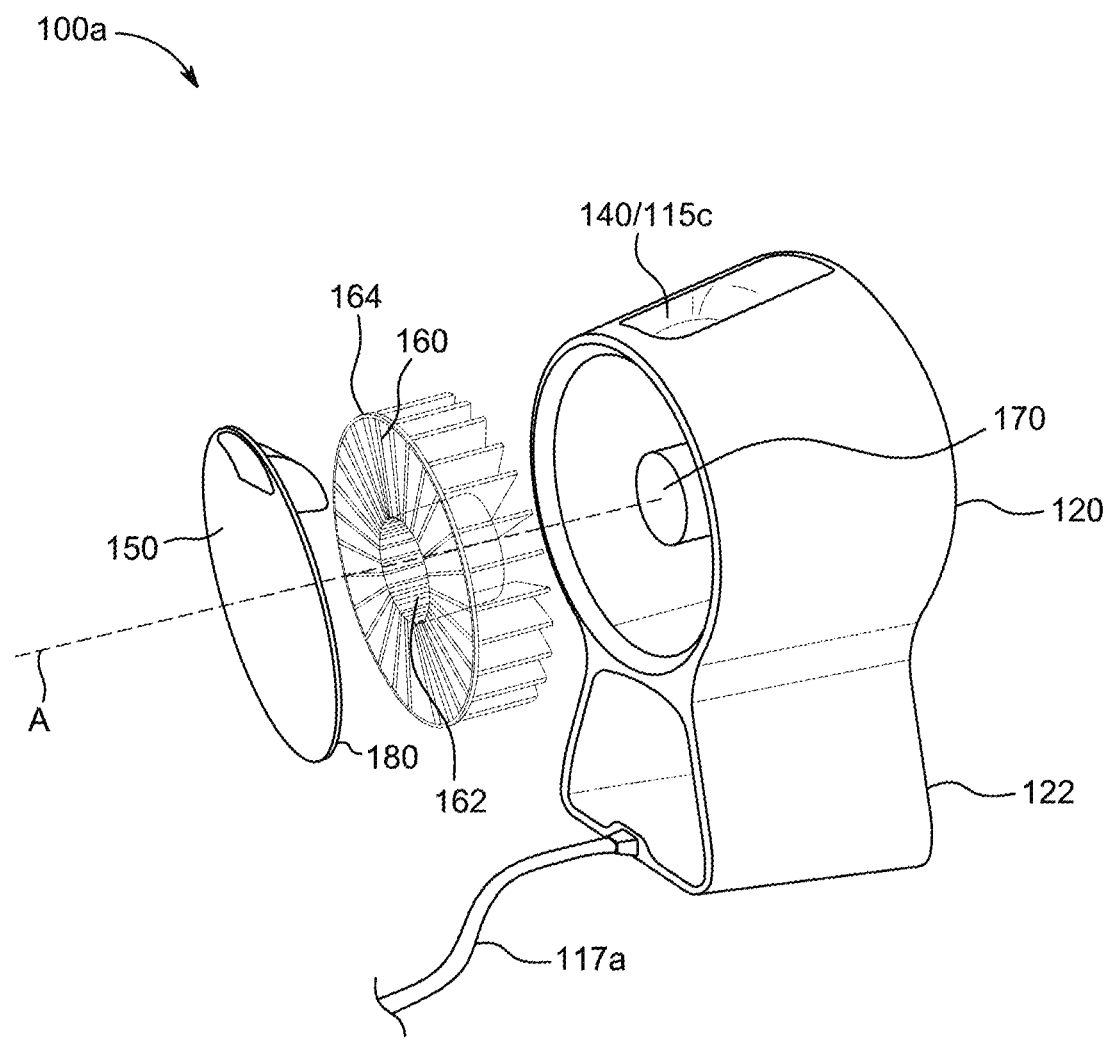
FIG. 7 is a back, right, top perspective view of the robotic interface subsystem of FIGS. 1-6 with portions of the subsystem in exploded view.
Figure 8:
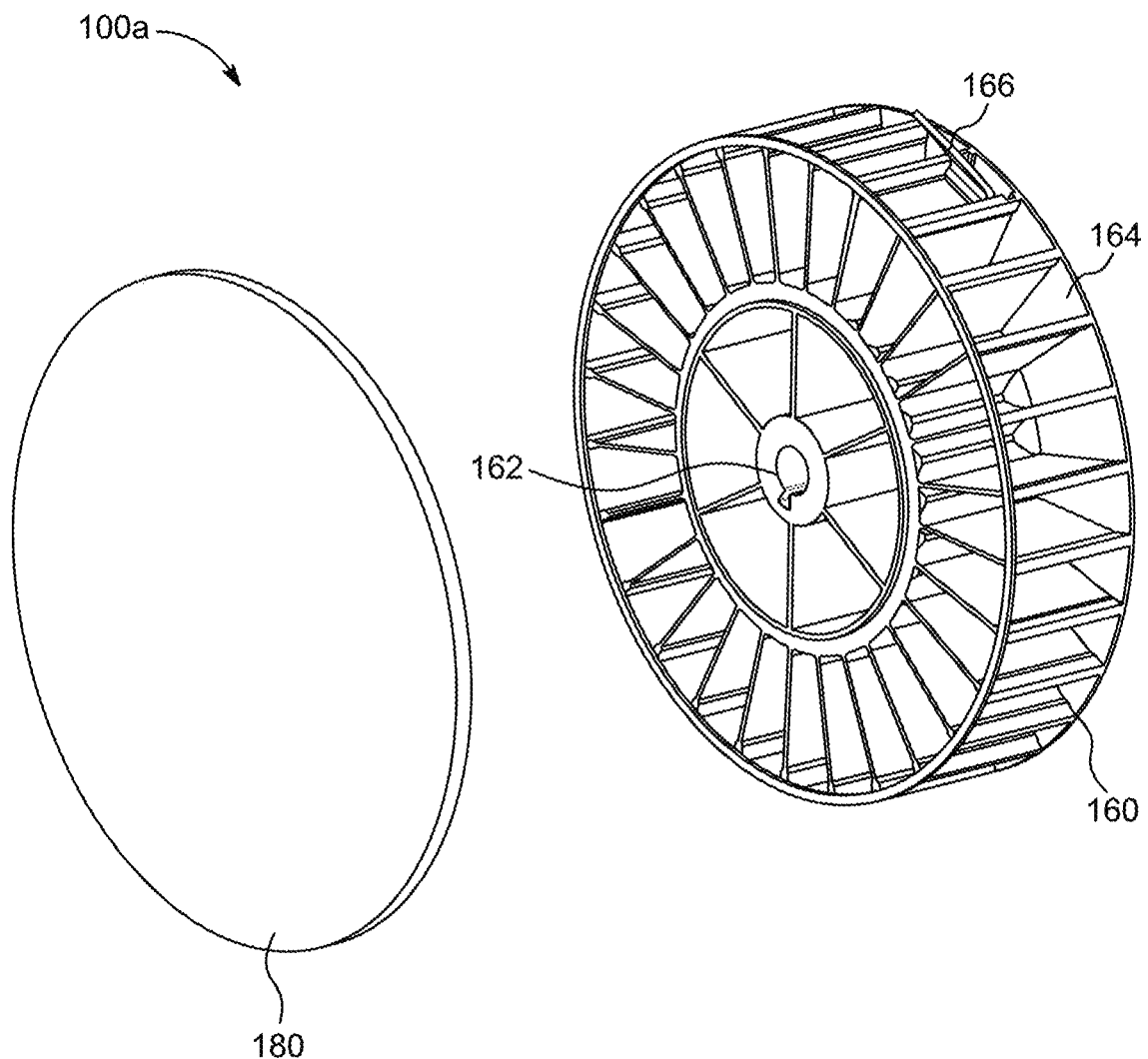
FIG. 8 is a back, right, top perspective view of the portions of the subsystem of FIG. 7 in exploded view.
Figure 9:
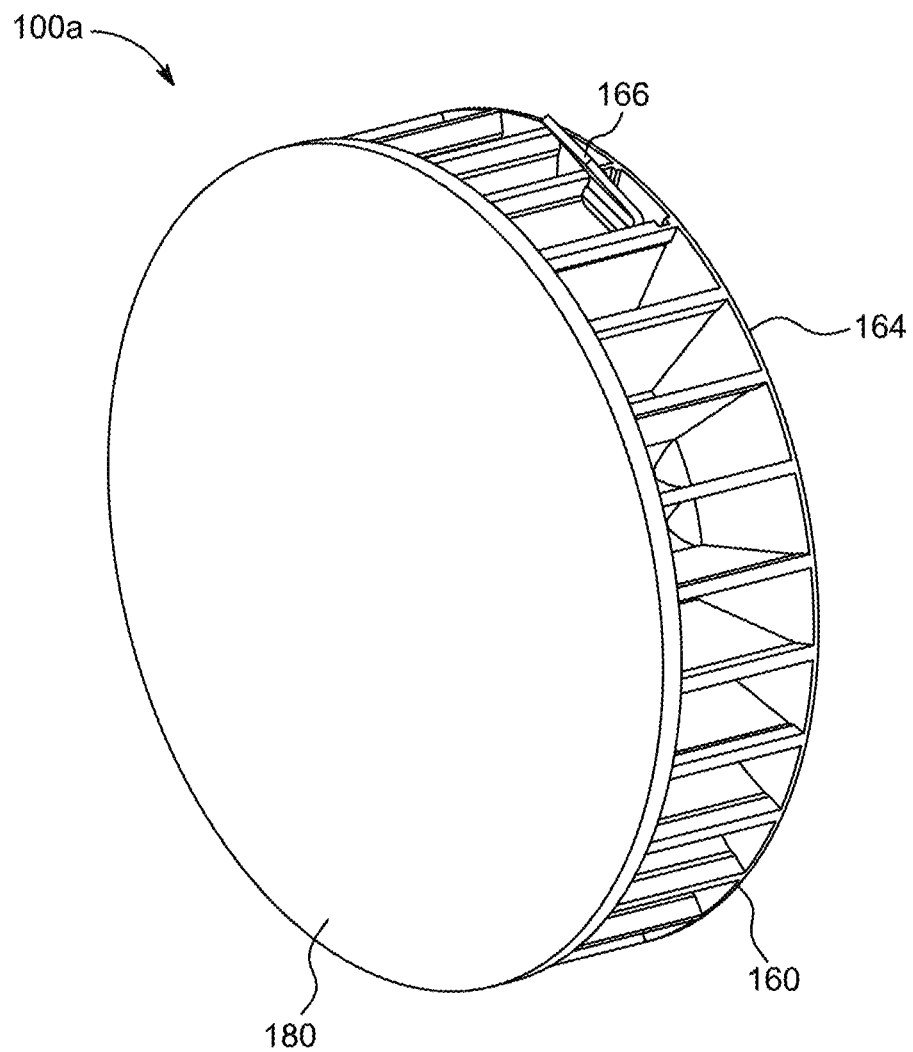
FIG. 9 is a back, right, top perspective view of the portions of the subsystem of FIGS. 7 and 8 in combined view.

The internal receptacle(s) of main body 120 may be provided by any suitable container 160 (e.g., a removable antibacterial medicine container). As shown, container 160 may be provided as a circular container of any suitable material (e.g., plastic) with a central spoke opening 162 for motorized rotation about an axis A by any suitable motor 170 that may be positioned at least partially within or supported by main body 120. Container 160 may be subdivided to include any suitable number (e.g., 28 or 31) of compartments 164 in a circumferential manner. Each compartment 164 may be sized to receive and retain at least one dose of at least one medication for an end user. Container 160 may be covered by a cover 180 that may be removable (along with or independently of cover 150) from container 160 (e.g., as shown in FIGS. 7 and 8) to facilitate visualization of some or all compartments 164 for enabling cleaning of compartments 164 and/or manual loading of contents by an end user into compartments 164. On the circumference of container 160, each small compartment 164 may feature a spring-loaded door 166 that may be operative to open to expose an opening into its respective compartment 164 when that compartment 164 and door 166 is aligned with either hatch 140 for filling compartment 164 with contents or hatch 142 for dispensing contents from compartment 164 and main body 120. Motor 170 may rotate container 160 about axis A under the control of a microcontroller that may separate from a primary processor 112 of RI subsystem 100a. When compartment 164 and door 166 may be aligned with hatch 140, material (e.g., medication (e.g., a single dose)) may be inserted into hatch 140 and compartment 164 by the user. To facilitate removing certain material from an external container (e.g., one pill from a medication bottle) and dropping it into hatch 140, a customized cap dispenser may be coupled to the external container for guiding particular material into hatch 140. Such a cap dispenser may include a shutter mechanism that may be operative to release one pill when a pushbutton is pressed. The user can invert the external container or medication bottle with the cap dispenser attached, press the pushbutton, and release one pill into hatch 140 in a rapid manner. As shown in FIG. 10, for example, a stop 172 (e.g., a mechanical limit stop) may be provided and used to reset a motor 178 to a zero position and/or to limit the movement of a mechanism 174 (e.g., a mechanical rocker) that may be configured to open door 166 (e.g., a spring-loaded door). Motor 178 may be any suitable motor, such as an electric motor, that may be operative to move mechanism 174 to open one or more doors 166, while a mechanism 176 may be any suitable support (e.g., mechanical support) for motor 178.

Main body 120 of RI subsystem 100a may be perched on a stand 122 that may permit receptacle 199 to be positioned under main body 120 for catching any contents dispensed from any compartment 164 of container 160. Directly above receptacle 199 may be one or more light emitting I/O components 116c (e.g., mood lights) for illuminating the space at which contents may be released from main body 120 for an end user (e.g., for illuminating receptacle 199 when it contains medications). For example, one or more light emitting I/O components 116c may be turned on independently of the presence or absence of material (e.g., medications) inside receptacle 199, but instead one or more light emitting I/O components 116c may be turned on when RI subsystem 100a determines that a user's attention ought to be attracted to RI subsystem 100a for reminding the user to access certain material (e.g., certain medication). RI subsystem 100a may be configured to determine whether the appropriate material has been dispensed into receptacle 199 and/or whether receptacle 199 has been removed from the position to receive material from RI subsystem 100a (e.g., using any suitable sensor(s), such as one or more capacitive and/or NFC sensors). Once it has been detected that a user has removed a receptacle in which material had been dispensed, one or more light emitting I/O components 116c may be turned off. RI subsystem 100a may also include one or more suitable user authentication sensors 115e (e.g., a fingerprint scanner sensor or any other suitable biometric sensor(s)) for added security, as noted above, that may require an appropriate end user be detected before any contents from container 160 may be released from main body 120 (e.g., into receptacle 199). Stand 122 may at least partially protect or support power supply 117 of RI subsystem 100a (e.g., a wired power supply (e.g., via power cable 117a) and a lithium-ion battery that may assures all basic functions of RI subsystem 100a remain active in the event of a power outage). Immediately below or adjacent a side of a properly positioned receptacle 199 there may be provided at least one sensor 115f that may be built into or otherwise supported by stand 122. For example, a first sensor 115f may be a capacitive sensor that may be operative to detect the presence of any receptacle 199 under hatch 142, while a second sensor 115f may be a radio frequency identification ("RFID") or NFC sensor that may be operative to read a specific RFID or NFC tag of receptacle 199 (e.g., to determine the type of receptacle and the owner of the receptacle). A user may be provided with two or more particularly tagged receptacles 199 (e.g., a glass receptacle for home use and a plastic receptacle for travel) that may be associated by the HMSP with the particular user and particular biometrics of the user that may detected by sensor(s) 115e or otherwise in conjunction with the data received by sensor(s) 115f to confirm authentication of a particular end user prior to dispensing contents (e.g., medication) from hatch 142. Two independent microcontrollers may verify the biometric data detected by sensor(s) 115e and synthesize such data with any receptacle data detected by sensor(s) 115f. RI subsystem 100a may be configured to detect the presence of receptacle 199 utilizing any suitable methods, including, but not limited to, near field communication and capacitive sensing. For example, a tag may be embedded in (e.g., in the bottom of) or otherwise coupled to receptacle 199. Any suitable component (e.g., concentric copper tracks on the base of stand 122) may be operative to detect the presence of a specific receptacle 199 with all accompanying information, such as type of receptacle (e.g., plastic to-go receptacle or glass home-use receptacle) and owner of the receptacle (e.g., a particular user of potentially multiple users of the system). Alternatively, no tag may be coupled to receptacle 199. Instead, detection of receptacle 199 may be accomplished by RI subsystem 100a monitoring the capacitance between a component (e.g., one or more copper tracks on the base of stand 122). For the purpose of detecting receptacle 199, an integrated system with concentric copper tracks on the base of stand 122 can either function as an antenna for specific tags or as a capacitive sensor. Commutation between the two functions may either be electro-mechanical (e.g., relay commutation) or solid state.

Any suitable data structure(s) 119 of RI subsystem 100a may be accessible to RI subsystem 100a and used to drive RI subsystem 100a (e.g., a processor 112 of RI subsystem 100a). For example, any suitable data structure(s) 119 of RI subsystem 100a may be a firmware or software application operating system based on a customized platform (e.g., of an Android and/or iOS platform). Key functionalities of such an application may be interactivity, reliability, safety, and/or versatility. Such an application may enable RI subsystem 100a to interact with an end user via an anthropomorphic persona of RI subsystem 100a. Such a persona may include two eyes that express human emotion and a mouth (e.g., features of face 93) that may mirror movements associated with human speech indicative of audible information presented by any speaker I/O component of RI subsystem 100a. For example, RI subsystem 100a may be configured to better address the social and emotional needs of a user because RI subsystem 100a may integrate information from its programmed schedule, camera, microphone, cloud based medication database, and/or any other available features to interact with the user proactively. For example, if a particular medication has a common side effect, RI subsystem 100a may be configured to inquire whether the user is experiencing the side effect. In addition, RI subsystem 100a may be configured to be fully responsive to voice inquiries and/or commands of the user. RI subsystem 100a, therefore, may be operative to answer health-related questions and recommend a telehealth visit if RI subsystem 100a cannot provide a satisfactory answer.

RI subsystem 100a may be configured to be constantly aware of its surroundings. Using its camera(s) and/or microphone(s) and/or any other suitable sensors 115, RI subsystem 100a may be configured to identify any particular end user of the HMSP as the user enters a detectable sphere of RI subsystem 100a. Upon user detection and identification, RI subsystem 100a may be configured to awaken (e.g., power certain other components of RI subsystem 100a) so as to be able to respond to end user commands, as necessary. Initial user identification by RI subsystem 100a may rely on facial recognition or any other suitable detection technique. RI subsystem 100a may be configured to detect faces in real-time. The image of a detected face may be uploaded or otherwise shared with a backend cloud server (e.g., HMS subsystem 10 and/or an appropriate TPE subsystem) that may process such an image for facial recognition purposes (e.g., against all known users of the HMSP or of that particular RI subsystem 100a) and user identification or any other suitable information may be confirmed and returned to RI subsystem 100a. For medications that require greater security, fingerprint verification and/or any other user detection techniques may be used.

RI subsystem 100a may be configured to interact with end users primarily via voice recognition and processing. In the event that RI subsystem 100a cannot understand a user's vocal commands, the end user may be provided with the ability to enter commands on touchscreen 130 or via any other suitable input component of RI subsystem 100a. Voice interactivity may also include the ability for RI subsystem 100a to respond to a user's healthcare questions. The content for this capability may be sourced from any suitable (e.g., publicly available or privately maintained) health information databases and third-party healthcare artificial intelligence providers (e.g., any suitable TPE subsystem or data repository maintained by HMS subsystem 10 itself). Any operating system or accessible application (e.g., data structure 119) of RI subsystem 100a may provide several other core capabilities. For example, RI subsystem 100a may be configured to track an end user's medication schedule to issue voice reminders and dispense medications. In the event of a missed dose, RI subsystem 100a may be operative to alert the end user (e.g., via one or more associated end user subsystems) and/or one or more user caretakers (e.g., via one or more user caretaker subsystems) via any suitable communication techniques (e.g., via text message and/or mobile app notifications and/or the like). RI subsystem 100a may be configured to reorder automatically medications from the user's doctor or pharmacy seven days or any other suitable duration of time before they run out (e.g., before container 160 retains no more of such medication). At an end user's request, RI subsystem 100a can export medication adherence reports via e-mail or any other suitable technique to both caretakers and physicians and/or other suitable interested parties. Any suitable data may be communicated from RI subsystem 100a to HMS subsystem 10 that may be operative to maintain a database of information associated with any one or more end users, and such information may be requested or otherwise accessed from HMS subsystem 10 by any suitable user or caretaker subsystem using any suitable log-in credentials with HMS subsystem 10.

As RI subsystem 100a may operate with an open software platform, third party developers may be enabled to develop add-on services that may include, but are not limited to, connecting users to doctors on telemedicine services, hosting weight management programs, and linking to third party wearables and diagnostic devices.

RI subsystem 100a may also be accompanied by a mobile application for reminders and notifications while an end user is away from home (e.g., an application or data structure of an end user subsystem that may be in communication with RI subsystem 100a (e.g., directly or via HMS subsystem 10)). Designated caretakers of various caretaker subsystem can also use such an application (e.g., an application or data structure of a user caretaker subsystem that may be in communication with RI subsystem 100a (e.g., directly or via HMS subsystem 10)) to receive alerts and monitor the adherence rates of users. Medication information and schedules can also be entered via such a mobile application instead of onto RI subsystem 100a directly.

Description of FIGS. 13-18

Figure 13:
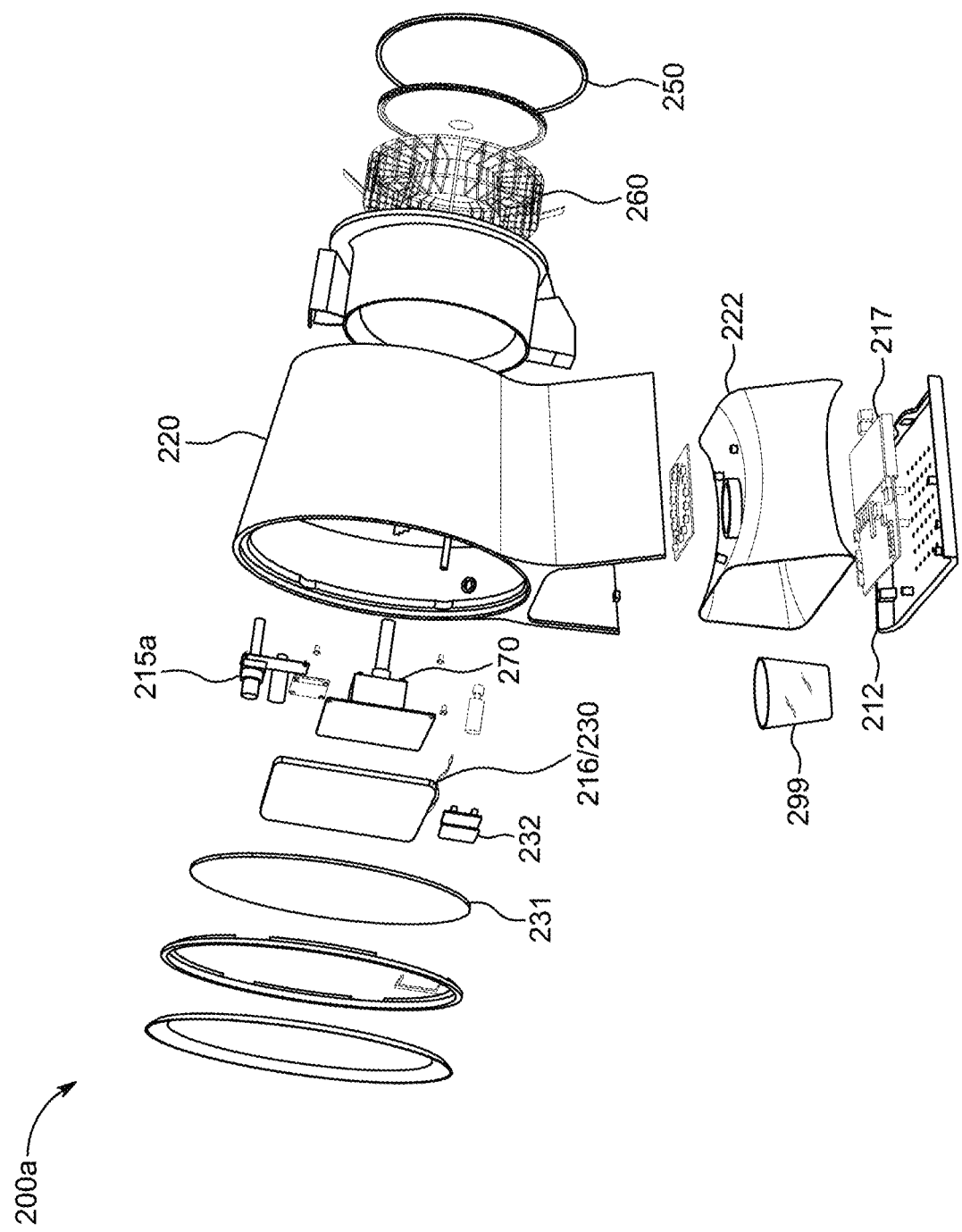
FIGS. 13-18 are various views of another robotic interface subsystem of the system of FIG. 1.
Figure 14:
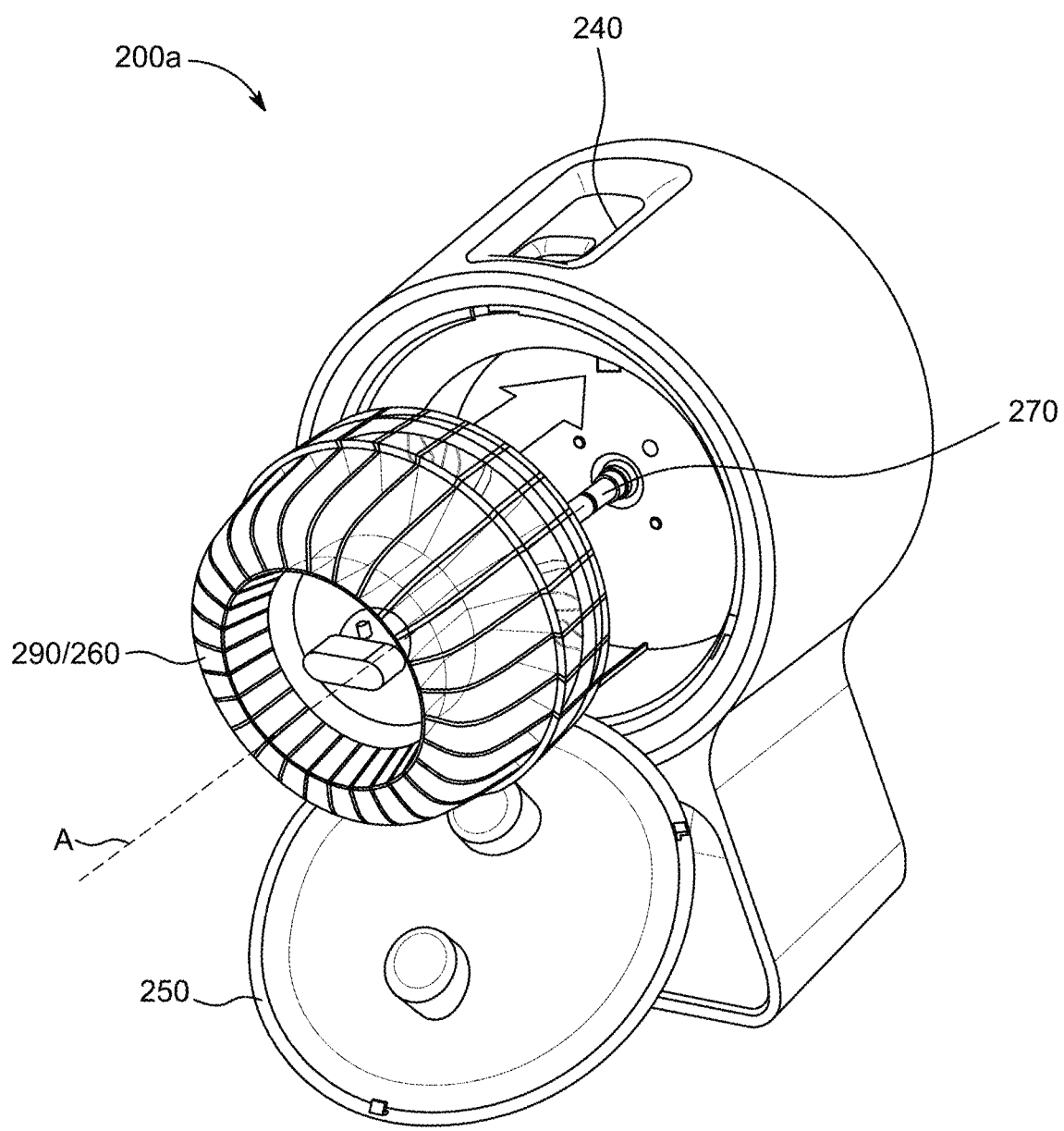
Figure 15:
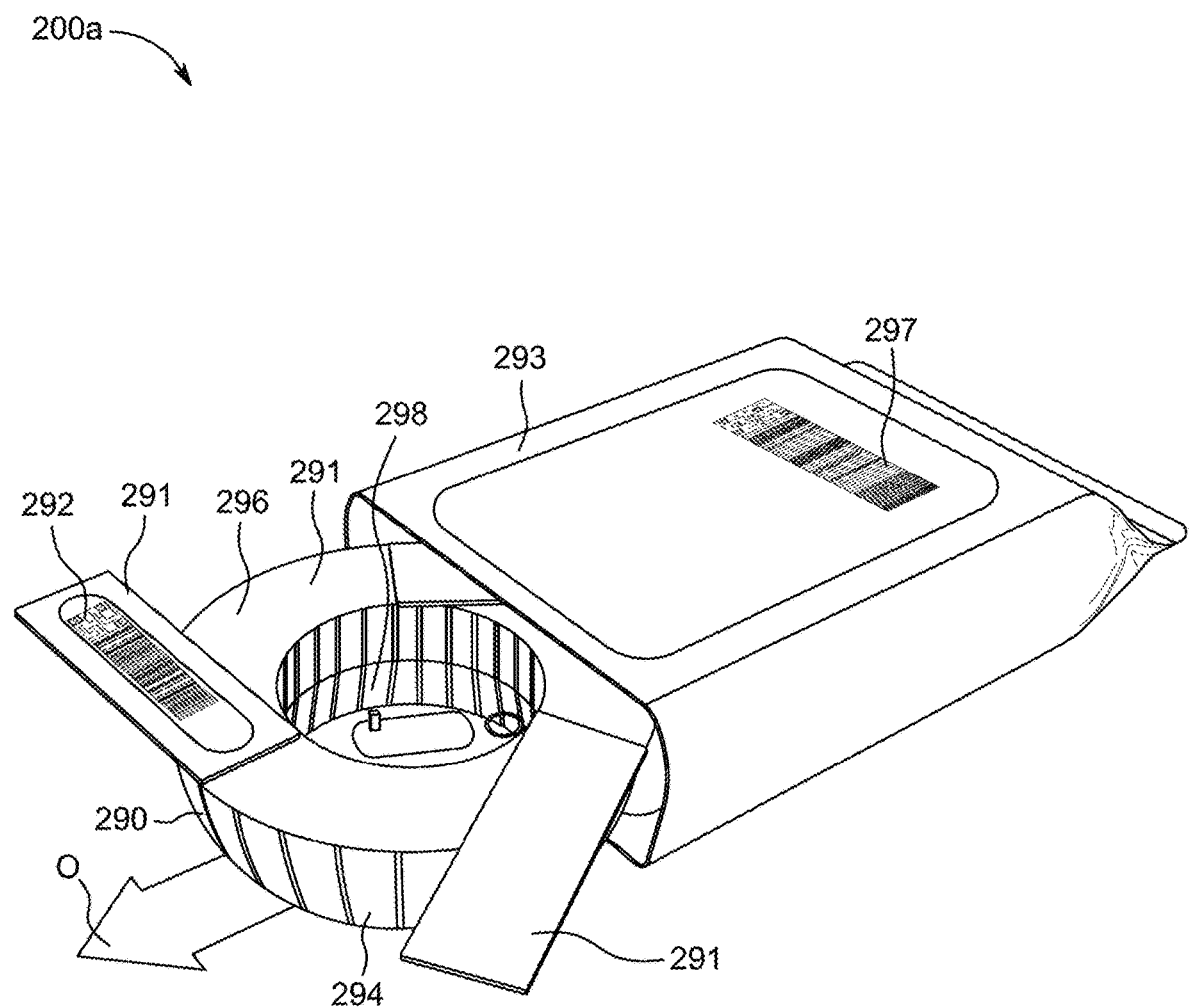

As shown in FIGS. 13-18, another illustrative robotic interface subsystem 200a may be provided with at least certain hardware and may be configured to function as a healthcare companion for an end user. RI subsystem 200a of FIGS. 13-18 may be similar to RI subsystem 100a of FIGS. 1-12, except as otherwise noted, where each element labelled with a 1XX of FIGS. 1-12 may be similar to an element labelled with a 2XX of FIGS. 13-18. For example, as shown in FIGS. 13 and 14, robotic interface subsystem 200a may be provided with at least certain hardware and may be configured to function as a healthcare companion for an end user. RI subsystem 200a may be configured to include the capability to store medications and dispense medications according to any suitable schedule accessible to RI subsystem 200a (e.g., a schedule that an end user may manually input into RI subsystem 200a via an I/O component 216 of RI subsystem 200a and/or a schedule that may be loaded onto RI subsystem 200a from a remote source (e.g., HMS subsystem 10 and/or any other suitable subsystem of system 1). A main body 220 of RI subsystem 200a may feature curved edges and/or a high quality glossy finish. The form factor may represent an anthropomorphic assistant with a face on a circular or any other suitably shaped screen 230. Screen 230 may be provided as a portion of a touchscreen or non-touchscreen I/O component 216 of RI subsystem 200a and may include a cover 231 and circuitry 232. For example, such a touchscreen may be exposed at a front of a circular portion of main body 220. On top of main body 220 may be a hatch 240 that may be configured to automatically open for enabling one or more internal compartments within main body 220 to be filled with medication or any other suitable content. For example, hatch 240 may be controlled by one or more motors that may be operative to open or close hatch 240 when appropriate, such as when a load operation is appropriate. A load operation may trigger when a user interacts with RI subsystem 100a to load a medication or other material into an internal compartment, such that a container 260 may be rotated or otherwise moved to align a compartment with hatch 240, and then RI subsystem 200a may be operative to open hatch 240 and instruct the user to load any suitable amount of material (e.g., one dose of medication) therein, after which container 260 may be rotated or otherwise moved to align another compartment with hatch 240 to repeat the process as appropriate. Hatch 240 may be closed once the filling process has been completed. On a bottom or downwardly facing surface of main body 220 may be a second hatch that may be configured to open for dispensing content (e.g., medications) from the internal compartment(s) of main body 220 for retrieval by an end user (e.g., into a receptacle 299 (e.g., drinking glass) that may be positioned underneath the second hatch to receive contents from the compartment of main body 220 via the second hatch and that may then be held and moved by an end user away from RI subsystem 200a for use of the contents). One or more sensors (e.g., capacitive and/or near-field communication ("NFC") sensor(s)) may be provided to determine if a particular container (e.g., a glass receptacle or a plastic receptacle or no receptacle) is positioned adjacent the second or dispensing hatch. One or more pill overfull sensors (e.g., an IR sensor or a camera) may be provided by RI subsystem 200a (e.g., positioned at or near the top of hatch 240) to detect when pills or other material have been loaded and/or to determine if the compartment is full or nearing capacity or is almost empty or completely empty.

A back of main body 220 may include a cover 250 that may allow access to the internal receptacle(s) (e.g., medication container(s)) within main body 220). Cover 250 may be configured to be removed for enabling access to the internal receptacle(s) only upon user authentication via fingerprint verification or any other suitable authentication (e.g., using any suitable sensor of subsystem 200a), such that the contents may be protected from people other than the appropriate end user (e.g., meddling children or a thieves). For example, external-facing screws (not shown) may require a proprietary screwdriver to be removed from cover 250 and main body 220, ensuring the security of the internal contents of the internal receptacle(s) of main body 220.

Main body 220 may at least partially enclose or support an ARM-based mobile processor 212 (e.g., on a printed circuit board), an LCD touchscreen 230 of I/O component 216 (e.g., a high definition touchscreen display), external camera sensor 215a, at least one microphone sensor (e.g., one or two omnidirectional microphones), at least one speaker I/O component (e.g., tweeter and subwoofer), any suitable wireless communication adapters (e.g., a Wi-Fi transceiver and a Bluetooth transceiver). One or more light emitting I/O components (e.g., mood lights) may be provided adjacent the dispensing hatch for illuminating the space at which contents may be released from main body 220 for an end user. One or more motion sensors and/or image or camera sensors may be provided by a respective hatch to detect filling and dispensing of contents with respect to the internal receptacle(s) of main body 220.

The internal receptacle(s) of main body 220 may be provided by any suitable container 260 (e.g., a removable antibacterial medicine container). As shown, container 260 may be provided as a circular container of any suitable material (e.g., plastic) with a central spoke opening for motorized rotation about an axis A by any suitable motor 270 that may be positioned at least partially within or supported by main body 220. Container 260 may be subdivided to include any suitable number (e.g., 28 or 31) of compartments 264 in a circumferential manner. Each compartment 264 may be sized to receive and retain at least one dose of at least one medication for an end user. Container 260 may be covered by a cover that may be removable (along with or independently of cover 250) from container 260 to facilitate visualization of some or all compartments 264 for enabling cleaning of compartments 264 and/or manual loading of contents by an end user into compartments 264. On the circumference of container 260, each small compartment 264 may feature a spring-loaded door 266 that may be operative to open to expose an opening into its respective compartment 264 when that compartment 264 and door 266 is aligned with either hatch 240 for filling compartment 264 with contents or the dispensing hatch for dispensing contents from compartment 264 and main body 220 (e.g., into receptacle 299). Motor 270 may rotate container 260 about axis A under the control of a microcontroller that may separate from a primary processor of RI subsystem 200a. When a compartment 264 and door 266 may be aligned with hatch 240, material (e.g., medication (e.g., a single dose)) may be inserted into hatch 240 and compartment 264 by the user. A stop (e.g., a mechanical limit stop) may be provided and used to reset a motor to a zero position and/or to limit the movement of a mechanism (e.g., a mechanical rocker) that may be configured to open door 266 (e.g., a spring-loaded door). A motor may be operative to move such a mechanism to open one or more doors 266, while another mechanism may be any suitable support (e.g., mechanical support) for the motor.

In some embodiments, rather than manually loading content into compartments 264 of container 260 (e.g., via hatch 240), a pre-sealed and/or disposable tray 290 that may include multiple compartments 294, one or more of which may be pre-filled with medication (not shown), may be shipped in a package 293 to the patient. Package 293 may be a sealed pouch, which may be airtight to protect the content of tray 290 during shipment and until use. The user may open package 293 (e.g., with a tear away pull tab) and may remove tray 290 from package 293 (e.g., in the direction of arrow O of FIG. 15). Then, the user may scan a barcode 292 provided on tray 290 and/or on its package 293 (e.g., using any suitable scanner of RI subsystem 200a or any other suitable scanner of system 1 (e.g., using an end user subsystem)), where such a scanned barcode or other suitable information source may provide information to the HMSP about the content of tray 290 and may share information with HMS subsystem 10 (e.g., that the user received the tray 290). Tray 290 may be made of any suitable material, such as a clear plastic, such that a user may see its content. In some embodiments, tray 290 may be vacuum-formed and/or injection molded. A front side of tray 290 may be provided with a covering 296 that may cover an opening to each one of compartments 294 for preventing the content of compartments 294 from falling out of tray 290. Covering 296 may be any suitable material, such as a think membrane material (e.g., tear-proof paper or tear-proof plastic, which may be transparent), and may be coupled to tray 290 in any suitable manner, such as by heat sealing or glue. Covering 296 may be a thermal sealed printable sheet with indicia identifying the content of each compartment 294 it covers.

Figure 16:
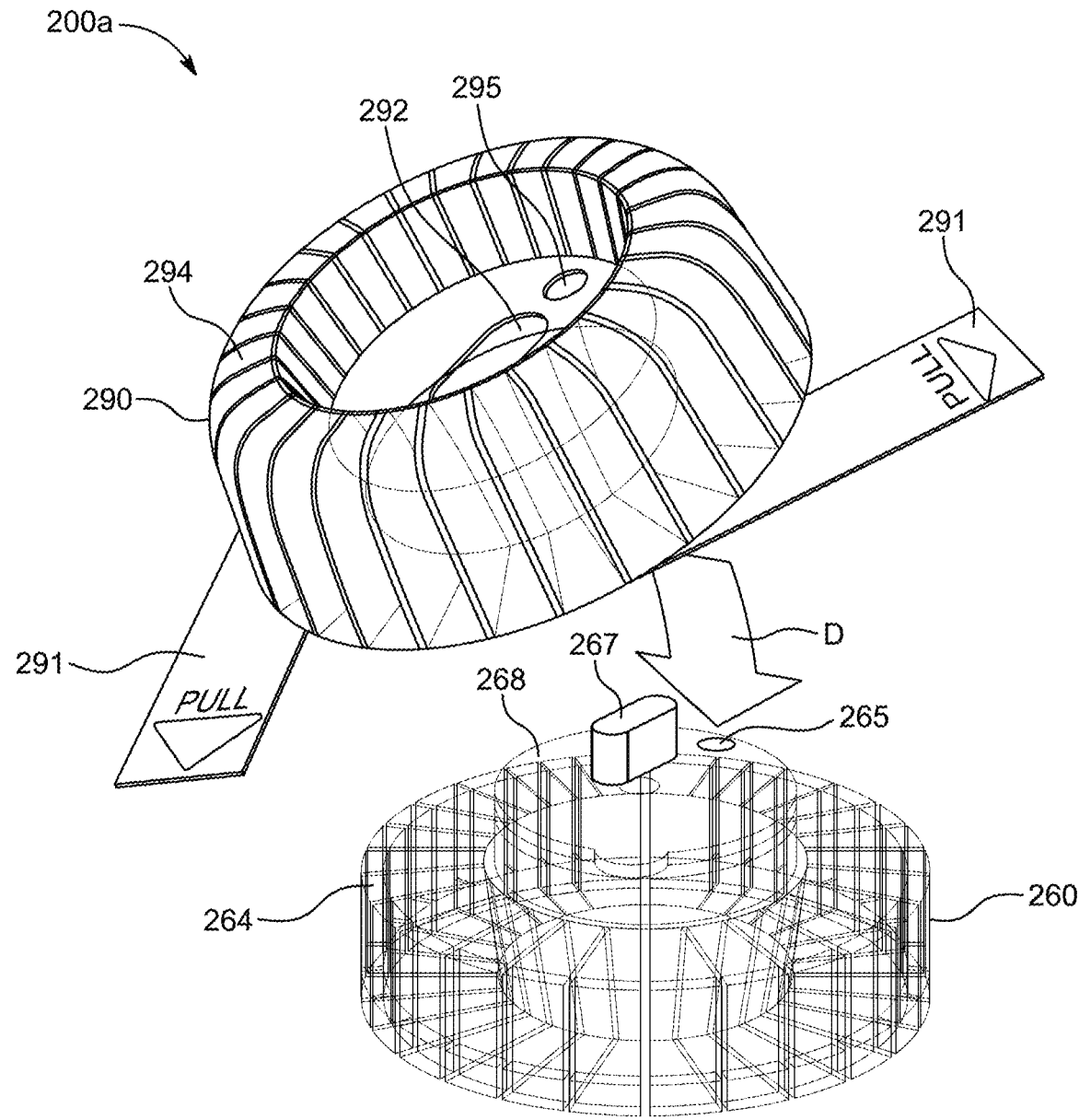
Figure 17:
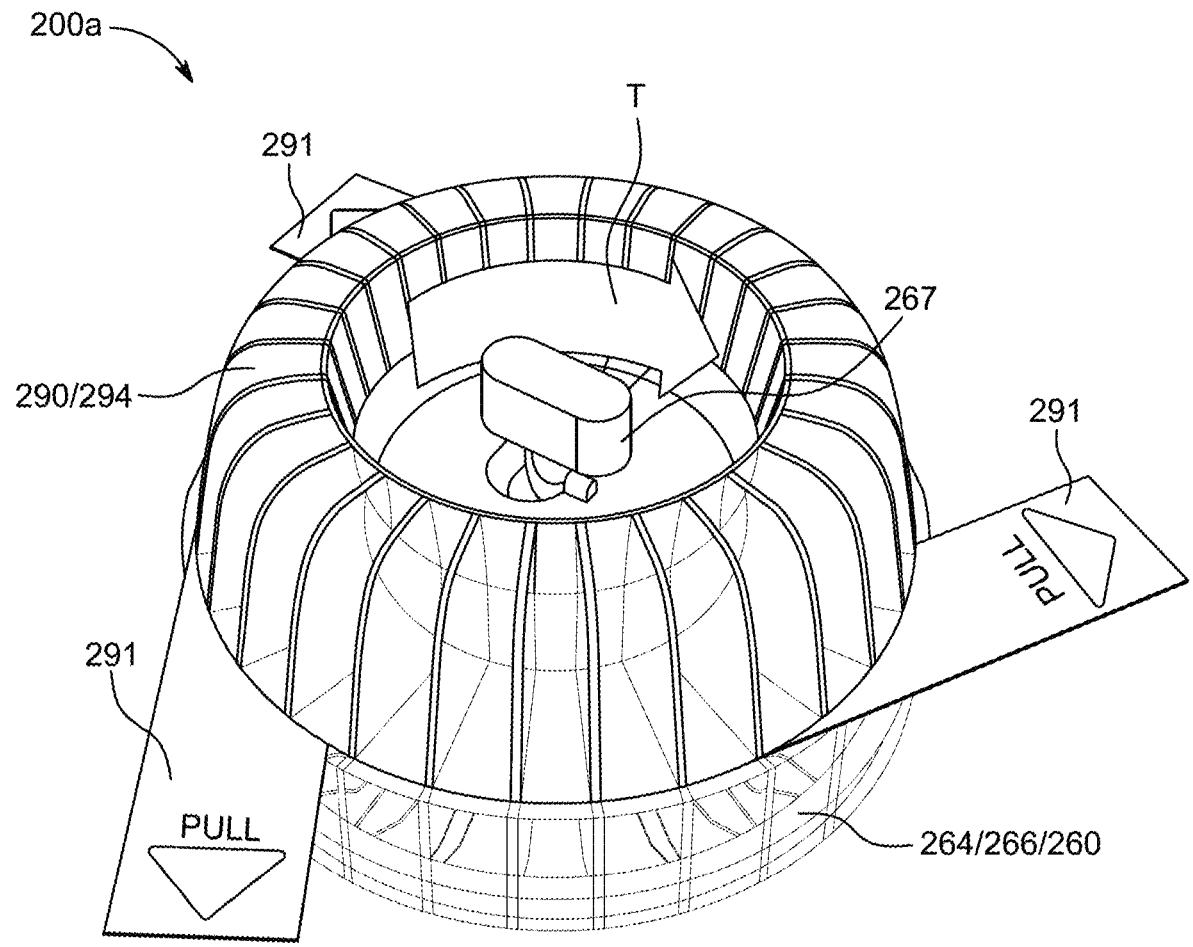
Figure 18:
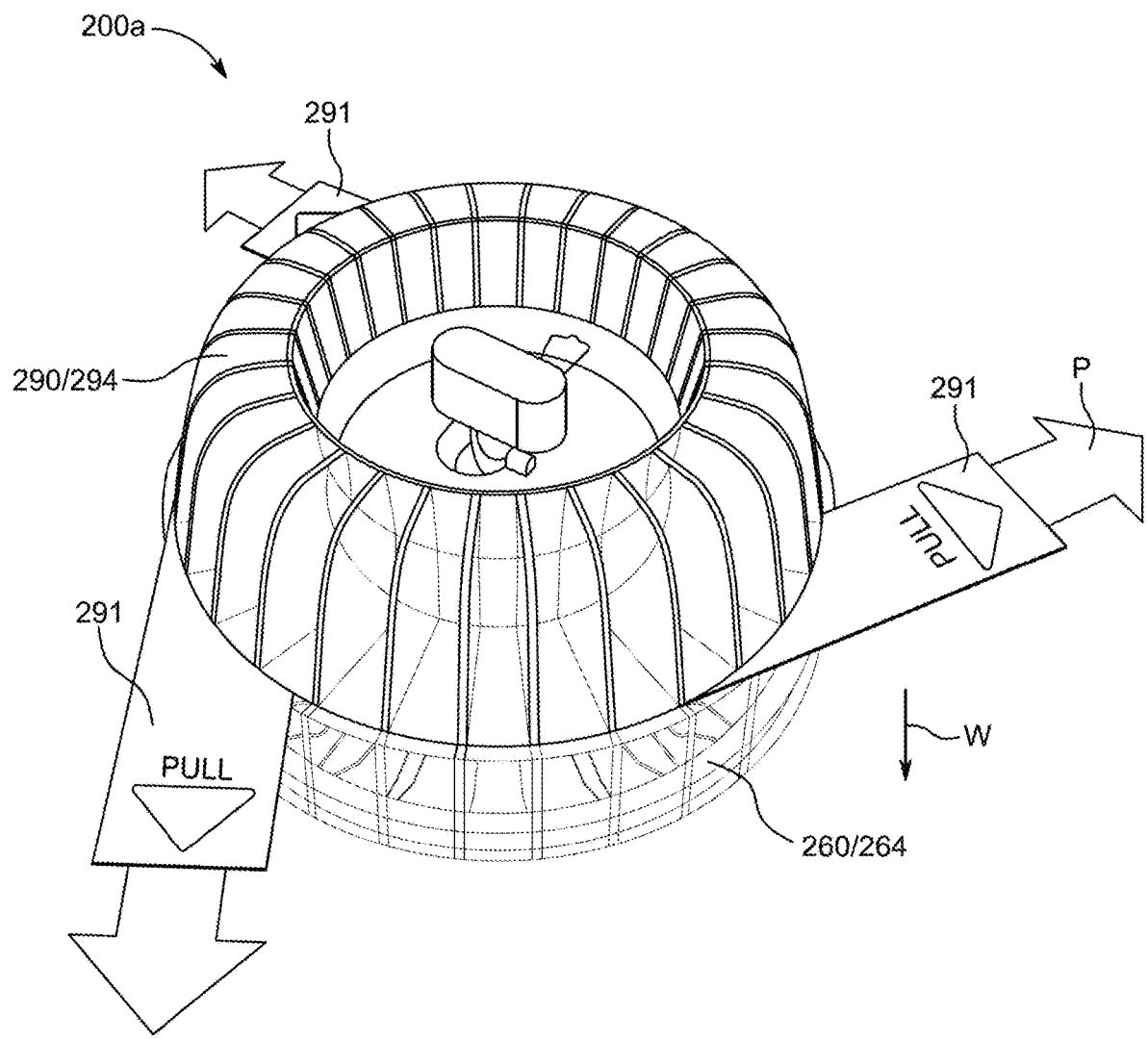

While covering 296 is still coupled to tray 290, the user can then couple tray 290 to container 260, such as by laying the front side of tray 290 with covering 296 in the downward direction of arrow D of FIG. 16 onto a back side of container 260 that may have no covering surface, thereby exposing the open space of each compartment 264, such that covering 296 prevents the content of compartments 294 of tray 290 from falling into the exposed compartments 264 of container 260. Tray 290 and container 260 may each have respective features that may allow tray 290 to be coupled to container 260 in one particular orientation, such that one particular compartment 294 of tray 290 may align with one particular compartment 264 of container 260 (e.g., tray 290 may be keyed to container 260 in a specific manner prior to depositing the content of tray 290 into container 260). For example, as shown, a projection 268 may extend upward away from the back side of container 260 and into a recess 298 within the front surface of tray 290, where projection 268 and recess 298 may each be round to align container 260 and tray 290 within certain degrees of freedom but may still enable rotation of container 260 with respect to tray 290. However, as also shown, a projection 265 may extend upward away from projection 268 of container 260 and into a recess 295 at a surface of recess 298 of tray 290, where the interaction of projection 265 into recess 295 combined with the interaction of projection 268 within recess 298 may prevent rotation of container 260 with respect to tray 290 but instead may require a specific compartment 294 of tray 290 to align with a specific compartment 264 of container 260, which may ensure a desired disposal of content from tray 290 into desired compartments 264 of container 260. Moreover, as shown in FIG. 17, a knob 267 may extend upward away from projection 268 of container 260 and through a recess 292 at a surface of recess 298 of tray 290, and then, knob 267 may be rotated (e.g., 90°) in the direction of arrow T of FIG. 17 to clamp tray 290 to container 260 in the desired alignment created by projection 265/recess 295 and projection 268/recess 298. Such rotation of knob 267 to the orientation of FIG. 17 may snap or otherwise click into place (e.g., visually, tactilely, and/or audibly) and may resist being re-oriented, such that container 260 may be held against tray 290. Next, covering 296 may be safely removed from between tray 290 and container 260, such that the content of compartments 294 of tray 290 may fall down freely (e.g., in the direction of arrow W) into the appropriate compartments 264 of container 260. As shown, covering 296 may include one or more pull tabs, such as three pull tabs 291 spaced about and coupled to covering 296, that may extend outwardly from tray 290 such that they may each be grabbed and pulled by a user in the direction of arrows P of FIG. 18 for removing covering 296 from within the thin space between container 260 and tray 290. This system may always ensure that the medication is covered within tray 290, such that they can't be accidentally spilled, until tray 290 is properly aligned with and clamped to container 260. Then, as shown in FIG. 14, the combination of container 260 and tray 290 may be inserted into body 220 of RI subsystem 200a for distributing the content of compartments 264 to the user's receptacle 299 (e.g., a central spoke opening in a front side of container 260 may be slid along axis A over an axle of motor 270 for being rotated about axis A. Alternatively, tray 290 may then be unclamped from container 260 and a cover may be clamped onto container 260 before being inserted into body 220, while tray 290 may be disposed of or returned to its source for re-use.

Main body 220 of RI subsystem 200a may be perched on a stand 222 that may permit receptacle 299 to be positioned under main body 220 for catching any contents dispensed from any compartment 264 of container 260. Directly above receptacle 299 may be one or more light emitting I/O components (e.g., mood lights) for illuminating the space at which contents may be released from main body 220 for an end user (e.g., for illuminating receptacle 299 when it contains medications). For example, one or more light emitting I/O components 216c may be turned on independently of the presence or absence of material (e.g., medications) inside receptacle 299, but instead one or more light emitting I/O components 216c may be turned on when RI subsystem 200a determines that a user's attention ought to be attracted to RI subsystem 200a for reminding the user to access certain material (e.g., certain medication). RI subsystem 200a may be configured to determine whether the appropriate material has been dispensed into receptacle 299 and/or whether receptacle 299 has been removed from the position to receive material from RI subsystem 200a (e.g., using any suitable sensor(s), such as one or more capacitive and/or NFC sensors). Once it has been detected that a user has removed a receptacle in which material had been dispensed, one or more light emitting I/O components may be turned off. RI subsystem 200a may also include one or more suitable user authentication sensors (e.g., a fingerprint scanner sensor or any other suitable biometric sensor(s)) for added security, as noted above, that may require an appropriate end user be detected before any contents from container 260 may be released from main body 220 (e.g., into receptacle 299). Stand 222 may at least partially protect or support a power supply 217 of RI subsystem 200a (e.g., a wired power supply (e.g., via power cable 217a) and a lithium-ion battery that may assures all basic functions of RI subsystem 200a remain active in the event of a power outage). Immediately below or adjacent a side of a properly positioned receptacle 299 there may be provided at least one sensor that may be built into or otherwise supported by stand 222. For example, a first sensor may be a capacitive sensor that may be operative to detect the presence of any receptacle 299 under the dispensing hatch, while a second sensor may be a radio frequency identification ("RFID") or NFC sensor that may be operative to read a specific RFID or NFC tag of receptacle 299 (e.g., to determine the type of receptacle and the owner of the receptacle). A user may be provided with two or more particularly tagged receptacles 299 (e.g., a glass receptacle for home use and a plastic receptacle for travel) that may be associated by the HMSP with the particular user and particular biometrics of the user that may detected by sensor(s) or otherwise in conjunction with the data received by sensor(s) to confirm authentication of a particular end user prior to dispensing contents (e.g., medication) from the dispensing hatch. Two independent microcontrollers may verify the biometric data detected by the sensor(s) and synthesize such data with any receptacle data detected by the sensor(s). RI subsystem 200a may be configured to detect the presence of receptacle 299 utilizing any suitable methods, including, but not limited to, near field communication and capacitive sensing. For example, a tag may be embedded in (e.g., in the bottom of) or otherwise coupled to receptacle 299. Any suitable component (e.g., concentric copper tracks on the base of stand 222) may be operative to detect the presence of a specific receptacle 299 with all accompanying information, such as type of receptacle (e.g., plastic to-go receptacle or glass home-use receptacle) and owner of the receptacle (e.g., a particular user of potentially multiple users of the system). Alternatively, no tag may be coupled to receptacle 299. Instead, detection of receptacle 299 may be accomplished by RI subsystem 200a monitoring the capacitance between a component (e.g., one or more copper tracks on the base of stand 222). For the purpose of detecting receptacle 299, an integrated system with concentric copper tracks on the base of stand 222 can either function as an antenna for specific tags or as a capacitive sensor. Commutation between the two functions may either be electro-mechanical (e.g., relay commutation) or solid state.

Any suitable data structure(s) of RI subsystem 200a may be accessible to RI subsystem 200a and used to drive RI subsystem 200a (e.g., a processor 112 of RI subsystem 200a). For example, any suitable data structure(s) of RI subsystem 200a may be a firmware or software application operating system based on a customized platform (e.g., of an Android and/or iOS platform). Key functionalities of such an application may be interactivity, reliability, safety, and/or versatility. Such an application may enable RI subsystem 200a to interact with an end user via an anthropomorphic persona of RI subsystem 200a. Such a persona may include two eyes that express human emotion and a mouth (e.g., features of a face) that may mirror movements associated with human speech indicative of audible information presented by any speaker I/O component of RI subsystem 200a. For example, RI subsystem 200a may be configured to better address the social and emotional needs of a user because RI subsystem 200a may integrate information from its programmed schedule, camera, microphone, cloud based medication database, and/or any other available features to interact with the user proactively. For example, if a particular medication has a common side effect, RI subsystem 200a may be configured to inquire whether the user is experiencing the side effect. In addition, RI subsystem 200a may be configured to be fully responsive to voice inquiries and/or commands of the user. RI subsystem 200a, therefore, may be operative to answer health-related questions and recommend a telehealth visit if RI subsystem 200a cannot provide a satisfactory answer.

RI subsystem 200a may be configured to be constantly aware of its surroundings. Using its camera(s) and/or microphone(s) and/or any other suitable sensors, RI subsystem 200a may be configured to identify any particular end user of the HMSP as the user enters a detectable sphere of RI subsystem 200a. Upon user detection and identification, RI subsystem 200a may be configured to awaken (e.g., power certain other components of RI subsystem 200a) so as to be able to respond to end user commands, as necessary. Initial user identification by RI subsystem 200a may rely on facial recognition or any other suitable detection technique. RI subsystem 200a may be configured to detect faces in real-time. The image of a detected face may be uploaded or otherwise shared with a backend cloud server (e.g., HMS subsystem 10 and/or an appropriate TPE subsystem) that may process such an image for facial recognition purposes (e.g., against all known users of the HMSP or of that particular RI subsystem 200a) and user identification or any other suitable information may be confirmed and returned to RI subsystem 200a. For medications that require greater security, fingerprint verification and/or any other user detection techniques may be used.

RI subsystem 200a may be configured to interact with end users primarily via voice recognition and processing. In the event that RI subsystem 200a cannot understand a user's vocal commands, the end user may be provided with the ability to enter commands on touchscreen 230 or via any other suitable input component of RI subsystem 200a. Voice interactivity may also include the ability for RI subsystem 200a to respond to a user's healthcare questions. The content for this capability may be sourced from any suitable (e.g., publicly available or privately maintained) health information databases and third-party healthcare artificial intelligence providers (e.g., any suitable TPE subsystem or data repository maintained by HMS subsystem 10 itself). Any operating system or accessible application (e.g., data structure) of RI subsystem 200a may provide several other core capabilities. For example, RI subsystem 200a may be configured to track an end user's medication schedule to issue voice reminders and dispense medications. In the event of a missed dose, RI subsystem 200a may be operative to alert the end user (e.g., via one or more associated end user subsystems) and/or one or more user caretakers (e.g., via one or more user caretaker subsystems) via any suitable communication techniques (e.g., via text message and/or mobile app notifications and/or the like). RI subsystem 200a may be configured to reorder automatically medications from the user's doctor or pharmacy seven days or any other suitable duration of time before they run out (e.g., before container 260 retains no more of such medication). At an end user's request, RI subsystem 200a can export medication adherence reports via e-mail or any other suitable technique to both caretakers and physicians and/or other suitable interested parties. Any suitable data may be communicated from RI subsystem 200a to HMS subsystem 10 that may be operative to maintain a database of information associated with any one or more end users, and such information may be requested or otherwise accessed from HMS subsystem 10 by any suitable user or caretaker subsystem using any suitable log-in credentials with HMS subsystem 10.

As RI subsystem 200a may operate with an open software platform, third party developers may be enabled to develop add-on services that may include, but are not limited to, connecting users to doctors on telemedicine services, hosting weight management programs, and linking to third party wearables and diagnostic devices.

RI subsystem 200a may also be accompanied by a mobile application for reminders and notifications while an end user is away from home (e.g., an application or data structure of an end user subsystem that may be in communication with RI subsystem 200a (e.g., directly or via HMS subsystem 10)). Designated caretakers of various caretaker subsystem can also use such an application (e.g., an application or data structure of a user caretaker subsystem that may be in communication with RI subsystem 200a (e.g., directly or via HMS subsystem 10)) to receive alerts and monitor the adherence rates of users. Medication information and schedules can also be entered via such a mobile application instead of onto RI subsystem 200a directly.

Figure 19:
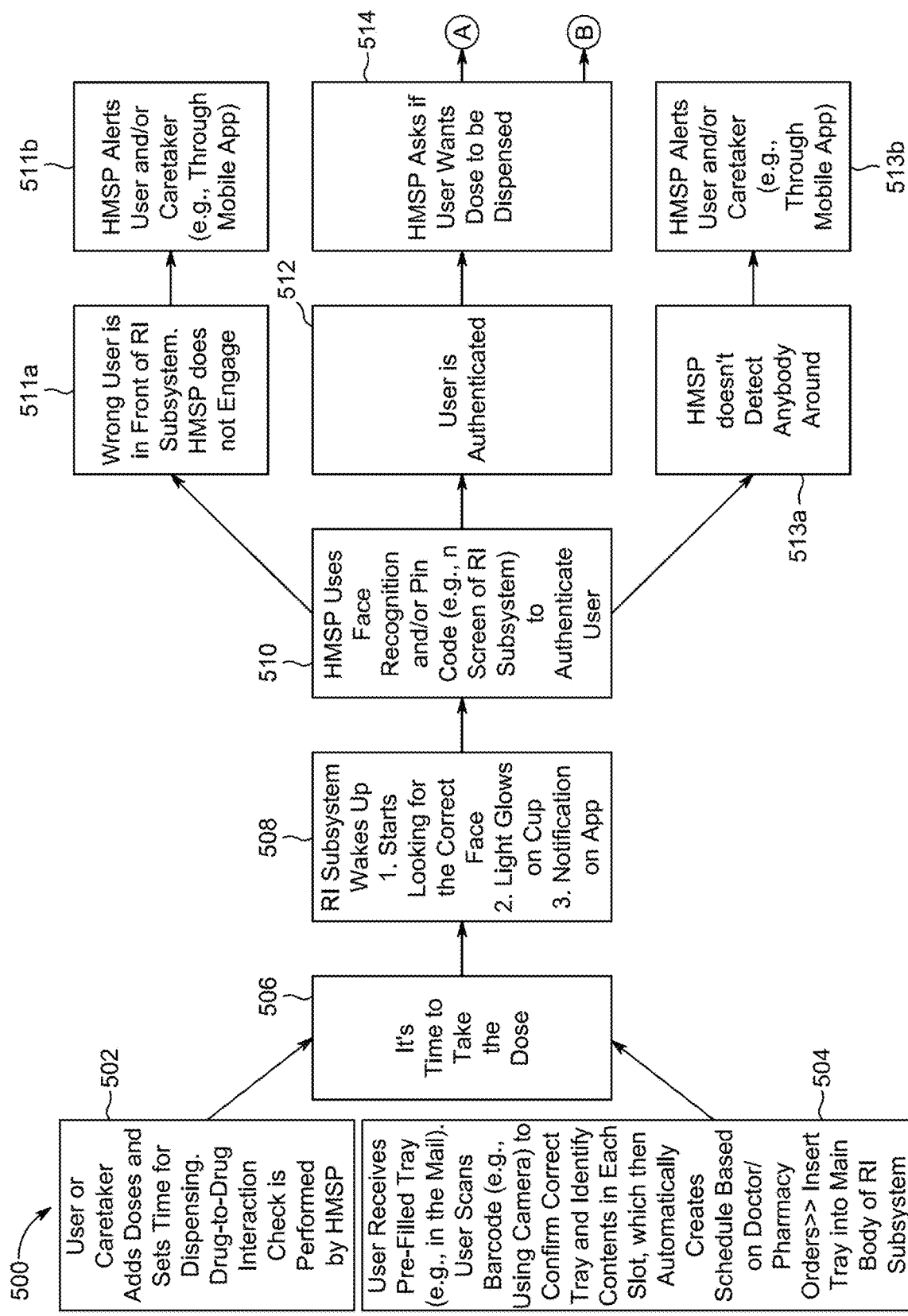
FIG. 19 is a flowchart of an illustrative process for providing a healthcare management service.
Figure 19:
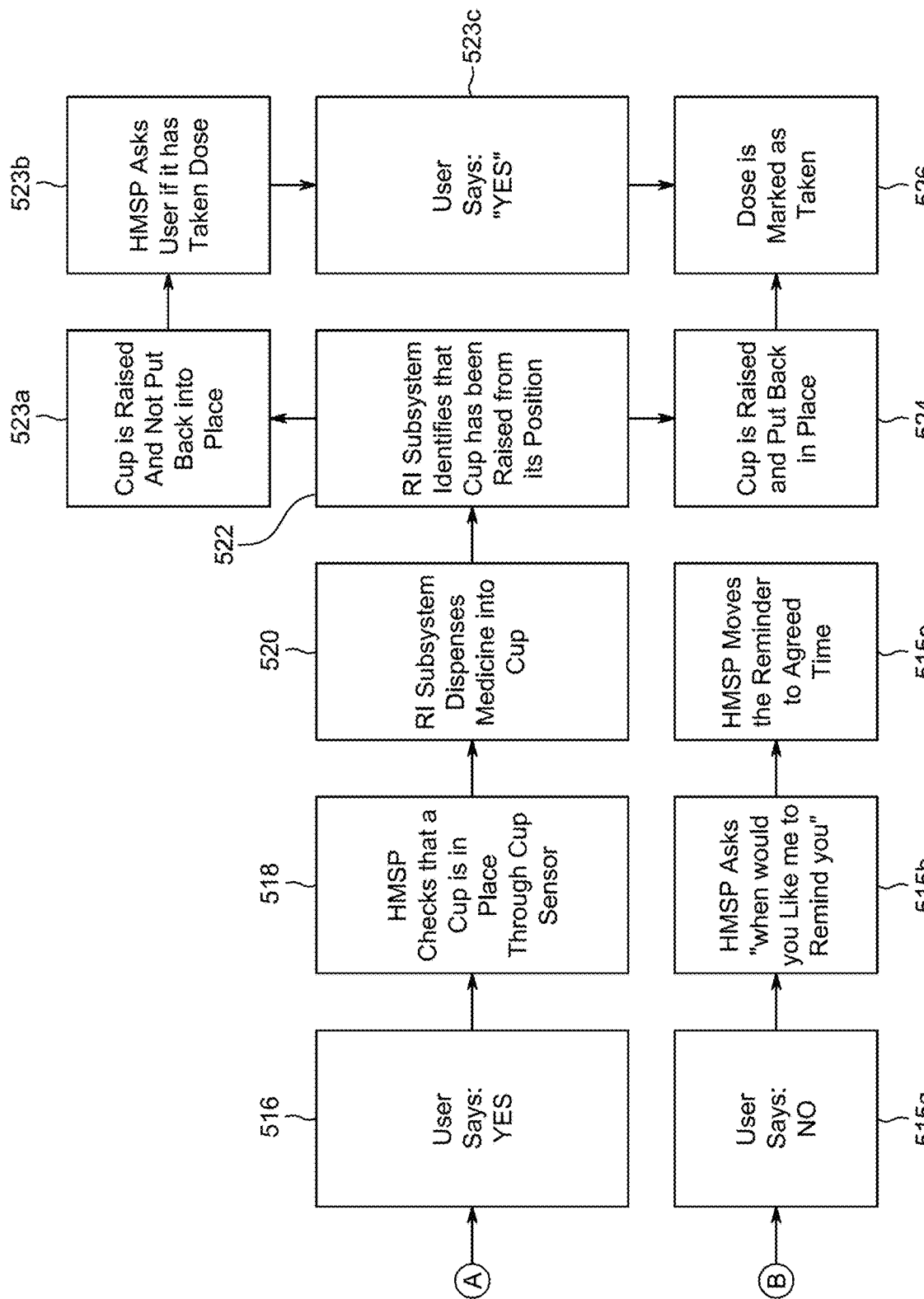
Figure 20:
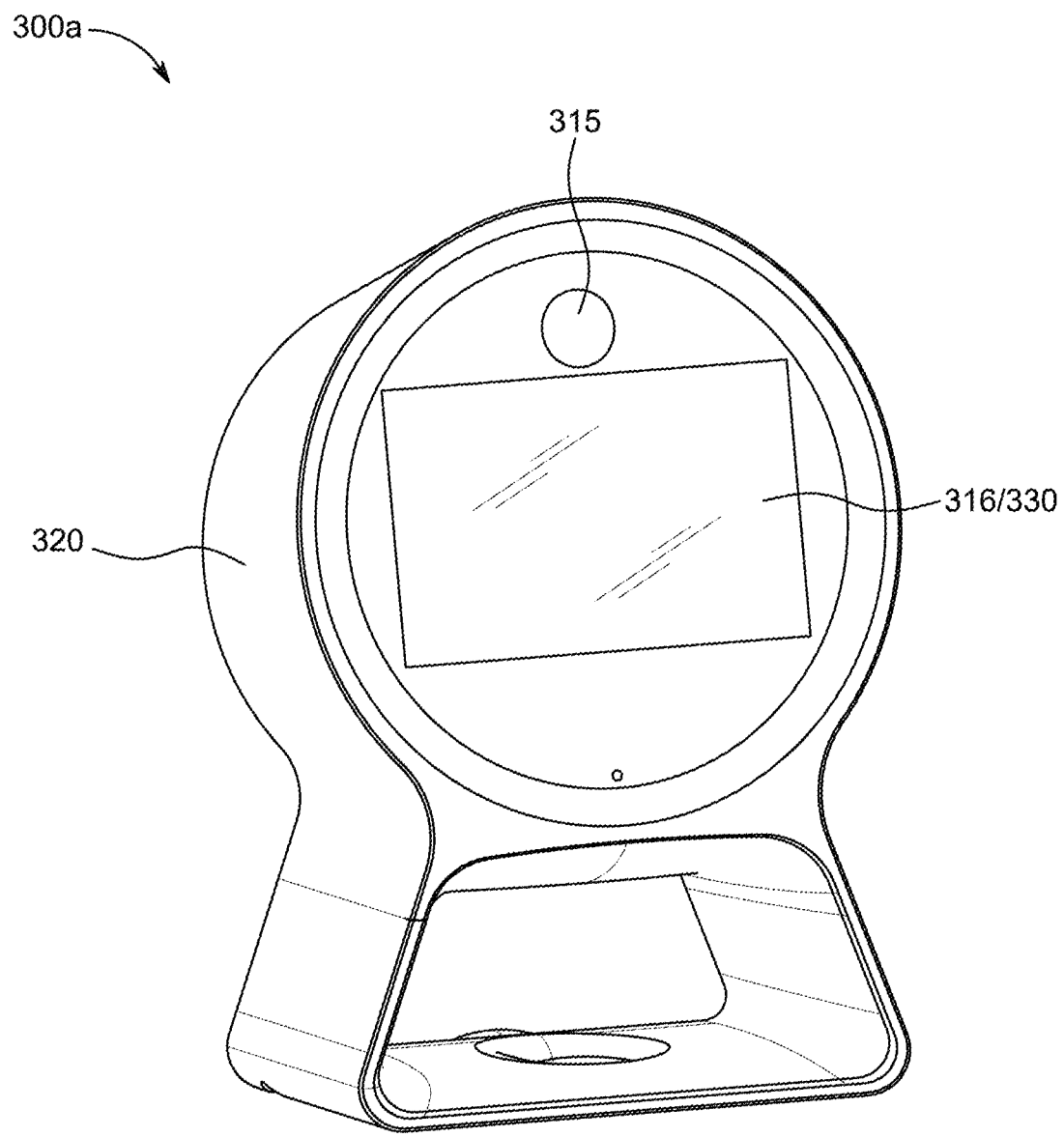
FIGS. 20-33, 34A-34D, and 35-38 are various views of another robotic interface subsystem of the system of FIG. 1.
Figure 21:
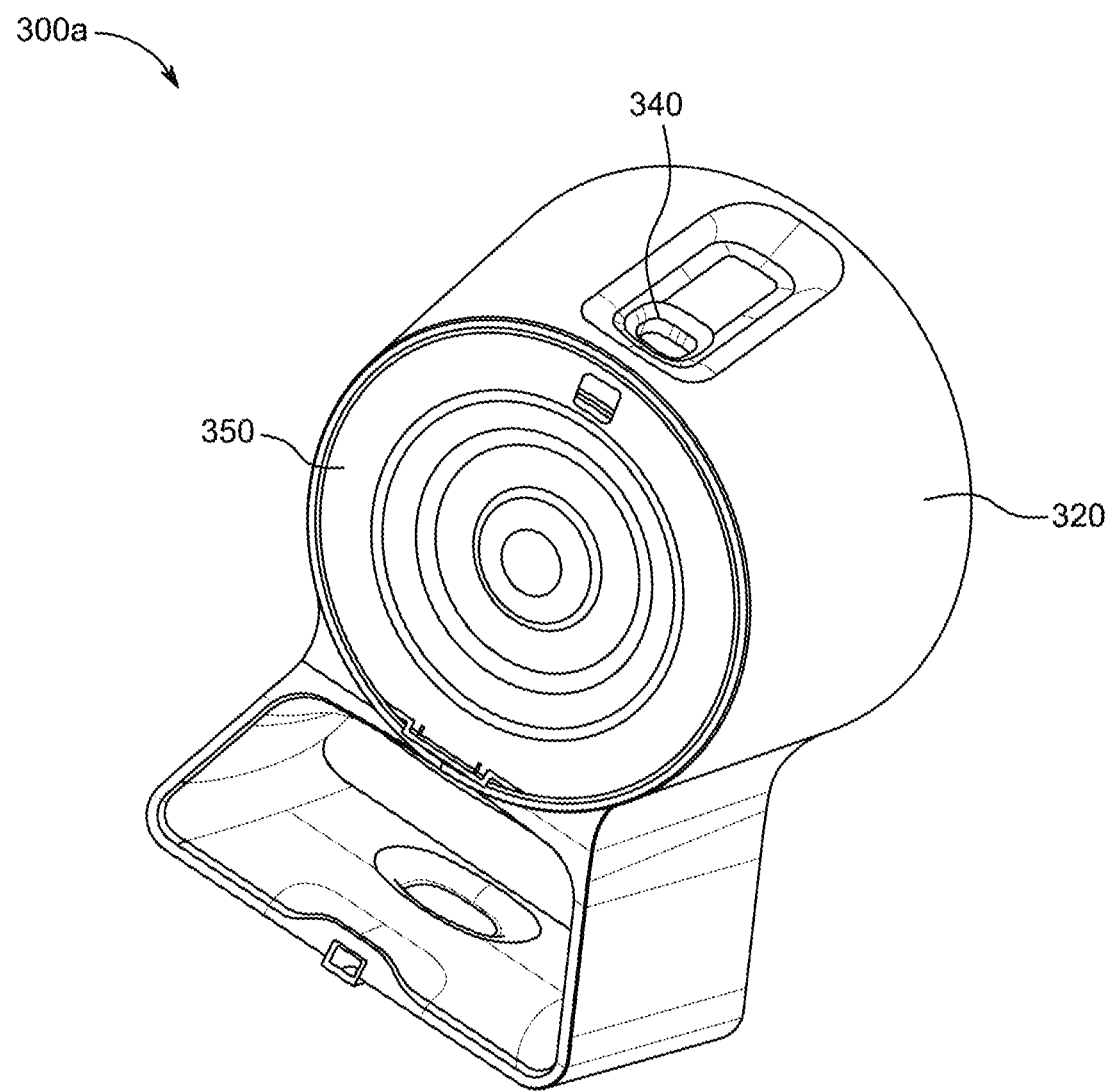
Figure 22:
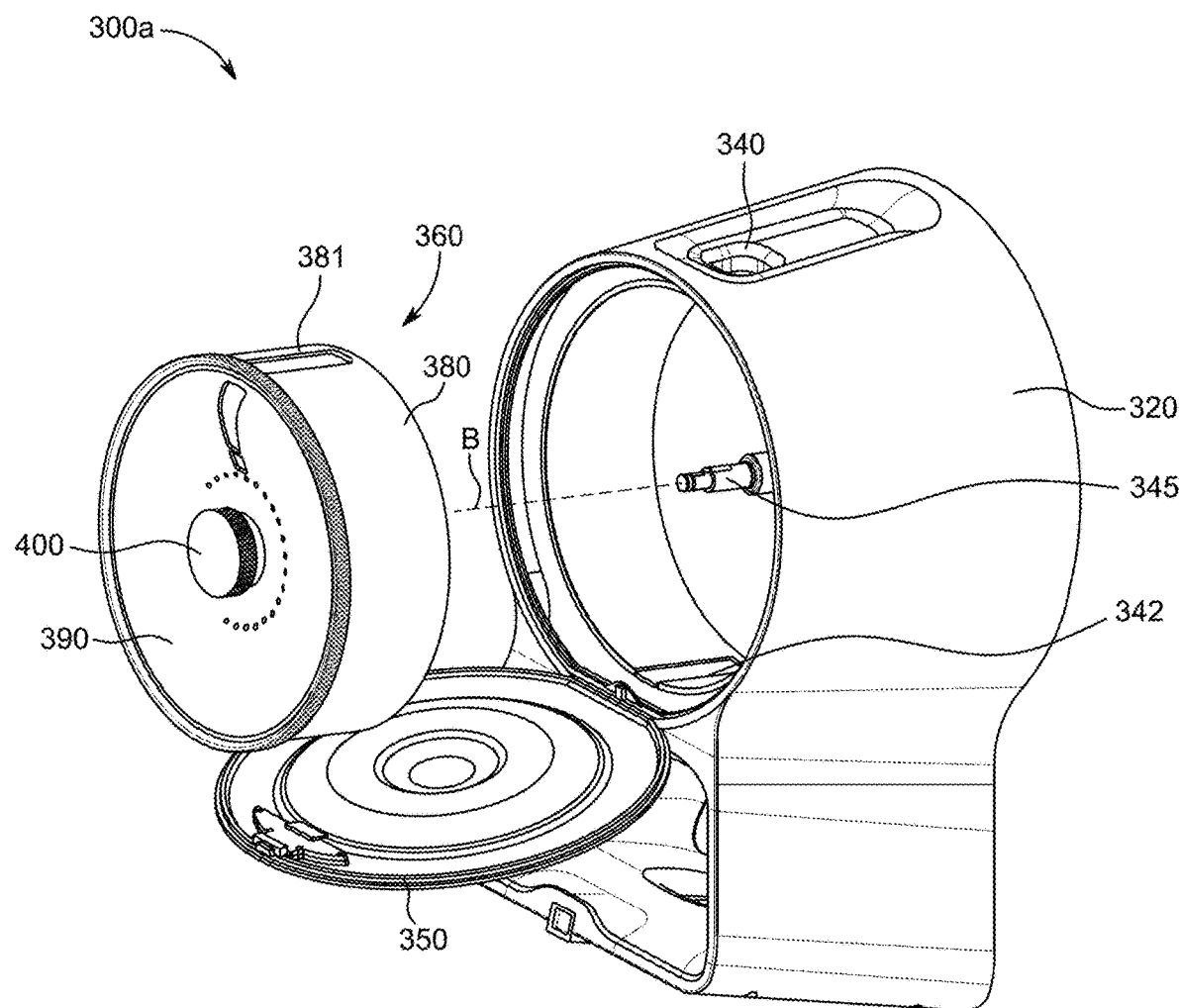
Figure 23:
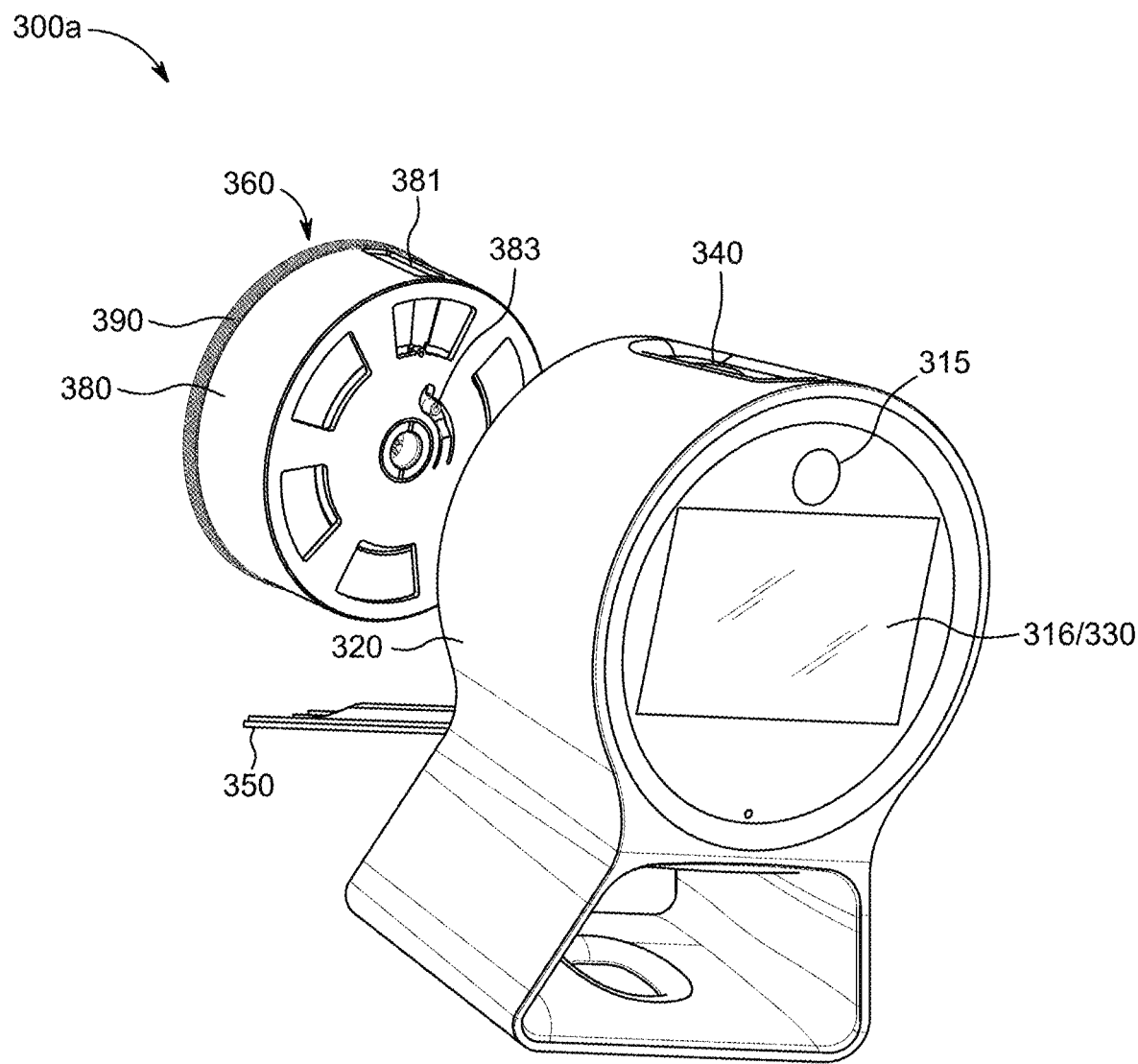
Figure 24:
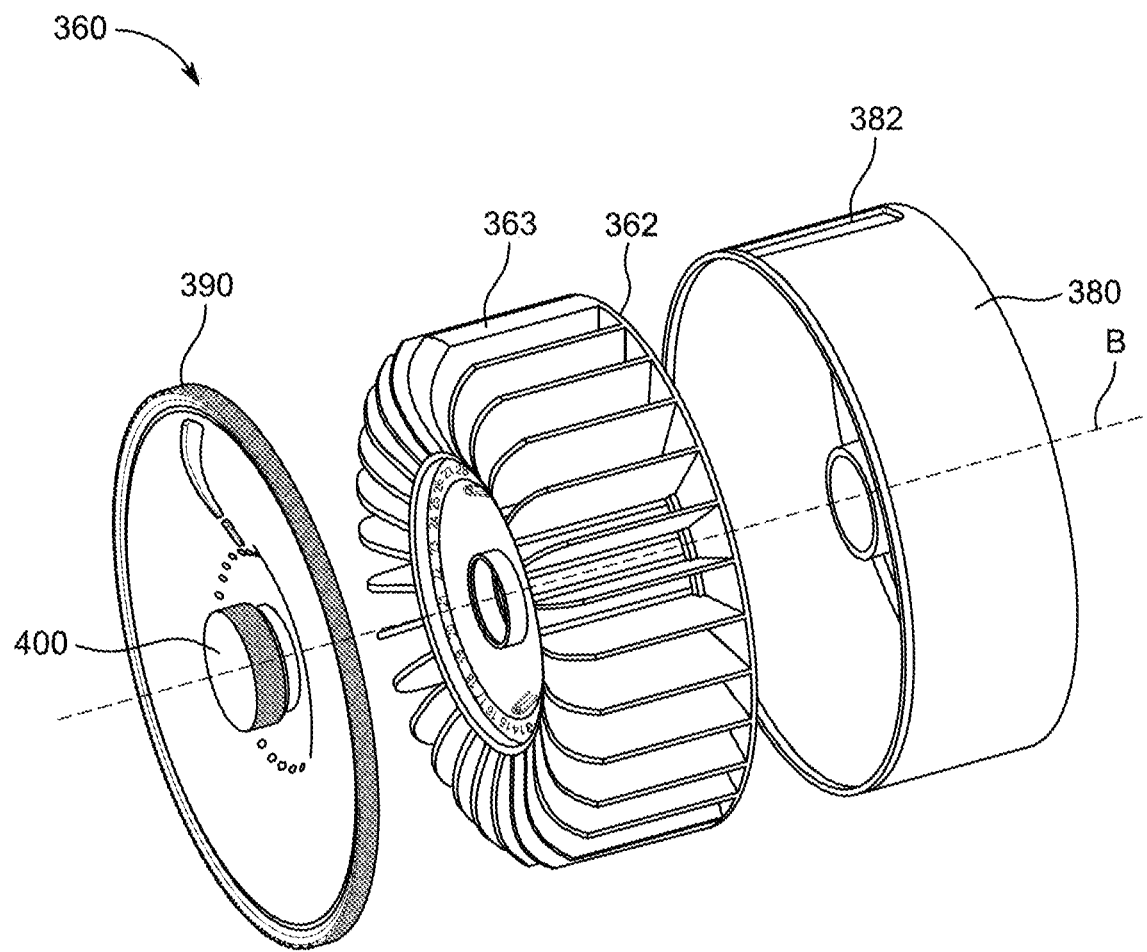

Description of FIG. 19

FIG. 19 is a flowchart of an illustrative process 500 for providing a healthcare management service. At operation 302, a user or caretaker may add medication to an RI subsystem (e.g., via top hatch 140 of subsystem 100a or 300a) and may set times for dispensing the added medication (e.g., via a user interface on subsystem 100a, 200a, or 300a, or a user subsystem 100c), where a drug-to-drug interaction check may be performed (e.g., automatically) by the HMSP (e.g., based on user health data, etc.). Alternatively, at operation 504, a user may receive a pre-filled tray (e.g., tray 290 (e.g., in the mail)) and the user may scan a barcode (e.g., using a camera of system 1) to confirm a correct tray and identify contents in each compartment of the tray, which may automatically create a schedule with the RI subsystem (e.g., subsystem 200a), such as based on doctor/pharmacy orders, such that when the tray deposits its contents into a container of the RI subsystem or is other disposed in the RI subsystem, the content may be appropriately distributed. At operation 506, once the medication has been loaded into the RI subsystem at operation 502 or 504, the RI subsystem may determine that it is the appropriate time for a user to take a dose of the medication. At operation 508, the RI subsystem may wake up and attempt to identify a proper user and/or shine light (e.g., glow about) a receptacle and/or provide an appropriate notification on a user subsystem about the dose being ready. At operation 510, the RI subsystem may be operative to attempt to determine that an appropriate user is proximate the RI subsystem such that the dose may be responsibly dispatched into the receptacle (e.g., by using HSMP-enabled facial detection and/or user-entered biometric information or PIN code access) to suitably authenticate the user at the RI subsystem. If the wrong user is detected by the RI subsystem, the dosage is not released at operation 511a and the HMSP may alert the appropriate user and/or a caretaker at operation 511b (e.g., through a user/caretaker app). Alternatively, if no user is detected by the RI subsystem at operation 513a, then the HMSP may alert the appropriate user and/or a caretaker at operation 513b (e.g., through a user/caretaker app). However, if the appropriate user is detected and authenticated at operation 512, the HMSP may be operative to ask the user if the user wants the dose dispensed at operation 514. If the user answers negatively at operation 515a, the HMSP may query the user as to when the user would like the dose dispensed or when the user would like to be reminded at operation 515b, and then the HMSP may appropriately set a reminder at the desired time at operation 515c, which may be checked automatically against any health issues, caretaker-set limitations, and/or the like to ensure that such rescheduling is appropriate. Alternatively, if the user answers affirmatively at operation 516, the HMSP may determine that a receptacle or user's hand is positioned properly for receiving the dosage at operation 518 and then may dispense the appropriate medication at operation 520. At operation 522, the RI subsystem may determine that the receptacle has been removed from the position under the dispensing hatch and, if the receptacle is not put back into place at operation 523a (e.g., within a particular amount of time after dosage dispensing), the HMSP may ask the user if the dose has been ingested at operation 523b, and if the user answers yes at operation 523c, the RI subsystem may update its data collection to indicate that the dispensed dosage was ingested at operation 526. However, if the receptacle is detected as being returned at operation 524 (e.g., within a particular amount of time after dosage dispensing), the RI subsystem may update its data collection to indicate that the dispensed dosage was ingested at operation 526.

It is understood that the operations shown in process 500 of FIG. 19 are only illustrative and that existing operations may be modified or omitted, additional operations may be added, and the order of certain operations may be altered. Further, in some implementations, two or more operations may occur in parallel or in a different sequence than described.

Description of FIGS. 20-38

As shown in FIGS. 20-38, another illustrative robotic interface subsystem 300a may be provided with at least certain hardware and may be configured to function as a healthcare companion for an end user. RI subsystem 300a of FIGS. 20-38 may embody similar features of to RI subsystems 100a and 200a. For example, robotic interface subsystem 300a may be provided with at least certain hardware and may be configured to function as a healthcare companion for an end user. RI subsystem 300a may be configured to include the capability to store medications and dispense medications according to any suitable schedule accessible to RI subsystem 300a (e.g., a schedule that an end user may manually input into RI subsystem 300a via an I/O component 316 of RI subsystem 300a and/or a schedule that may be loaded onto RI subsystem 300a from a remote source (e.g., HMS subsystem 10 and/or any other suitable subsystem of system 1). A main body 320 of RI subsystem 300a may feature curved edges and/or a high quality glossy finish. The form factor may represent an anthropomorphic assistant with a face on a circular or any other suitably shaped screen 330. Screen 330 may be provided as a portion of a touchscreen or non-touchscreen I/O component 316 of RI subsystem 300a and may include a cover and circuitry (not shown). For example, such a touchscreen may be exposed at a front of a circular portion of main body 320.

On top of main body 320 may be an inlet port 340 that may serve as pill insertion point that enables pills to be inserted into one or more internal compartments within main body 320. A load operation may trigger when a user interacts with RI subsystem 300a to load a medication or other material into an internal compartment, such that a container 360 may be rotated or otherwise moved to align a compartment with inlet port 340, and then RI subsystem 300a may be operative to instruct the user to load any suitable amount of material (e.g., one dose of medication) therein, after which container assembly 360 may be rotated or otherwise moved to align another compartment with inlet port 340 to repeat the process as appropriate. As will be explained below, inlet port 340 may be blocked by a filled cell within container 360 once the filling process has been completed. On a bottom or downwardly facing surface of main body 320 may be outlet port 342 that enables content (e.g., medications) from the internal compartment(s) of main body 320 to be dispensed to an end user (e.g., into a drinking glass) that may be positioned underneath outlet port 342. One or more sensors (e.g., capacitive and/or near-field communication ("NFC") sensor(s)) may be provided to determine if a particular container (e.g., a glass receptacle or a plastic receptacle or no receptacle) is positioned adjacent to outlet port 342. As will be further explained below, container 340 may be rotated into the appropriate position by RI subsystem 300 to dispense contents out of container 340 through the outlet port.

A back of main body 320 may include a cover 350 that may allow access to the internal receptacle(s) (e.g., medication container(s)) within main body 320). Cover 350 may be configured to be removed for enabling access to the internal receptacle(s) only upon user authentication via fingerprint verification or any other suitable authentication (e.g., using any suitable sensor of subsystem 300a), such that the contents may be protected from people other than the appropriate end user (e.g., meddling children or a thieves). For example, cover 350 can be opened to allow a user to remove container assembly 360 and take it on vacation or to use it as a manually operated pill container.

Main body 320 may at least partially enclose or support one or more processors 312 (e.g., on a printed circuit board), touchscreen 330, external camera sensor 315, at least one microphone sensor (e.g., one or two omnidirectional microphones), at least one speaker I/O component (e.g., tweeter and subwoofer), any suitable wireless communication adapters (e.g., a Wi-Fi transceiver and a Bluetooth transceiver). Main body 320 may also enclose a rotary motor that spins shaft 345 around rotation axis B, a linear motor (not shown) that selectively interfaces with container assembly 360, and electronics (not shown) for controlling operation of the rotary motor and the linear motor. One or more light emitting I/O components (e.g., mood lights) may be provided adjacent the dispensing hatch for illuminating the space at which contents may be released from main body 320 for an end user. One or more motion sensors and/or image or camera sensors may be provided by a respective hatch to detect filling and dispensing of contents with respect to the internal receptacle(s) of main body 320.

The internal receptacle(s) of main body 320 may be provided by container 360 (e.g., a removable antibacterial medicine container). As shown, container 360 may be provided as a circular container of any suitable material (e.g., plastic) with a central spoke opening for motorized rotation about a rotation axis by a motor that may be positioned at least partially within or supported by main body 320. Container 360 may be subdivided to include any suitable number (e.g., 28 or 31) of compartments in a circumferential manner. Each compartment may be sized to receive and retain at least one dose of at least one medication for an end user.

Container 360 may be a multi-piece assembly including segmented container member 362, ring member 380, cover member 390, and knob 400. Container member 362 may sit inside ring member 380 and cover member 390 and knob 400 may be positioned on top of container member 362. Each of segmented container member 362, ring member 380, cover member 390, and knob 395 may rotate about a common rotation axis B. In one embodiment, RI subsystem 300a may rotate container member 362 independent of ring member 380 such that ring member 380 remains stationary while container member 362 is moved inside of ring member 380. In another embodiment, RI subsystem 300a may rotate ring member 380 and container member 362 in concert with each other. Thus, when ring member 380 rotates, container member 362 follows suit. In yet another embodiment, when container 360 is removed from RI subsystem 300a, container member 362 may be locked in place with respect to ring member 380 such that it does not freely rotate within ring member 380, but the user can manually rotate cover 390 by turning knob 400.

Figure 25:
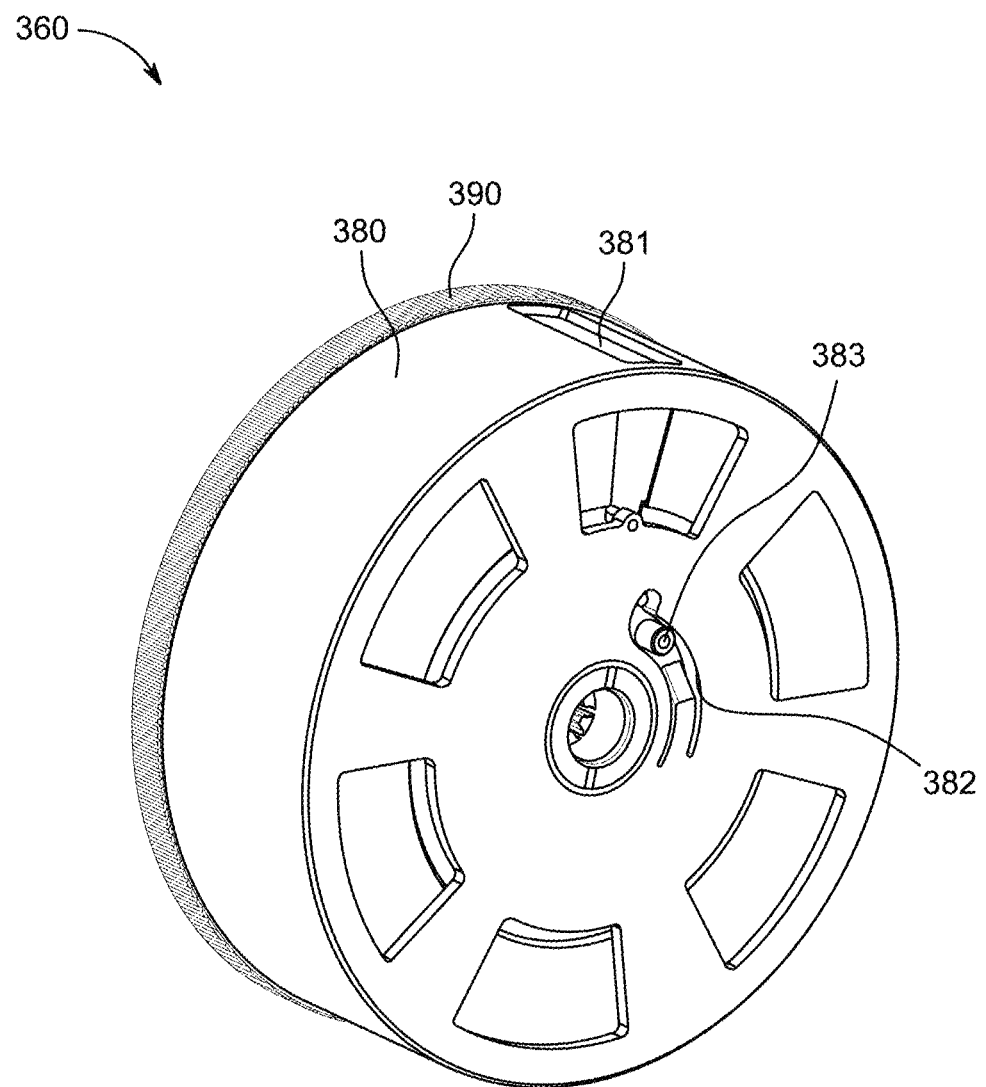
Figure 26:
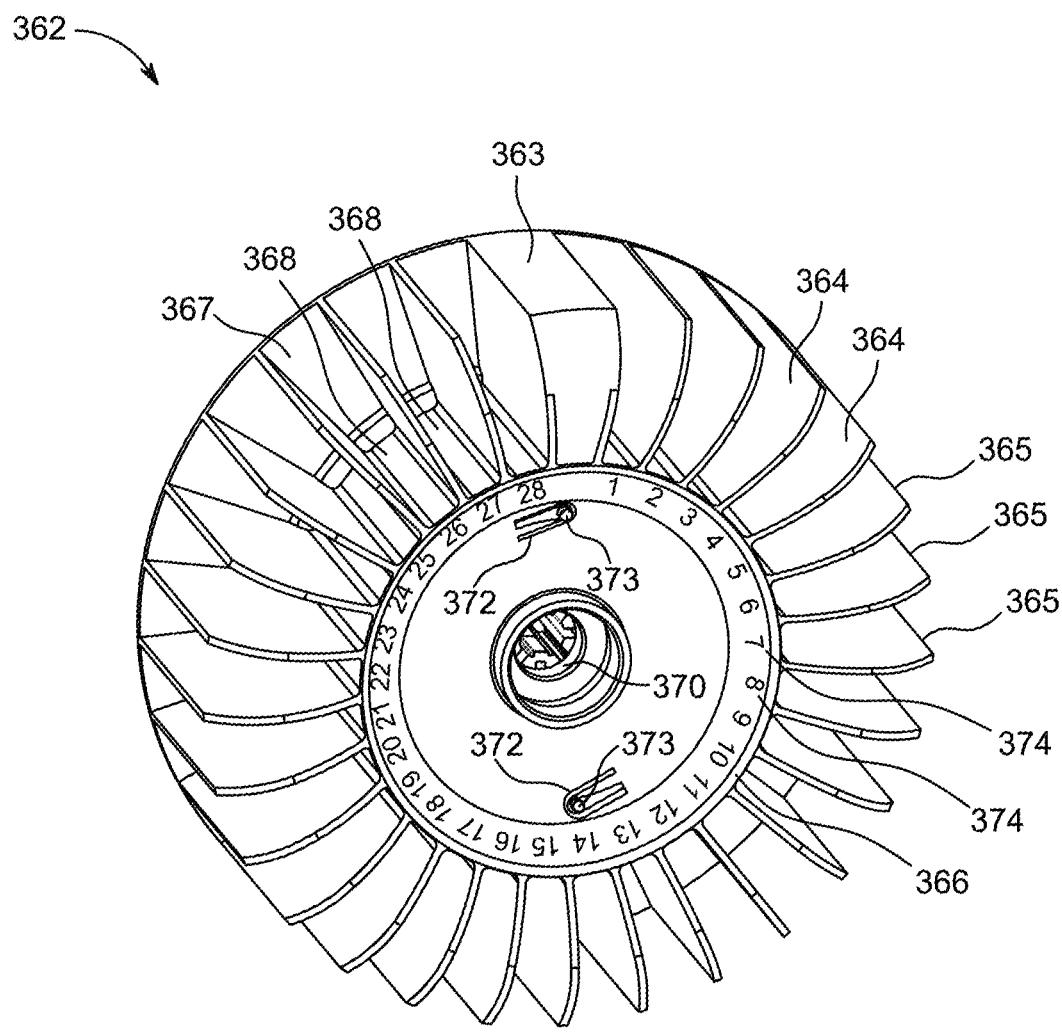
Figure 27:
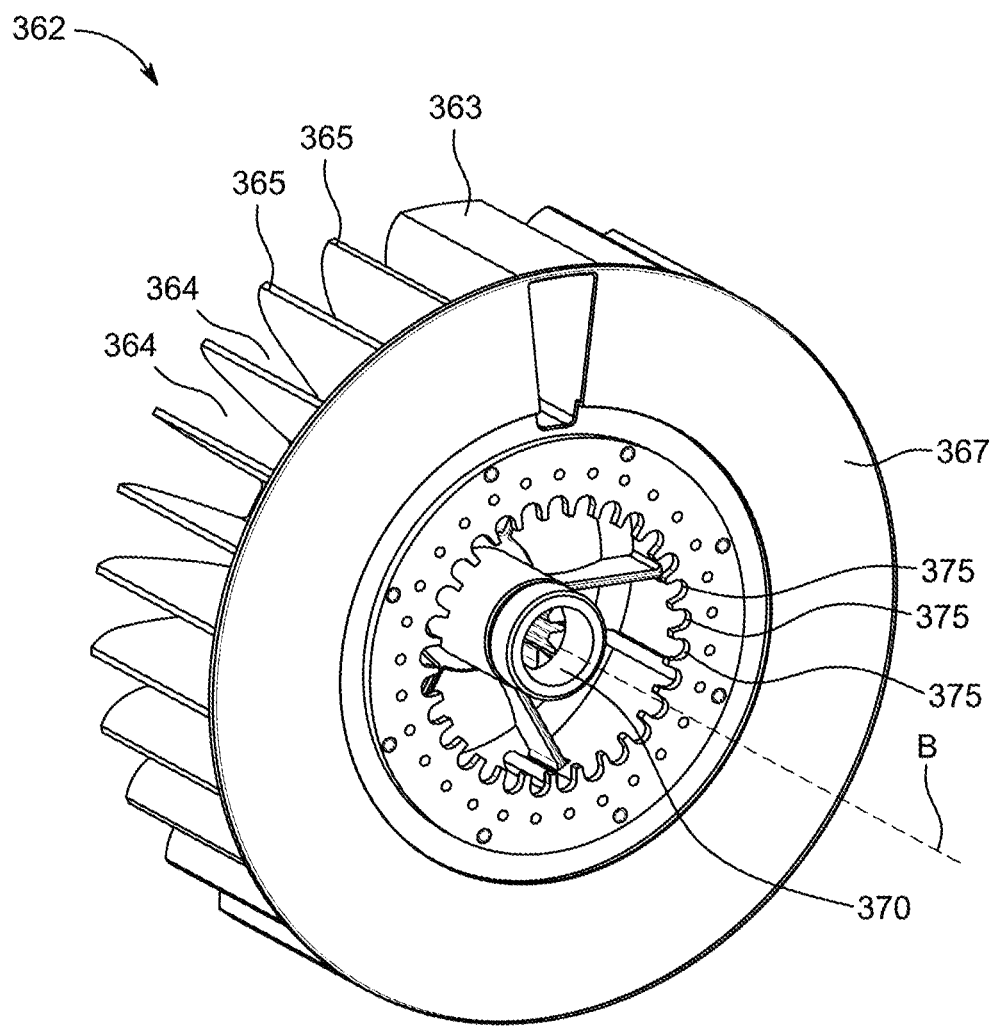
Figure 28:
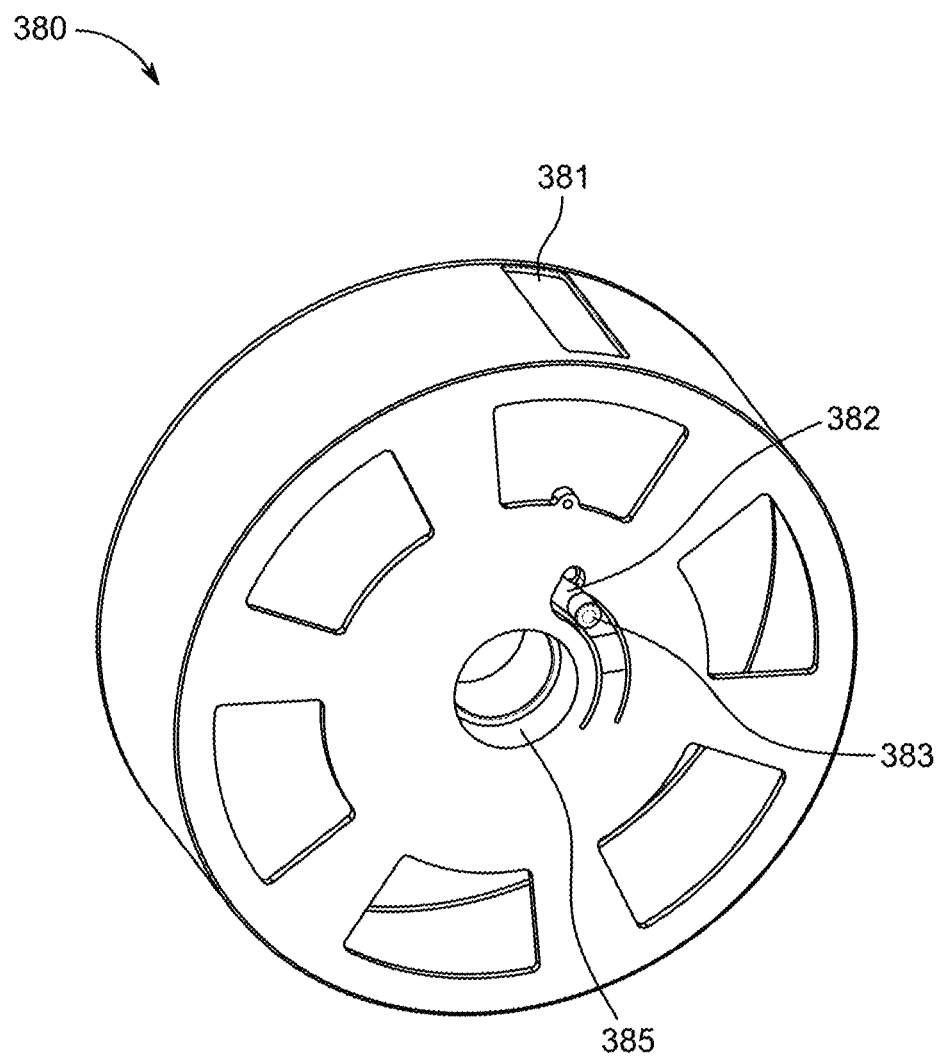
Figure 29:
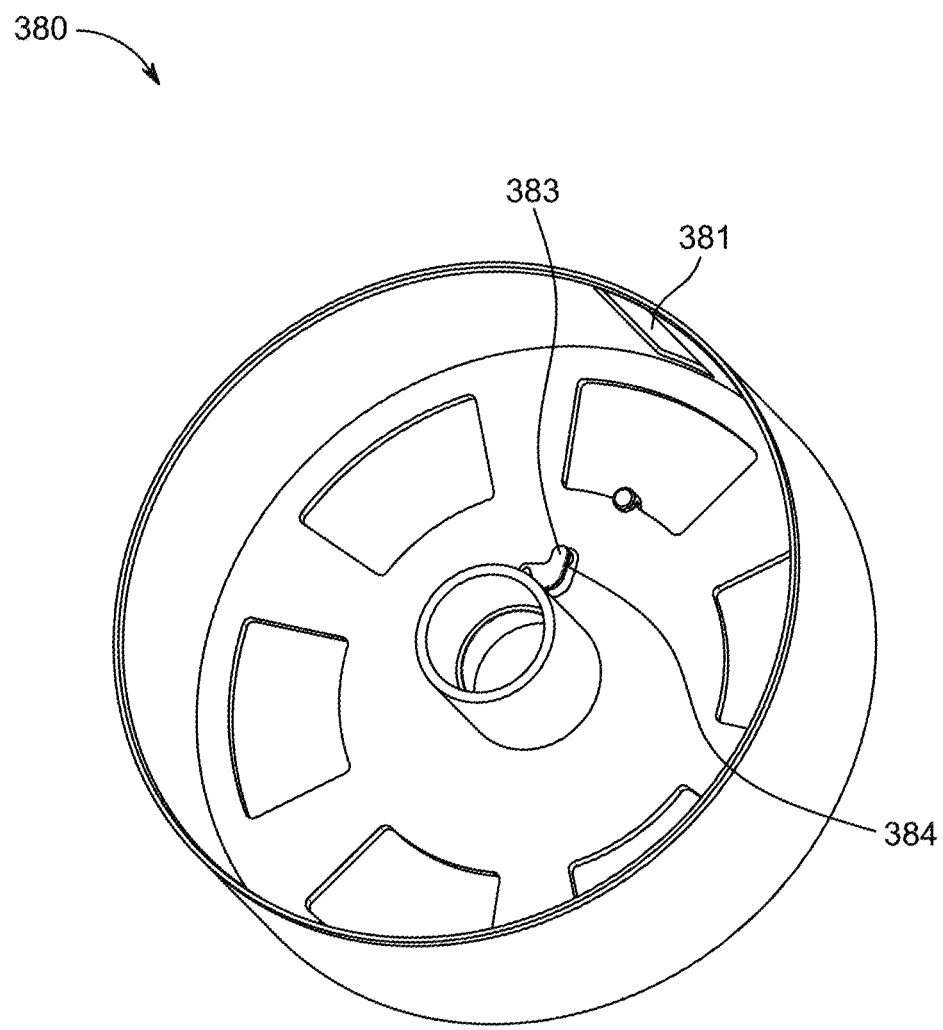
Figure 30:
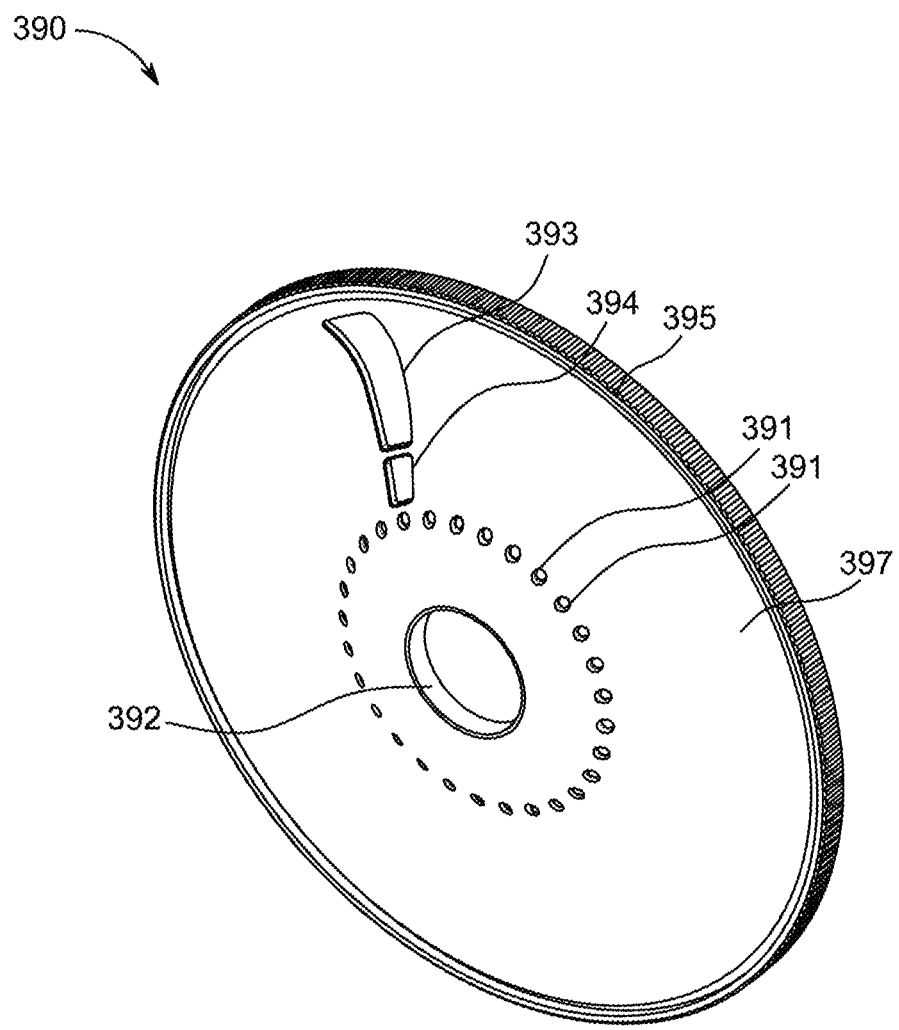
Figure 31:
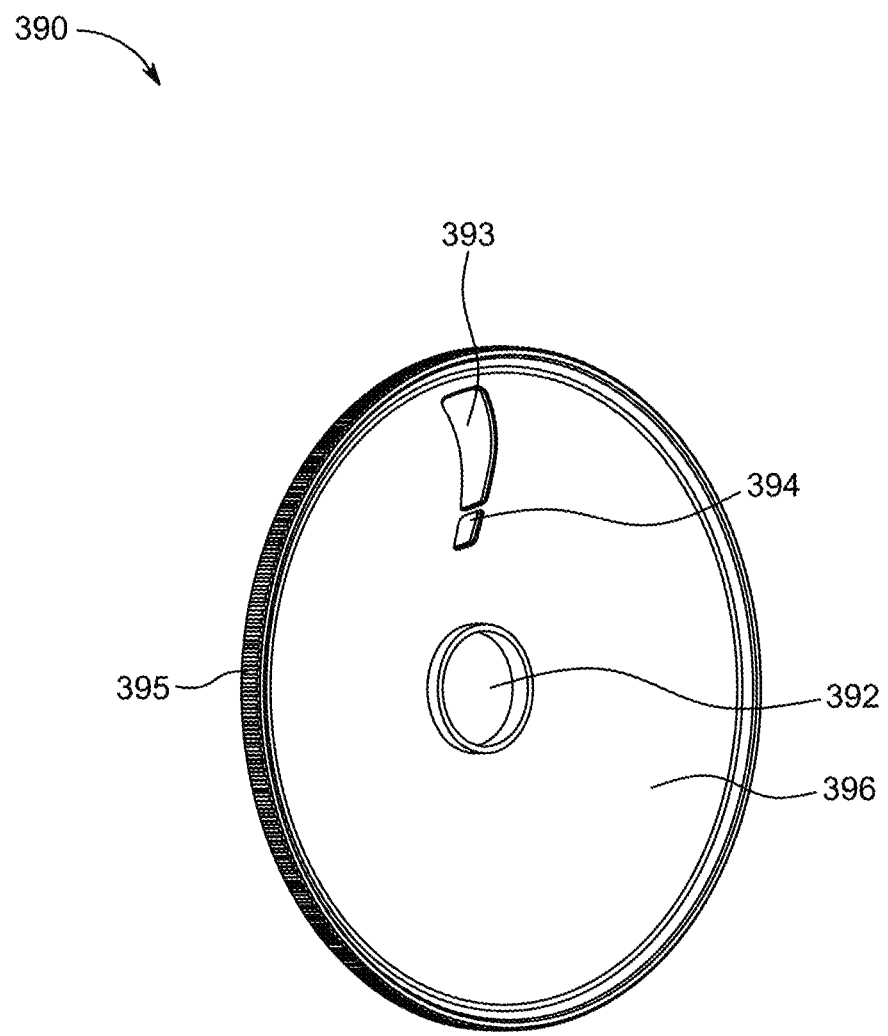
Figure 32:
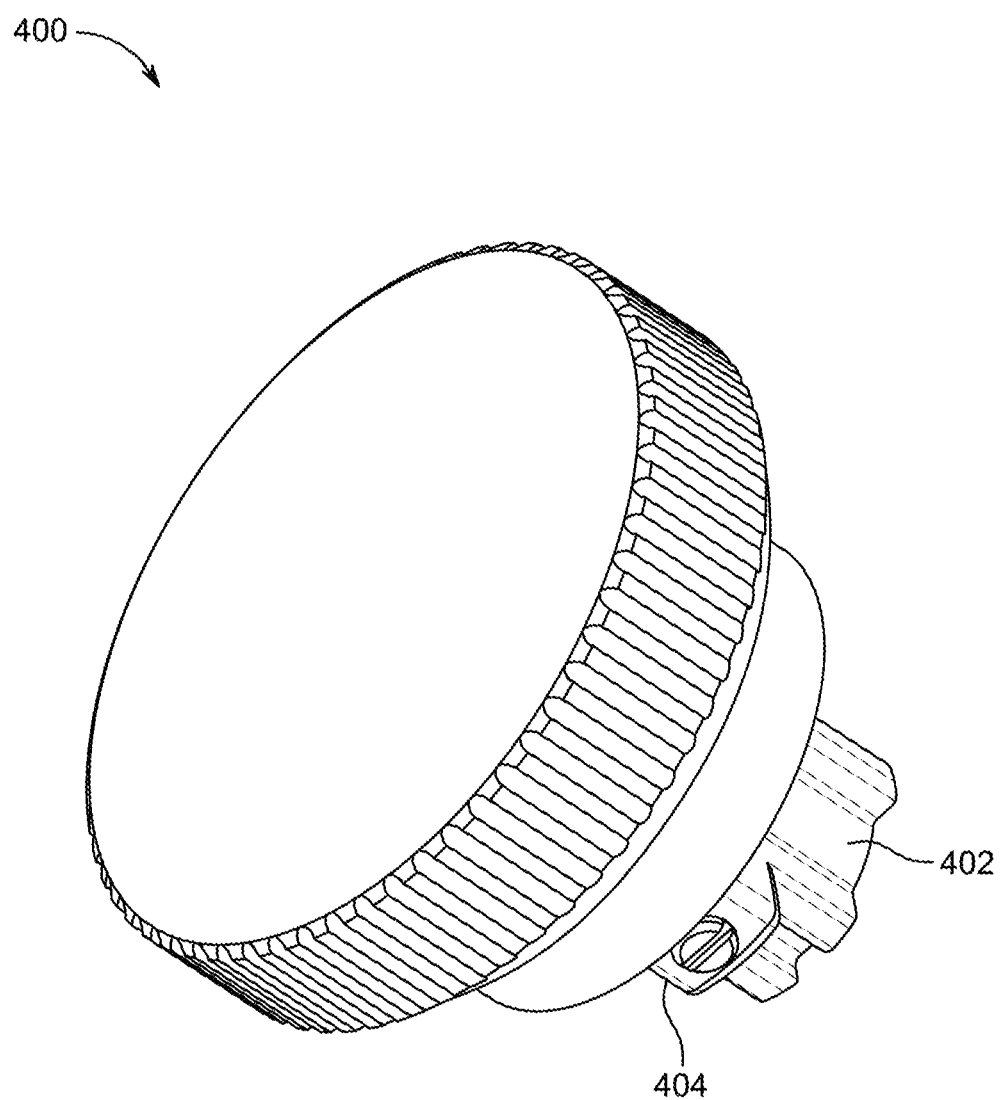
Figure 33:
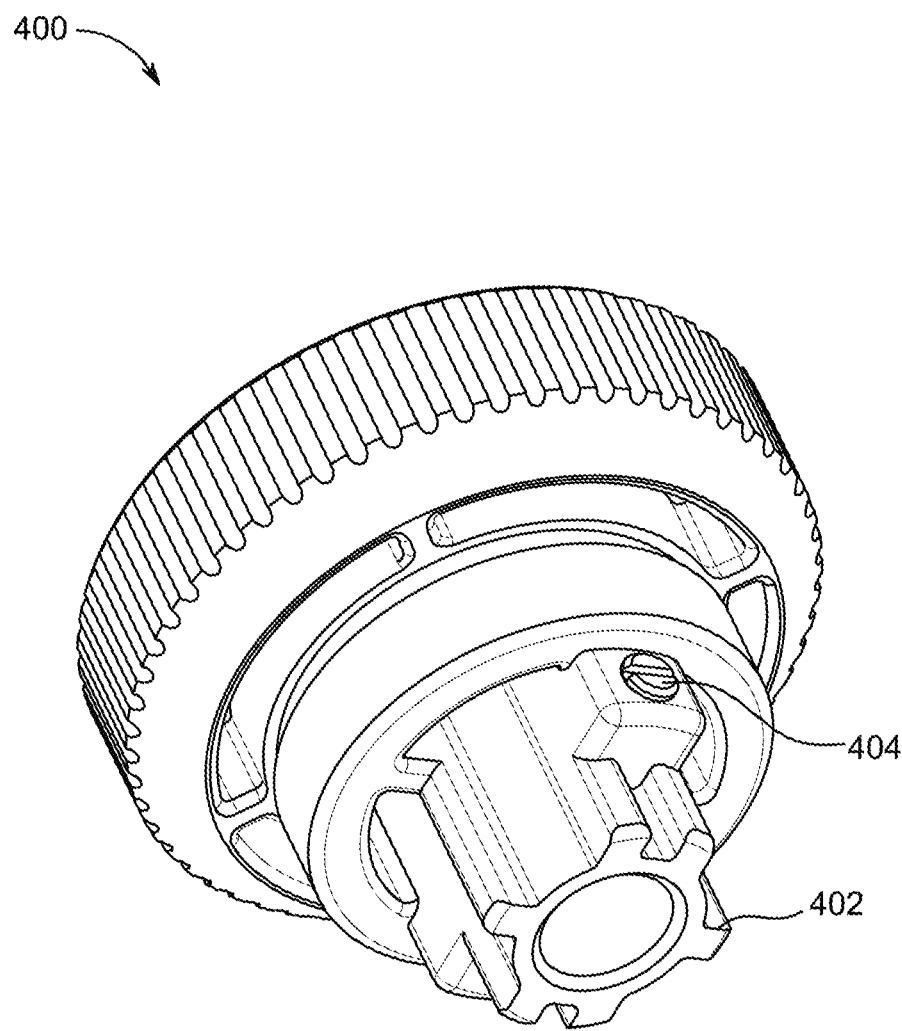

FIG. 25 shows an illustrative backside isometric view of container assembly 360 showing container member 362 positioned within ring member 380, and cover 390 positioned over container member 362 and ring member 380.

Segmented container member 362 can include several compartments 364 that are distributed around the circumference of member 362. Each compartment 364 may be delineated by blade members 365 that extend from cover surface 366 to backplate 367, surfaces 368, ring member 380, and cover 390. That is, each of blade members 365, backplate 367, surface 368, ring member 380, and cover 390 represent a boundary wall, or a portion of a boundary wall, that forms one of compartments 364. Filled member 363 may fully occupy one of compartments 364 such that no materials may be contained therein. Filled member 363 may be used to shut off inlet port 340 when filled member 363 is aligned with inlet port 340.

Segmented container member 362 can include retention region 370 is designed to interface with a shaft of a motor that causes container 360 to rotate about axis B. Retention region 370 may also interface with knob 400. That is, a motor shaft may enter region 370 through the backplate 367 side of member 362 and knob 400 may enter region 370 through the cover surface 368 side of member 362. Cover surface 368 may include spring biased members 372 that are operable to serve as friction members that provide tactile and/or audible feedback when the user is manually rotating cover 390 using knob 400. Spring biased members 372 may include an engagement member 373 (e.g., a knob or protrusion) that engages one of reciprocal engagement members 391 (e.g., holes or slots) of cover 390. If desired, spring biased members 372 may enable step-wise rotation of cover 390 with respect to member 362. Also existing on cover surface 366 can be indicia 374 that indicates a compartment number. Indicia 374 may be visible to users when container 360 is being used manually.

Segmented container member 362 can include gears 375 that are arranged concentric with respect to rotation axis B. Gears 375 can enable ring member 380 to lock in place onto container member 362 such that when the motor shaft rotates, both ring member 380 and contain member 362 rotate in concert with each other. The number of gears 375 may be same as the number of compartments 364, including filled member 363. For example, if there are 28 compartments and one filled member, the number of gears may be 29. This way, any one of compartments 364 or filled member 363 can be locked in place with respect to window 381 of ring member 380.

Ring member 380 can include window 381, gear engagement member 382, which may include push button nub 383 and engagement member 384, and bearing retaining region 385. Window 381 may serve as a pill loading and dispensing passageway when container 360 is being used in RI subassembly 300a. In some embodiments, only one such window 381 may exist in ring member 380. Push button nub 383 is operative to engage with any one of gears 375 when it is in a gear engagement position. When push button nub 383 is in the gear engagement position, ring member 380 is locked in place with respect to segmented container member 362 and thus rotates in concert with member 362 when the motor rotates its shaft around rotation axis B. Push button nub 383 may be in a gear engagement position or a non-engagement position depending on whether an external force is being applied to nub 383. When no external force is being applied to nub 383, nub may be in its gear engagement position. When an external force is being applied to nub 383 (e.g., via a linear motor), nub may be in its non-engagement position. The external force may push nub 383 towards container member 362 to disengage nub 383 from any of the gears 375 to which it was engaged. Once disengaged, container member 362 may rotate independent of ring member 380. Nub 383 may be attached to engagement member 384 that engages with one of gears 375. Thus, when in the gear engagement position, engagement member 384 nestles into one of gears 375, but when in the non-engagement position, engagement member 384 is pushed away from gears 375 and no longer permitted to touch one of gears 375. In some embodiments, engagement member 384 may be chamfered to facilitate gear engagement when the external force is no longer applied.

Cover 390 can include reciprocal engagement members 391, throughhole 392, pill window 393, indicia window 394, ribbed edge 395, top surface 396, and bottom surface 397. Reciprocal engagement members 391 may exist only on bottom surface 397. In one embodiment, the number of reciprocal engagement members 391 may be same as the sum total of the number compartments 364 and filled member 363. This way, for each step wise rotation, pill window 393 is aligned over one of compartments 364 or filled member 363 and indicia window 394 is aligned over one of indicia 375. Ribbed edge 395 may provide grip for enabling the user to manually rotate cover 390 with respect to container member 362 and/or ring member 380. When cover 390 is attached to container member 362, it cannot move if no torsion is applied to it. Cover 390 can be rotated by hand to align windows 393 and 394 to the desired compartment 364 and the rotation can be performed in a step wise manner.

Knob 400 may be used to secure cover 390 to compartment member 362. Keyed member 402 may engage with retention region 370 and held in place, for example, with a friction fit. In some embodiments, knob 400 may be fixed in place and does not rotate cover 390 when it is rotated by a user. The user may rotate cover 390 as it spins around knob 400. Knob 400 may also have thread screws 404 for securing knob 400 to motor shaft 345.

It should be understood that cover 390 and knob 400 may be replaced with pre-filled pill tray 290. That is, a tray 290 may be coupled to container member 362 and/or ring member 380.

Figure 34A:
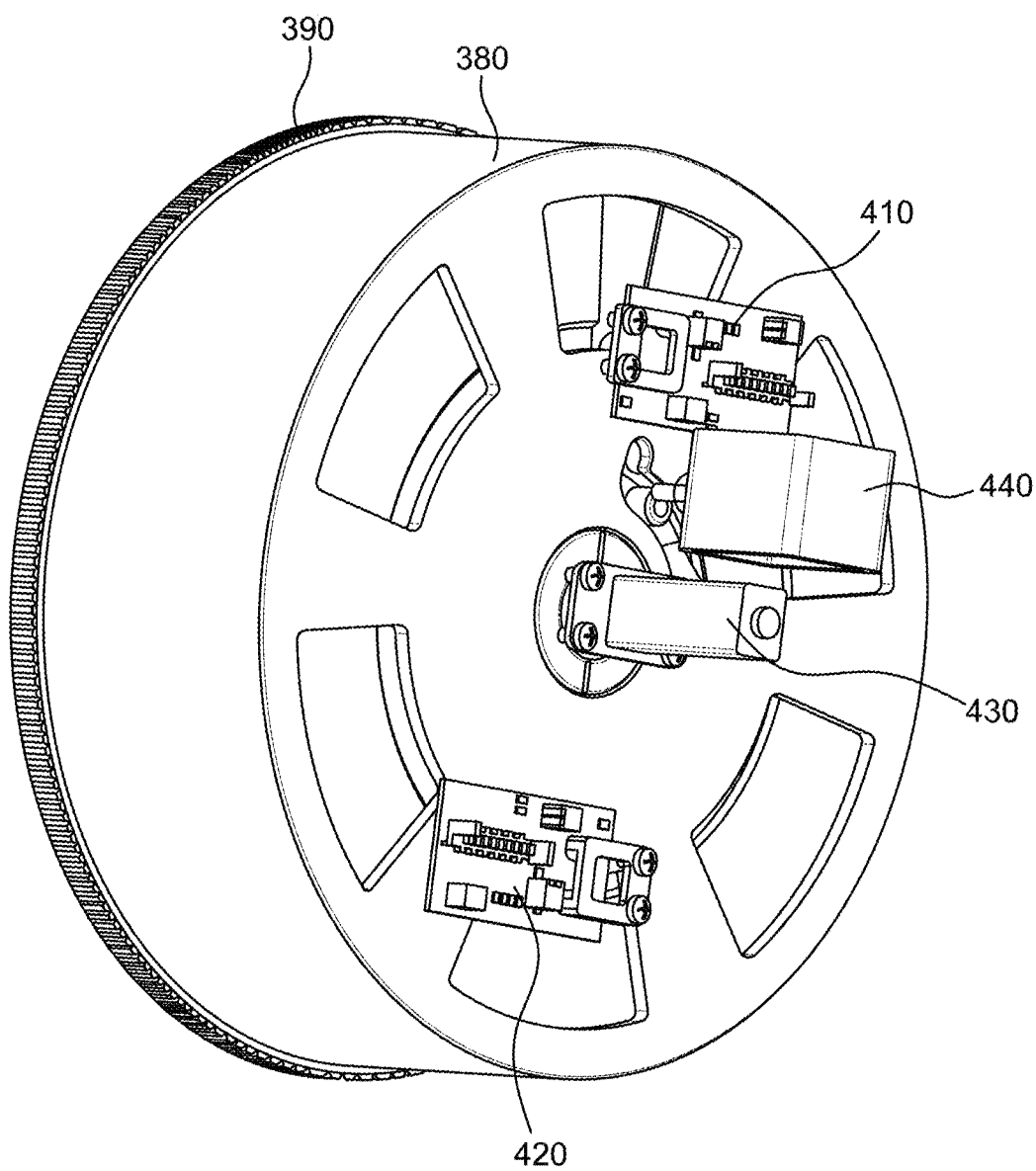
Figure 34B:
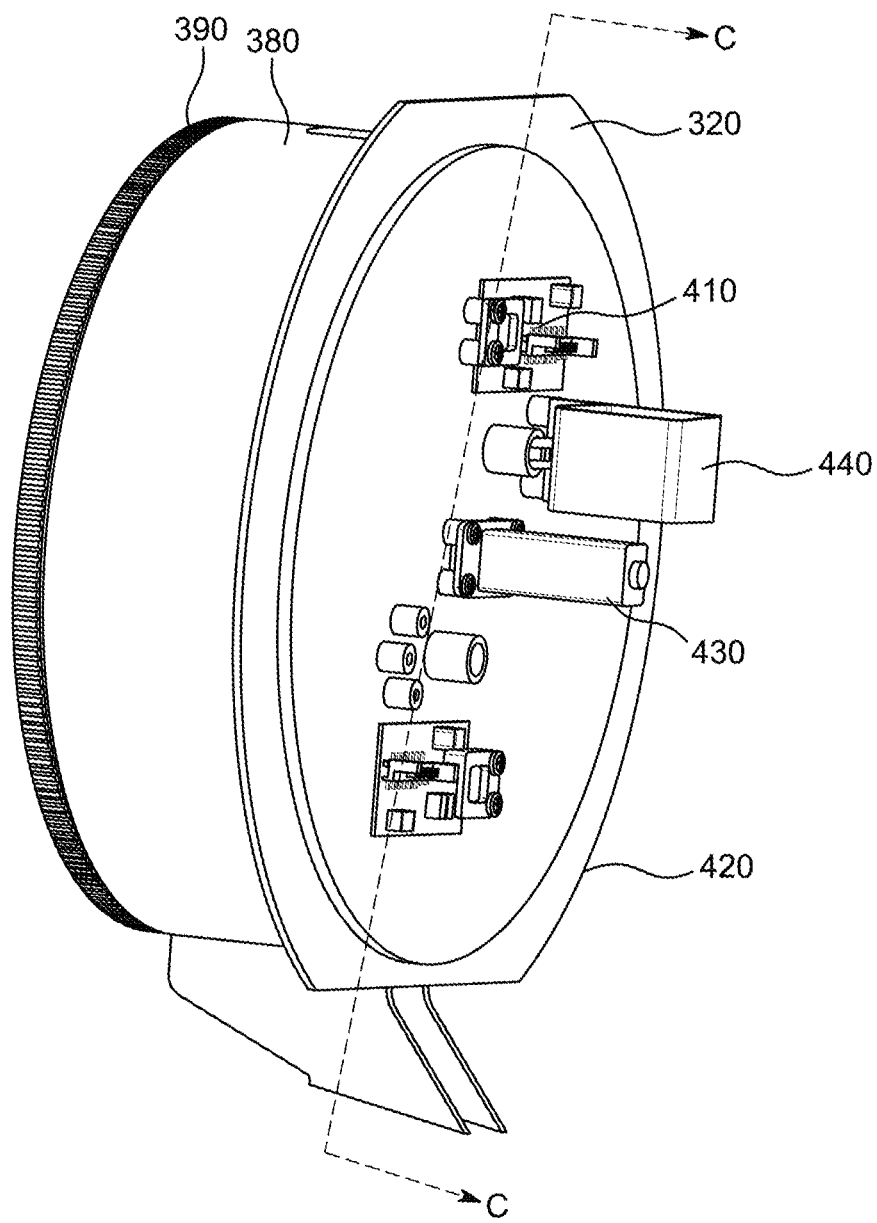
Figure 34C:
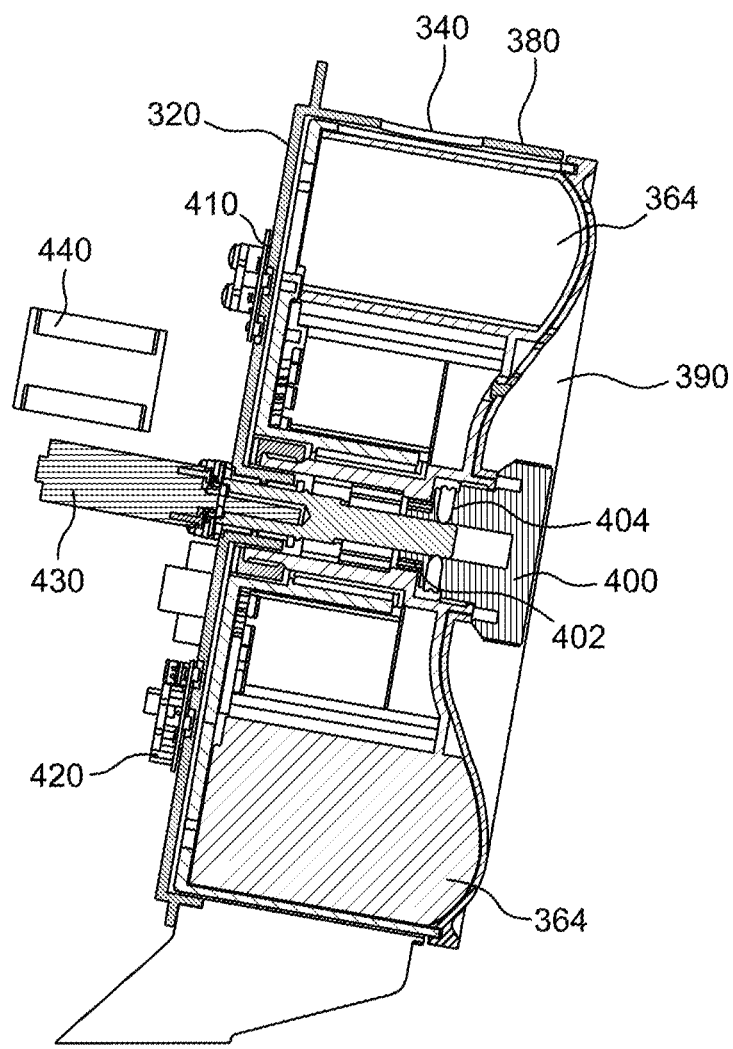
Figure 34D:
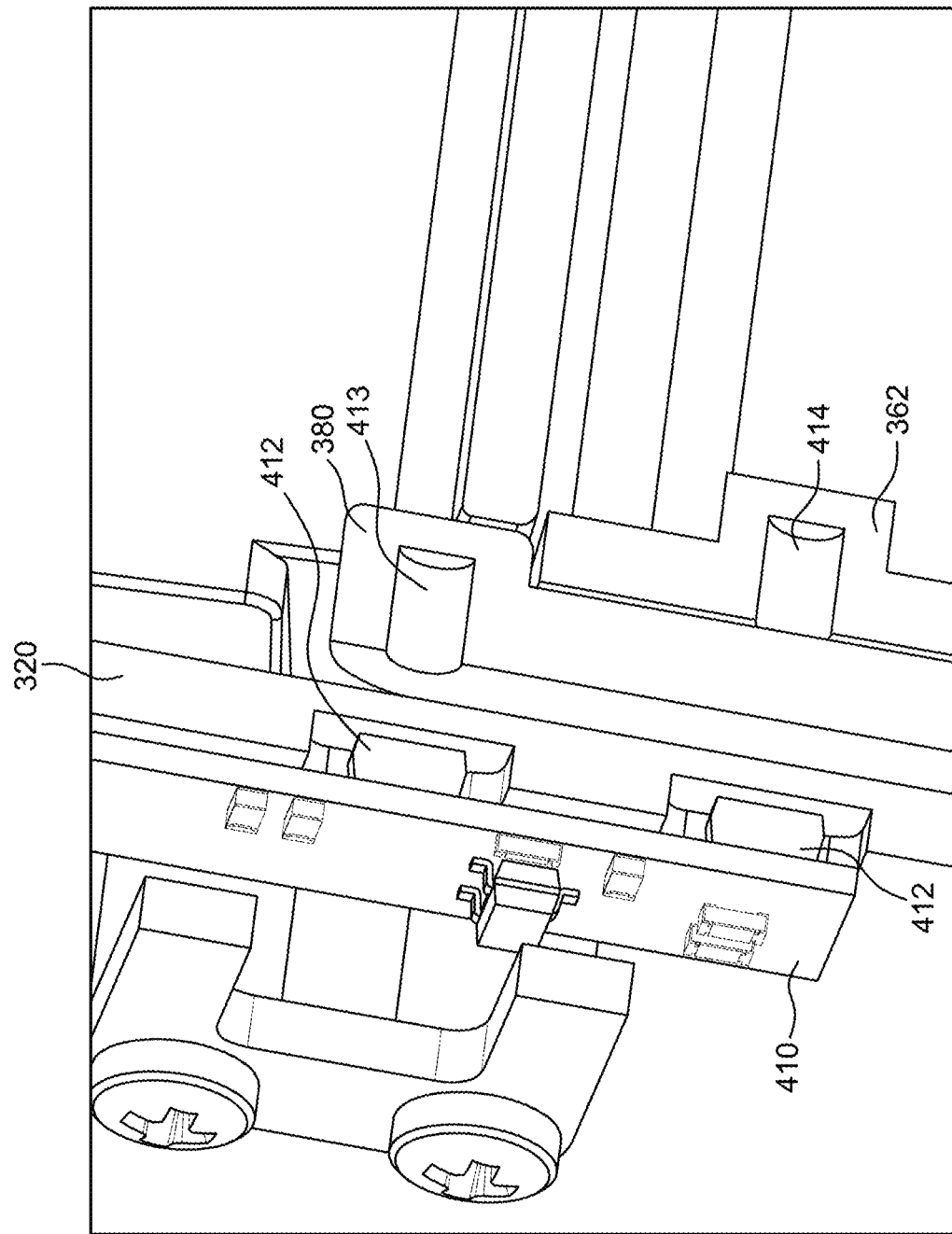

FIG. 34A shows an illustrative back view of container assembly 360 with illustrative circuit boards 410 and 420, rotary motor 430, and linear motor 440. FIG. 34B shows an illustrative view of container assembly 360 mounted to a portion of body 320 along with circuit boards 410 and 420, rotary motor 430, and linear motor 440. FIG. 34C shows an illustrative cross-sectional view taken along CC FIG. 34B. Circuit boards 410 and 420 may support electronics for controlling various operations of RI subassembly 300a including, for example, operation of motors 430 and 440. In addition one or both of circuit boards 410 and 420 may include sensor such as hall sensors to monitor position of container assembly 360. For example, FIG. 34D shows an illustrative cross-sectional view of circuit board 410 and portions of body 320, ring member 380, and container member 362. Also shown in FIG. 34D are hall effect sensors 412, ring member magnet region 413 for retaining a magnet (not shown), and container magnet region 414 for retaining a magnet (not shown). Hall effect sensors 412 can sense magnets contained in ring member magnet region 413 and container magnet region 414 to determine an orientation of ring member 380 and container member 362 with respect to body 320. In some embodiments, container member 362 may include many container magnet region 414 (and respective magnets). For example, there may be a container magnet region 414 for each compartment 364 (not shown). In some embodiments, ring member 380 may include only one ring member magnet regions 413 (and respective magnet) that is aligned with pill window 381 (not shown).

Rotary motor 430 may be responsible for rotating container member 362 and ring member 380 (when in the gear engaged position). Rotary motor 430 may only rotate container member 362 when ring member is in the not-engaged position. Linear motor 440 may be responsible for coupling/decoupling ring member 380 (particularly engagement member 384) to/from one of gears 375 of container member 362.

Figure 35:
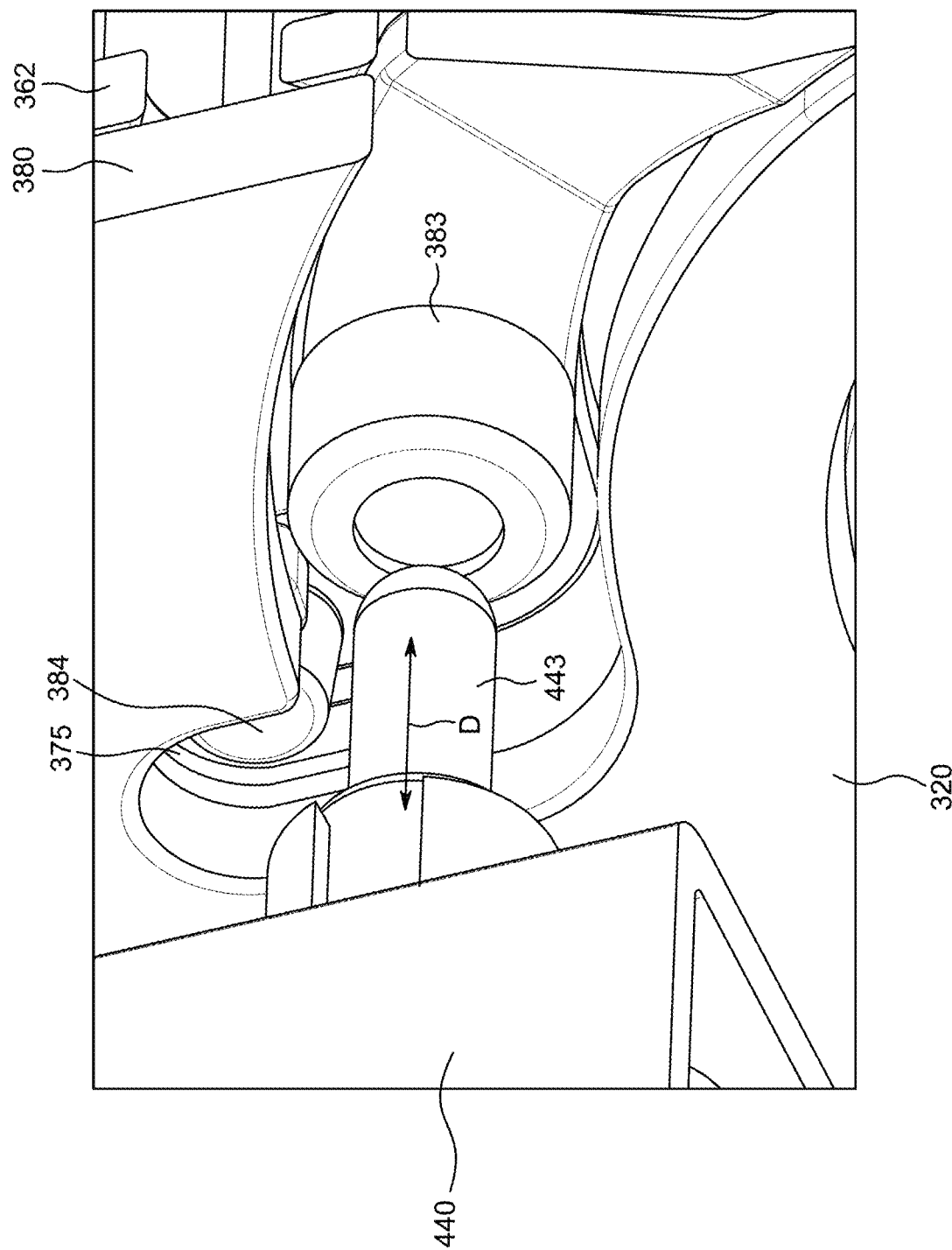

FIG. 35 shows an illustrative close up view of linear motor 440, nub 383 and engagement member 384. To decouple ring member 380 from container member 362, linear motor 440 may cause nub engagement member 443 to travel axially along axis D in the direction towards nub 383 so that nub engagement member 443 interfaces with nub 383 to press engagement member 384 out of contact with gear 375. To couple ring member 380 to container member 362, linear motor 440 may cause nub engagement member 443 to travel axially along axis D in the direction away from nub 383 so that nub engagement member 443 no longer interfaces with nub 383 so as to allow engagement member 384 to engage with gear 375.

Container assembly 360 can be used by humans and machines. When used by a human, the pill window 381 must be aligned with and secured in place with respect to filled member 363 to ensure that the machine loading/dispensing port is closed. In addition, when container assembly 360 is inserted or removed from main body 320, window 393 should be aligned with filled member 363 to prevent inadvertent pill spillage. It is in this configuration that container assembly 360 is completely closed and no pills can be inserted or removed. In addition, because push button nub 383 is biased to interface with one of gears 375 when there is no externally applied force to nub 383, container member 362 is locked in place with ring member 380. As a result, when container assembly 360 is removed from body 320, there is substantially little or no relative motion between ring member 380 and container member 362. When a user wishes to place pills in or retrieve pills from container assembly 360, the user can use one hand to grasp ring member 380 and user the other hand to rotate cover 390 until the opening is aligned with the desired compartment. In this configuration, the desired compartment is opened and can be accessed by the patient. The container assembly can be closed by returning window 393 to filled member 363.

Figure 36:
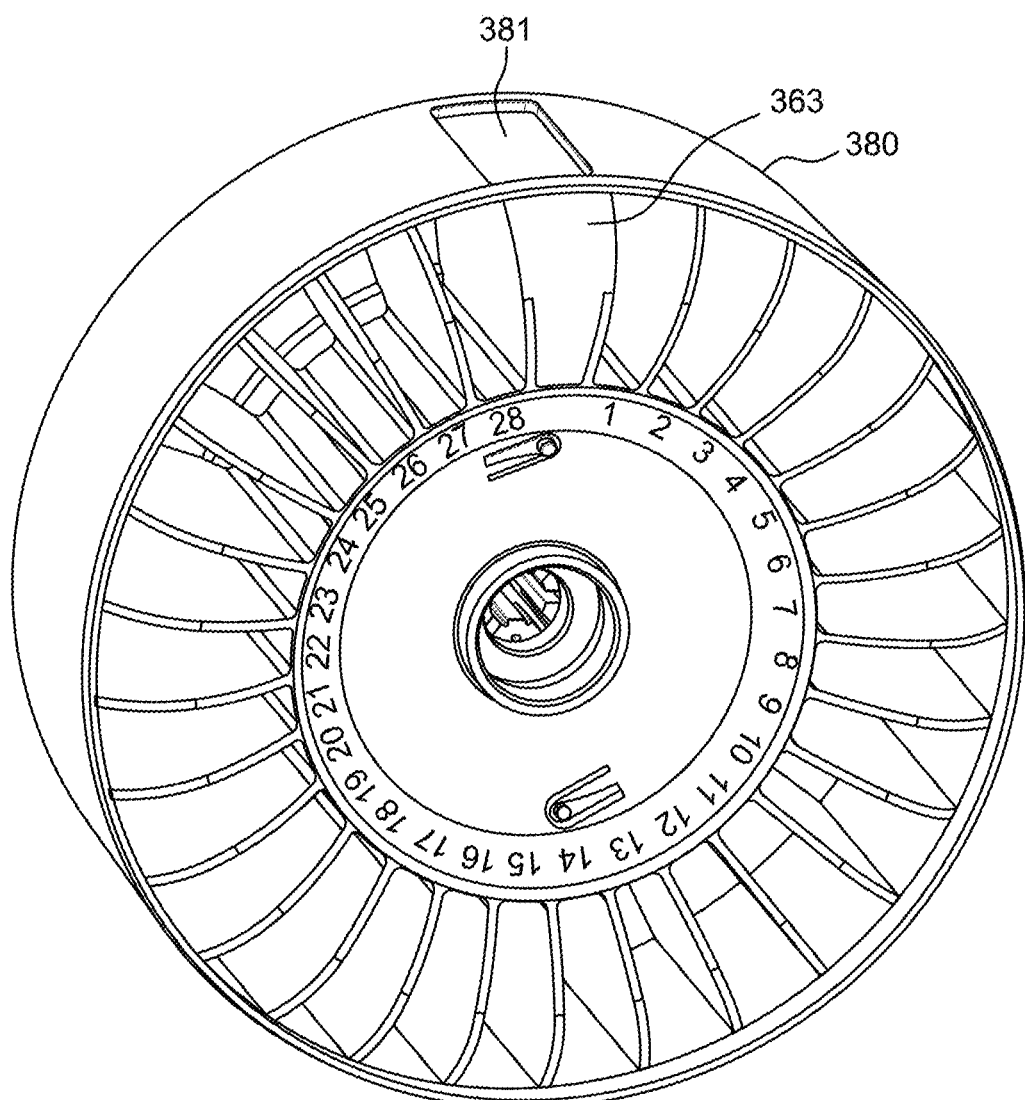
Figure 37:
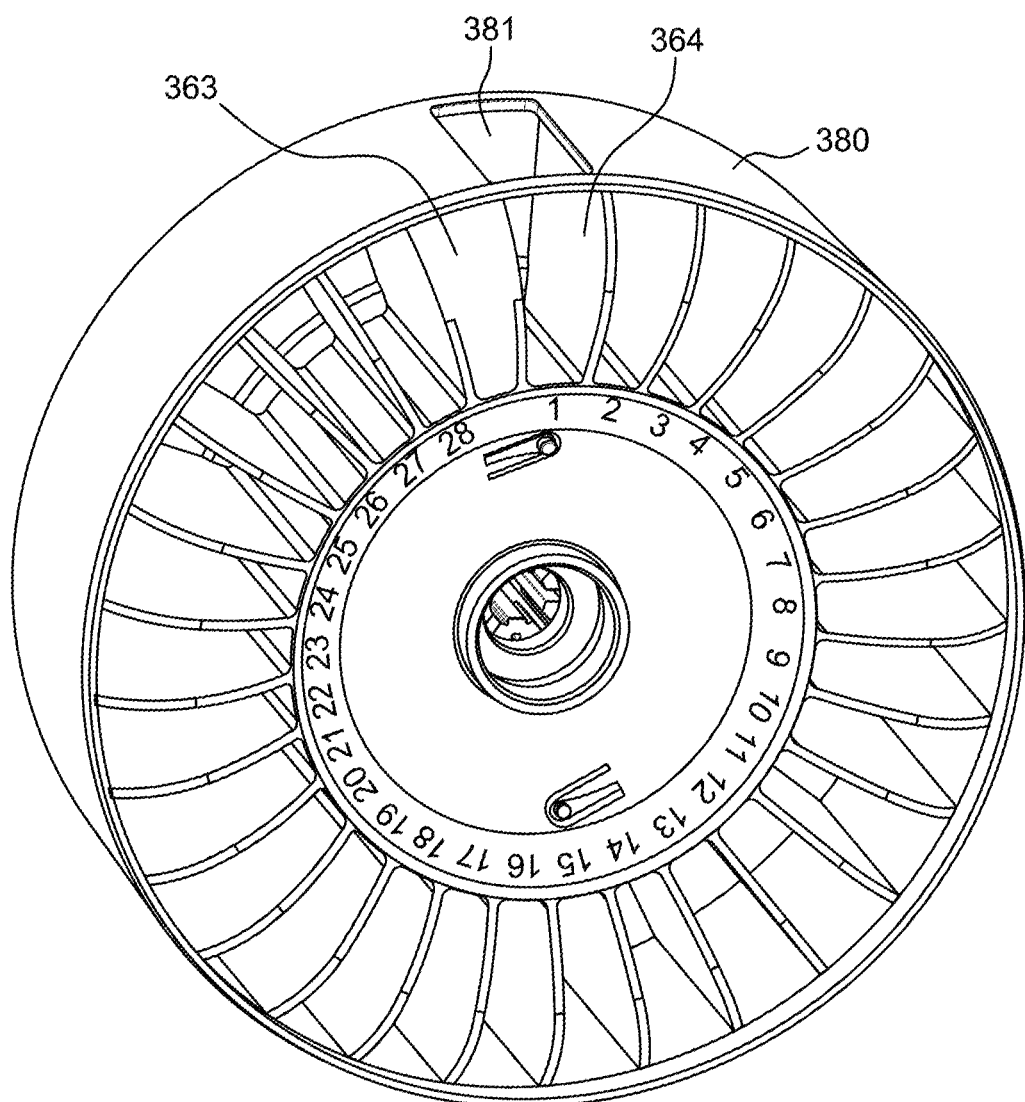
Figure 38:
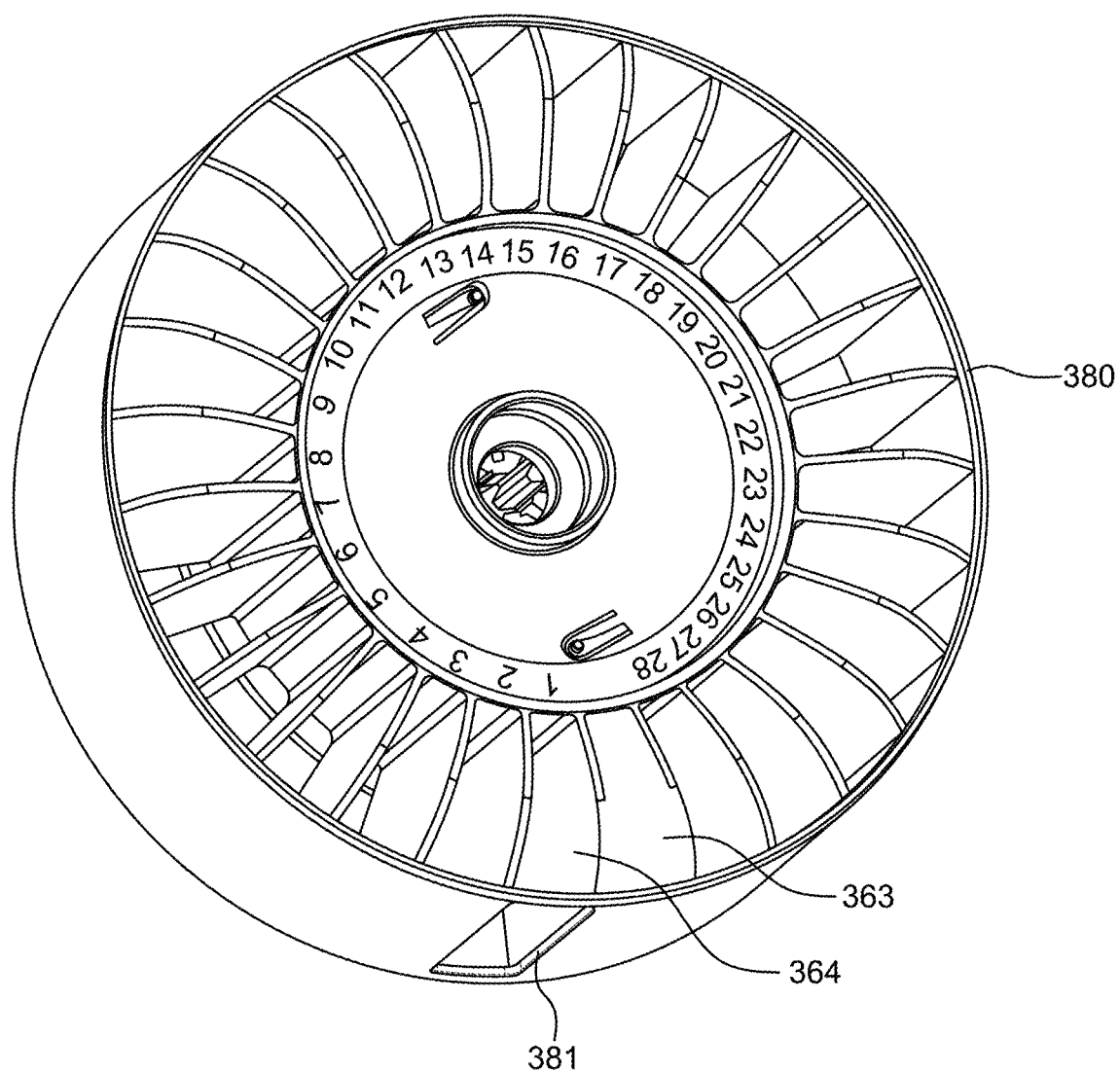

When container assembly 360 is used in a machine, pills are loaded and dispensed via window 383. In the machine, container assembly 360 may be secured in a vertical orientation such that during pill loading, window 381 may be positioned in a 12:00 position and during pill dispensing, window may be positioned in a 6:00 position. For example, FIG. 36 shows container assembly 360 positioned in a closed position in which filled member 363 is aligned with window 381. FIG. 37 shows container assembly 360 positioned in a pill loading position for compartment #1 in which compartment 364 associated with indicia #1 is aligned with window 381 in a 12:00 position (or a position in line with inlet port 340). Note that filled member 363 is rotation one position counter clockwise with respect to window 381. FIG. 38 shows container assembly 360 in a pill dispensing position for compartment #1 in which compartment 364 associated with indicia #1 is aligned with window 381 in a 6:00 position (or a position in line with outlet port 342).

Figure 39A:
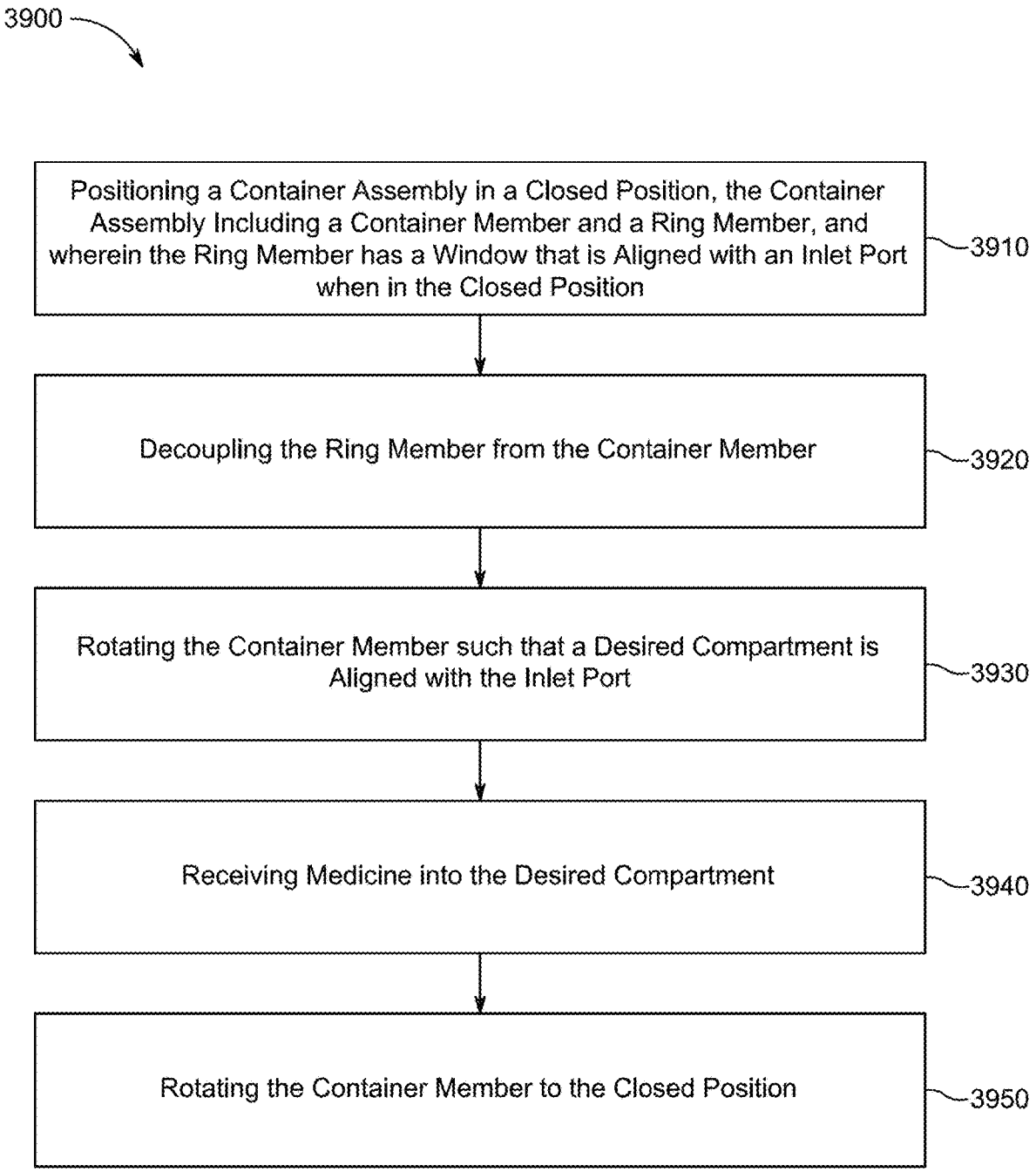
FIG. 39A shows an illustrative process for loading pills into a container assembly using a machine, according to an embodiment.
Figure 39B:
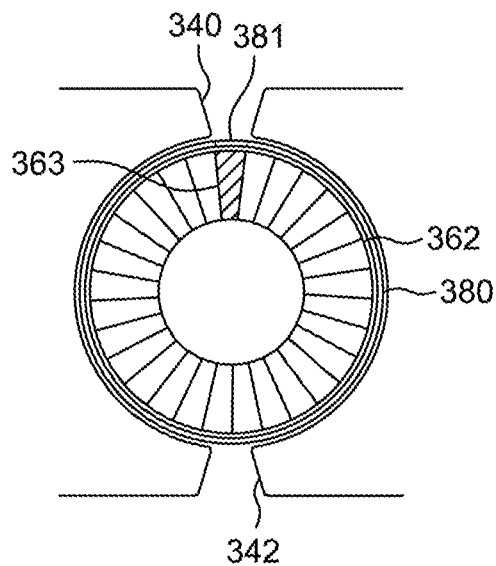
FIGS. 39B-39E show illustrative representations of container assembly in various states of pill loading.
Figure 39C:
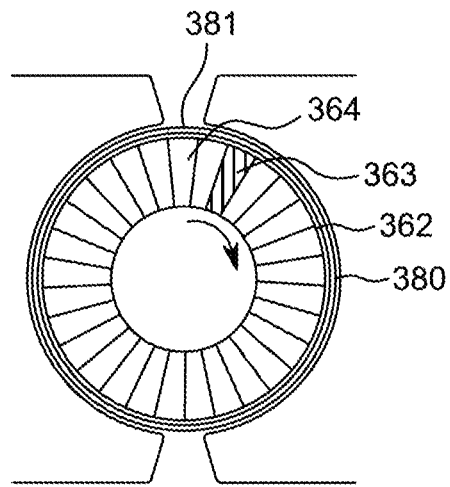

FIG. 39A shows an illustrative process 3900 for loading pills into container assembly 360 using a machine, according to an embodiment. FIGS. 39B-39E show illustrative representations of container assembly 360 in various states of pill loading, and will be referenced during the discussion of process 3900. Starting with step 3910, it can be assumed that container assembly 360 is in the closed position, as illustrated by FIG. 39B. In the closed position, filled member 363 is aligned with pill window 381 of ring member 380, such that pill window 381 is also aligned with inlet port 340. In the closed position, ring member 380 may or may not be integrally coupled to container member 362. That is, linear motor 440 (not shown) may or may not be operating to engage the nub with a gear of the container member. At step 3920, ring member 380 is decoupled from container member 362. As discussed above, this may be accomplished using the linear motor to press the nub 383 towards container member 362 to disengage the engagement member (e.g., engagement member 384) from the gears (e.g., gears 375) of container member 362. At step 3930, the container member is rotated such that a desired compartment 364 is positioned in line with pill window 381 (and inlet port 340). This is illustrated in FIG. 39C. Container member 362 can be rotated via rotation of a rotary motor (e.g., rotary motor 430). When container member 362 is not gear engaged with ring member 380, container member 362 can rotate independently of ring member 380. Thus, pill window 381 remains fixed in place in line with inlet port 340 as container member 362 rotates to position the desired compartments 364 below inlet port 340.

Figure 39D:
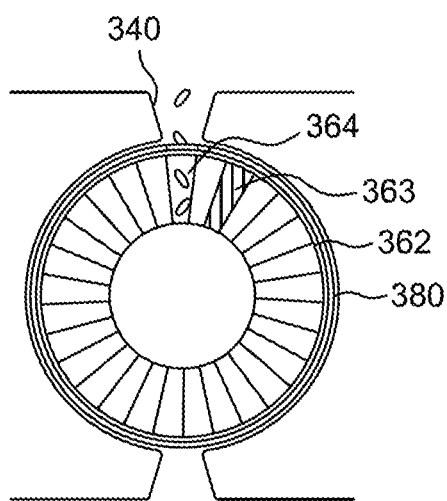
Figure 39E:
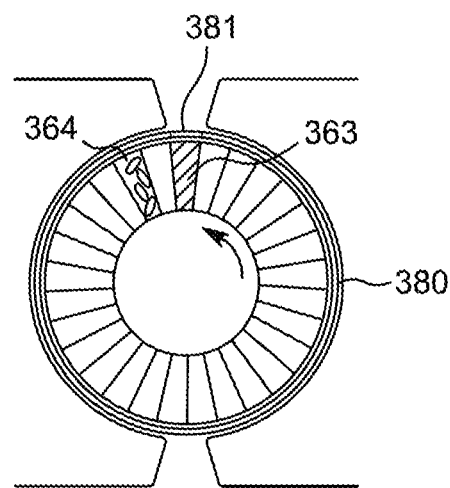

At step 3940, medicine may be received into the desired compartment when a user inserts pills into inlet port 340 and they pass through window 381 into compartment 364. This is illustrated in FIG. 39D. The RI subassembly may be able to detect when pills are no longer being inserted into the container assembly, at which point it may further rotate the container member to a different compartment to receive pills or it may rotate the container member to the closed position. At step 3950, the container member can be rotated to the closed position as shown in FIG. 39E. FIG. 39E shows that pills are contained in compartment 364 and filled member 363 is positioned in line with window 381.

It should be appreciated that the steps shown in FIG. 39A are merely illustrative and that additional steps may be added, that some steps may be omitted, or the order of the steps may be rearranged.

Figure 40A:
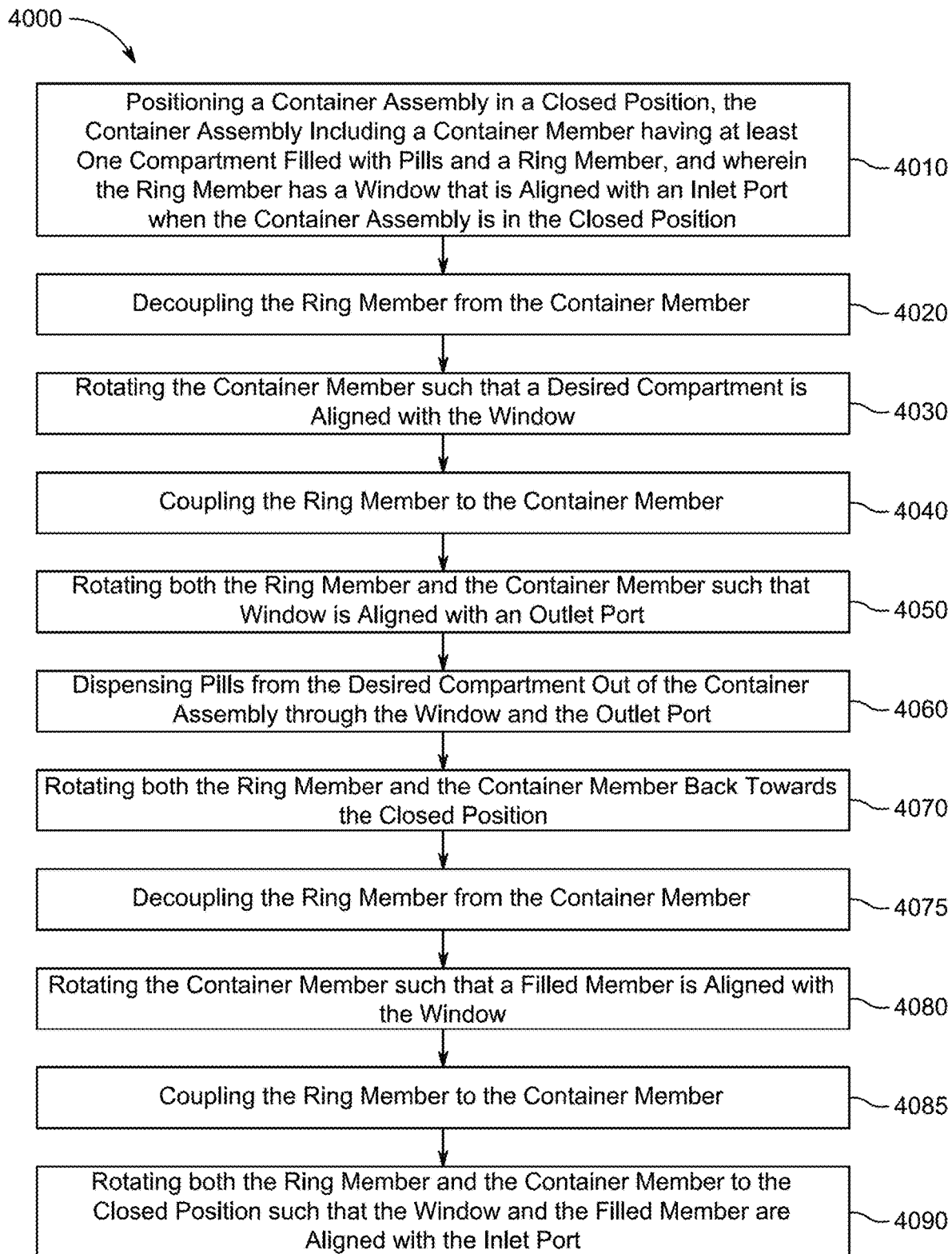
FIG. 40A shows an illustrative process for dispensing pills from a container assembly using a machine, according to an embodiment.
Figure 40B:
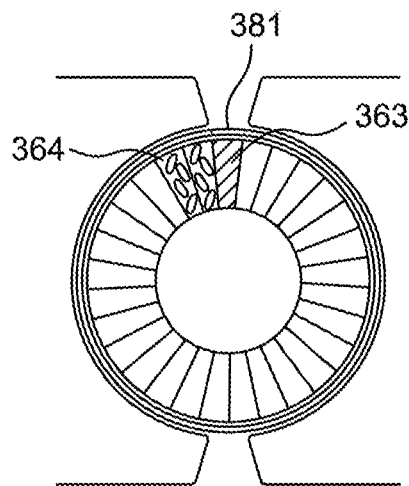
FIGS. 40B-40H show illustrative representations of container assembly in various states of pill dispersal.
Figure 40C:
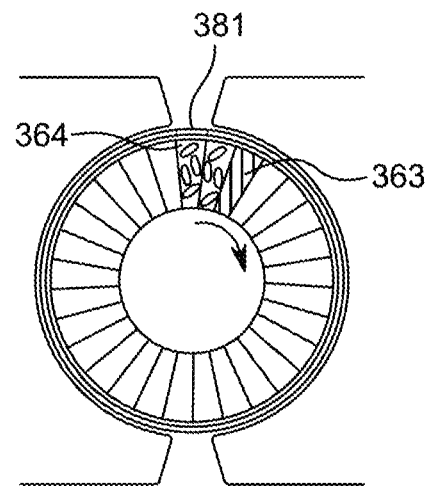

FIG. 40A shows an illustrative process 4000 for dispensing pills from container assembly 360 using a machine, according to an embodiment. FIGS. 40B-40H show illustrative representations of container assembly 360 in various states of pill dispersal, and will be referenced during the discussion of process COO. Starting with step 4010, it can be assumed that container assembly 360 is in the closed position and pills are contained in compartment 364, as illustrated by FIG. 40B. At step 4020, ring member 380 is decoupled from container member 362. As discussed above, this may be accomplished using the linear motor to press the nub 383 towards container member 362 to disengage the engagement member (e.g., engagement member 384) from the gears (e.g., gears 375) of container member 362. At step 4030, the container member is rotated such that a desired compartment 364 is positioned in line with pill window 381. This is illustrated in FIG. 40C. Container member 362 can be rotated via rotation of a rotary motor (e.g., rotary motor 430).

Figure 40D:
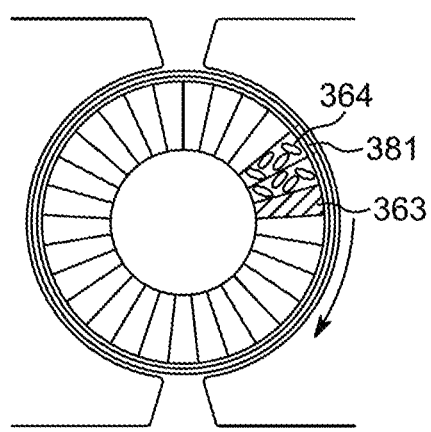
Figure 40E:
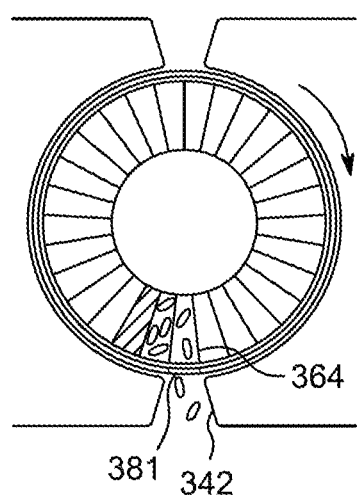

After the desired compartment 364 is positioned in line with pill window 381, ring member 380 may be integrally coupled to container member 362, as step 4040. This way, when the rotary motor rotates its shaft, both ring member 380 and container member 362 rotate in concert with each other. At step 4050, both ring member 380 and container member 362 are rotated such that window 381 and the desired compartment 364 are positioned over the outlet port (e.g., port 342). This rotation is shown in FIGS. 40D and 40E. The pills are dispensed out of the outlet port when window 381 and the desire compartment 364 are positioned over the outlet port, as indicated by step 4060.

Figure 40F:
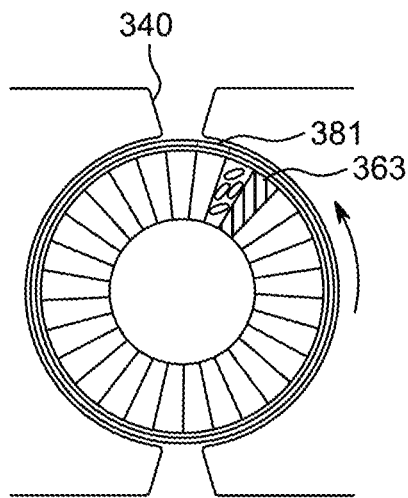
Figure 40G:
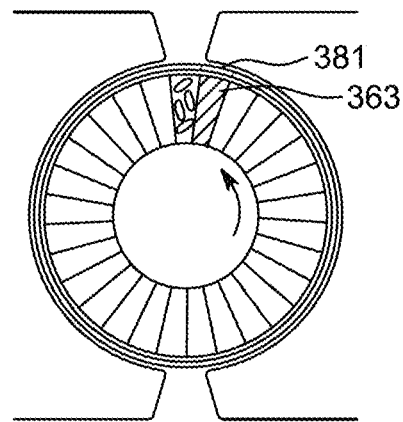
Figure 40H:
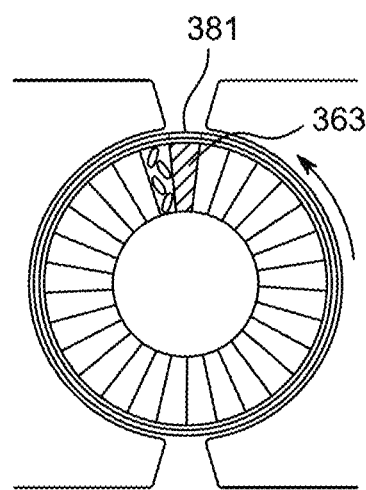

At step 4070, both ring member 380 and container member 362 are rotated back toward the closed position. As shown in FIG. 40F, the rotation is stopped just short of the closed position, with window 381 positioned next to, but not in line with inlet port 340. At step 4075, ring member 380 is decoupled from container member 362, and at step 4080, the containment member 362 is rotated independent of ring member 380 to align filled member 363 with window 381 (as shown in FIG. 40G). At step 4085, the ring member is coupled to the container member. At step 4090, both ring member 380 and container member 362 are rotated to the closed position (shown in FIG. 40H).

It should be appreciated that the steps shown in FIG. 40A are merely illustrative and that additional steps may be added, that some steps may be omitted, or the order of the steps may be rearranged.

Figure 41:
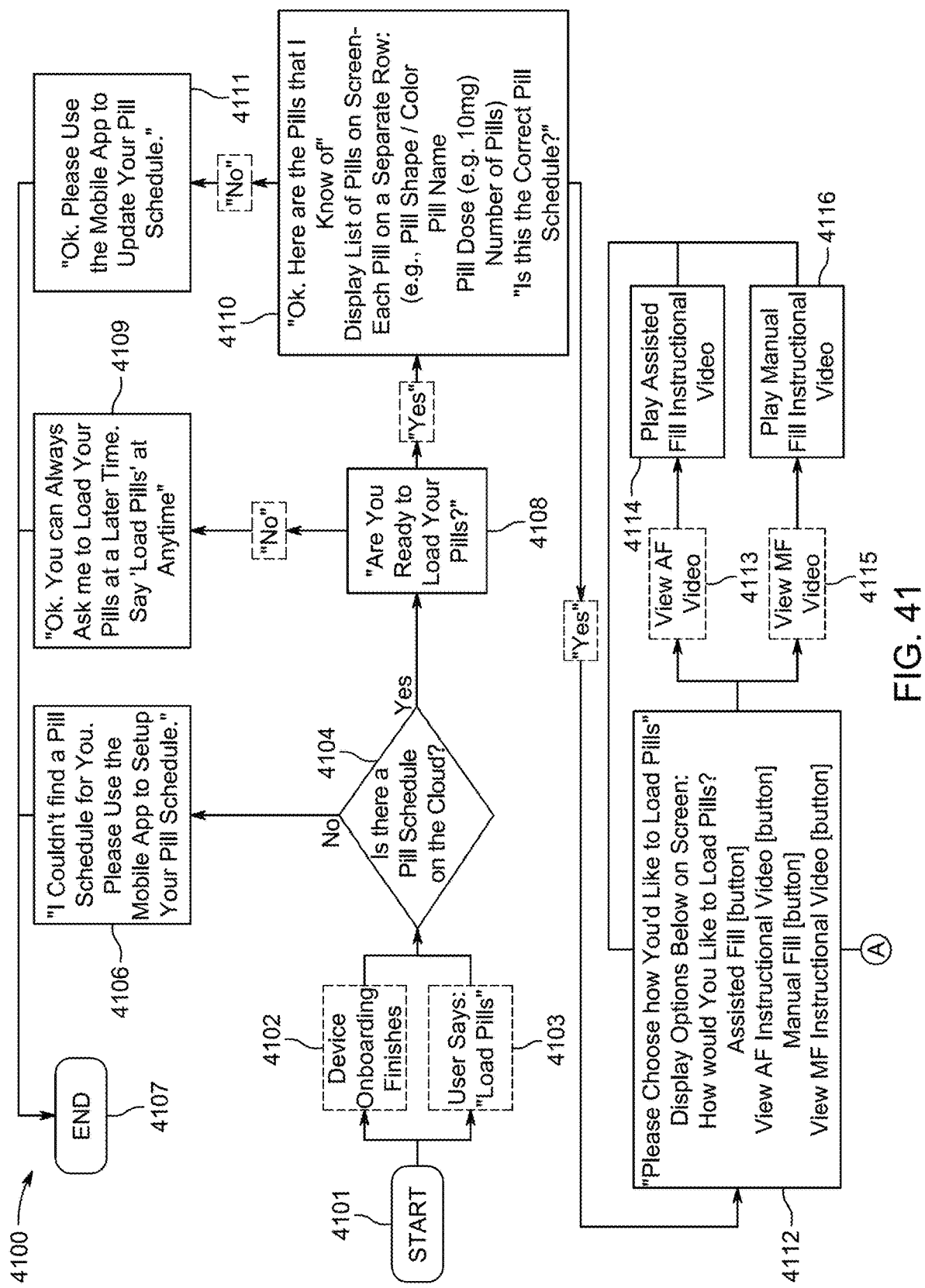
FIG. 41 shows an illustrative pill loading process according to an embodiment.
Figure 41:
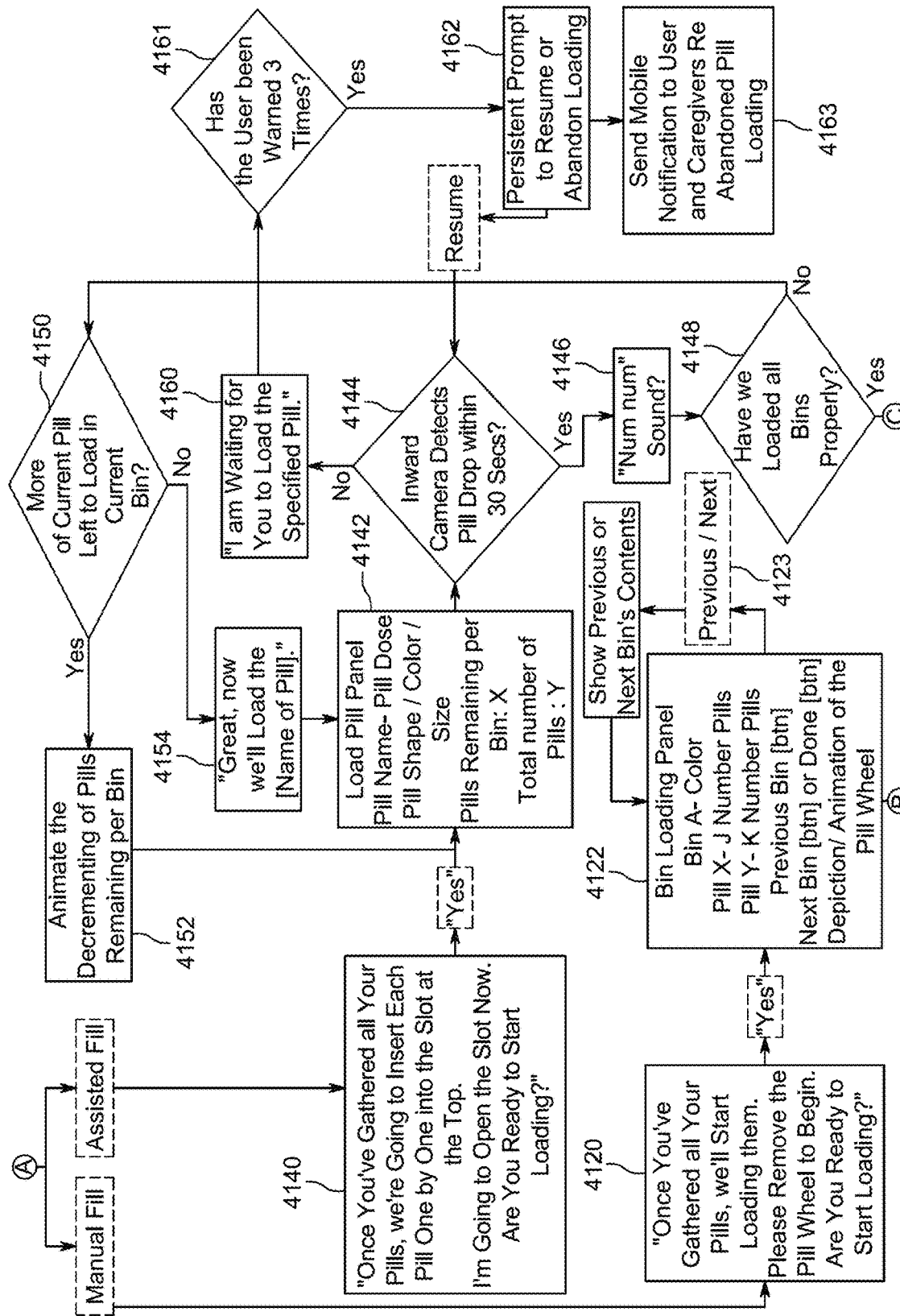
Figure 41:
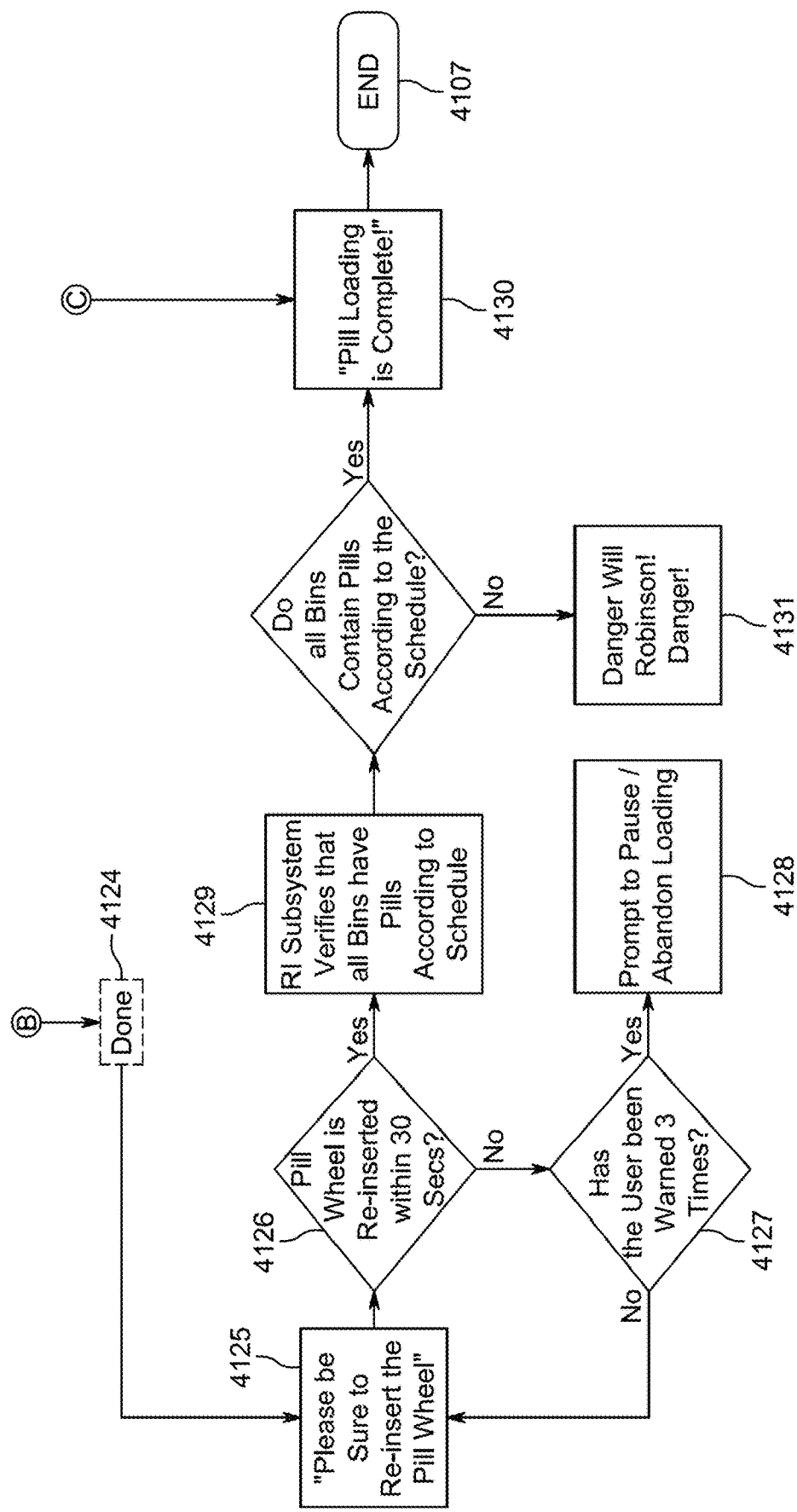

FIG. 41 shows an illustrative pill loading process 4100 according to an embodiment. Process 4100 may begin at step 4101. At step 4102, a device such as a RI subsystem may complete an initialization or setup process and is ready to perform a pill loading procedure. In some embodiments, the device may recognize user spoken commands to perform an action such as pill loading, as step 4103. At step 4104, a determination is made as to whether a pill schedule exists. The pill schedule may be located on a cloud server or locally with the RI subsystem. If no pill schedule exists, process 4100 may inform the user that no schedule exists and that one must be created before a pill loading can commence, as indicated at step 4106. Process 4100 may end at step 4107.

If a pill schedule does exist, process 4100 may ask the user whether he or she is ready to load pills at step 4108. If the user says or inputs a NO command, then process 4100 may inform the user that the pills be may loaded at another time, as indicated by step 4109. If the user says or inputs a YES command at step 4108, process 4100 may display or audibly inform the user of the pills that should be loaded at step 4110. The display may display information relating to each known pill including, for example, pill shape and color, pill name, pill dosage, and the number of pills. Process 4100 may ask the user to confirm whether the displayed pill information is correct. If the user says or inputs a NO command, process 4100 may instruct the user to update the pill schedule at step 4111. If the user says or inputs a YES command, process 4100 may proceed to step 4112.

At step 4112, process 4100 may ask the user how he or she would like to load the pills and whether the user wishes to watch a video on the different loading techniques. For example, the user can choose from an assisted fill of pills or a manual fill of pills. If the user desires to watch instructional videos for either assisted or manual filling pills, he or she can select which video(s) to watch and process 4100 may cause an assisted fill video to be played back at steps 4113 and 4114 or cause a manual fill video to be played back at steps 4115 and 4116. After the selected video is played back, process 4100 may return to step 4112.

If the user elects to manually fill pills at step 4112, process 4100 may proceed to step 4120. At step 4120, process 4120 may inform the user to gather his or her pills, remove the container assembly from the RI subsystem, and indicate when he or she is ready to start loading. In the manual fill mode, the user manually inserts the pills into the container assembly or pill box. Process 4100 may provide, at step 4122 audio and/or visual instructions of which pills and a quantity thereof are to be placed in a particular bin or compartment of the container assembly. The user may provide input instructions, at step 4123, to cause process 4100 to show what the pill composition is for the next compartment/bin or the previous compartment/bin. Process 4100 may repeat the pill loading instructions for each compartment until the container assembly is full or the user indicates he or she is done filling pills (step 4124).

After the user is done loading pills, process 4100 may instruct the user to insert the container assembly in to the RI subassembly at step 4125. At step 4126, a determination is made as to whether the container assembly is re-inserted. If desired, a time limit may be associated with the re-insertion. At step 4127, if the container assembly has not been re-inserted and the time limit has not expired or the user has been warned less than a predetermined number of times, process 4100 may look back to step 4125. If, at step 4127, the container assembly has not been re-inserted and the time limit has expired or the user has been warned at least the predetermined number of times, process 4100 may pause or abandon the pill loading procedure at step 4128.

If, at step 4126, the container assembly is re-inserted, process 4100 may verify whether all pills have been inserted in their respective compartments as instructed (at step 4129).

The RI system may use an internal camera, for example, to determine whether the pills have been properly loaded. If the pills are determined to be properly loaded, process 4100 may proceed to step 4130, in which the system may indicate that pill loading is complete, and then process 4100 may end at step 4107. If the pills are determined not be loaded properly, process 4100 may inform the user of a danger situation and may not dispense any pills (as indicated by step 4131).

If the user elects to perform an assisted fill of pills at step 4112, process 4100 may proceed to step 4140. At step 4140, process 4100 may instruct the user to gather his or her pills ask for configuration if he or she is ready to start. During assisted fill of pills, the user may fill pills into the container assembly by inserting them through the inlet port at the top of the RI subsystem. At step 4142, process 4100 may indicate (visually and/or audibly) which pills and how many of each are to be inserted into the inlet port to fill a particular one of the compartments. At step 4144, the system may verify whether a pill has been inserted into the inlet port and contained in that particular compartment. For example, a camera may track the number of pills, the color of the pills, and/or the size of the pills being inserted. If the pill was inserted, process 4100 may emit a sound (at step 4146) to indicate that the RI subsystem properly processed the pills for that compartment, and then proceed to step 4148. At step 4148, a determination is made as to whether all compartments have been loaded. If YES, process 4100 proceeds to step 4130. If NO, process 4100 may proceed to step 4150, which determines whether more of a particular pill needs to be inserted into a particular compartment. If YES, process 4100 may provide an indication (e.g., animation), at step 4152, that at least one additional pill is needed and return to step 4142. If the determination at step 4150 is NO, process 4100 may indicate that it is now time to insert another pill (at step 4154) and proceed to step 4142. Thus, in one embodiment, it should be appreciated that assisted pill loading ensures that the correct number of pills for each pill type are inserted into each compartment before moving on to the next compartment.

If at step 4144, it is not verified that a pill is inserted, process 4100 may progress through steps 4160-4163, as appropriate.

It should be appreciated that the steps shown in FIG. 41 are merely illustrative and that additional steps may be added, that some steps may be omitted, or the order of the steps may be rearranged.

Figure 42:
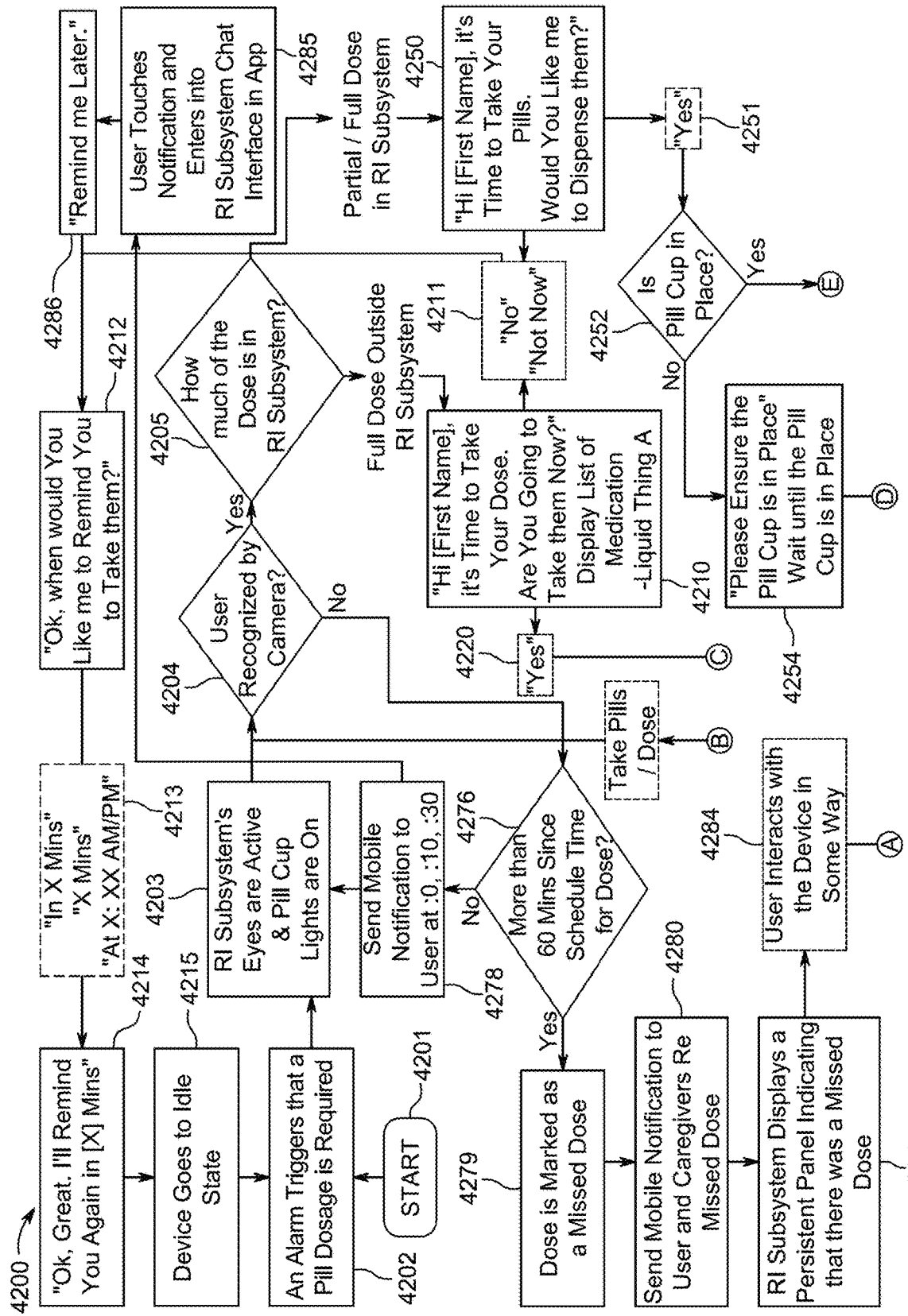
FIG. 42 shows an illustrative pill dispensing process according to an embodiment.
Figure 42:
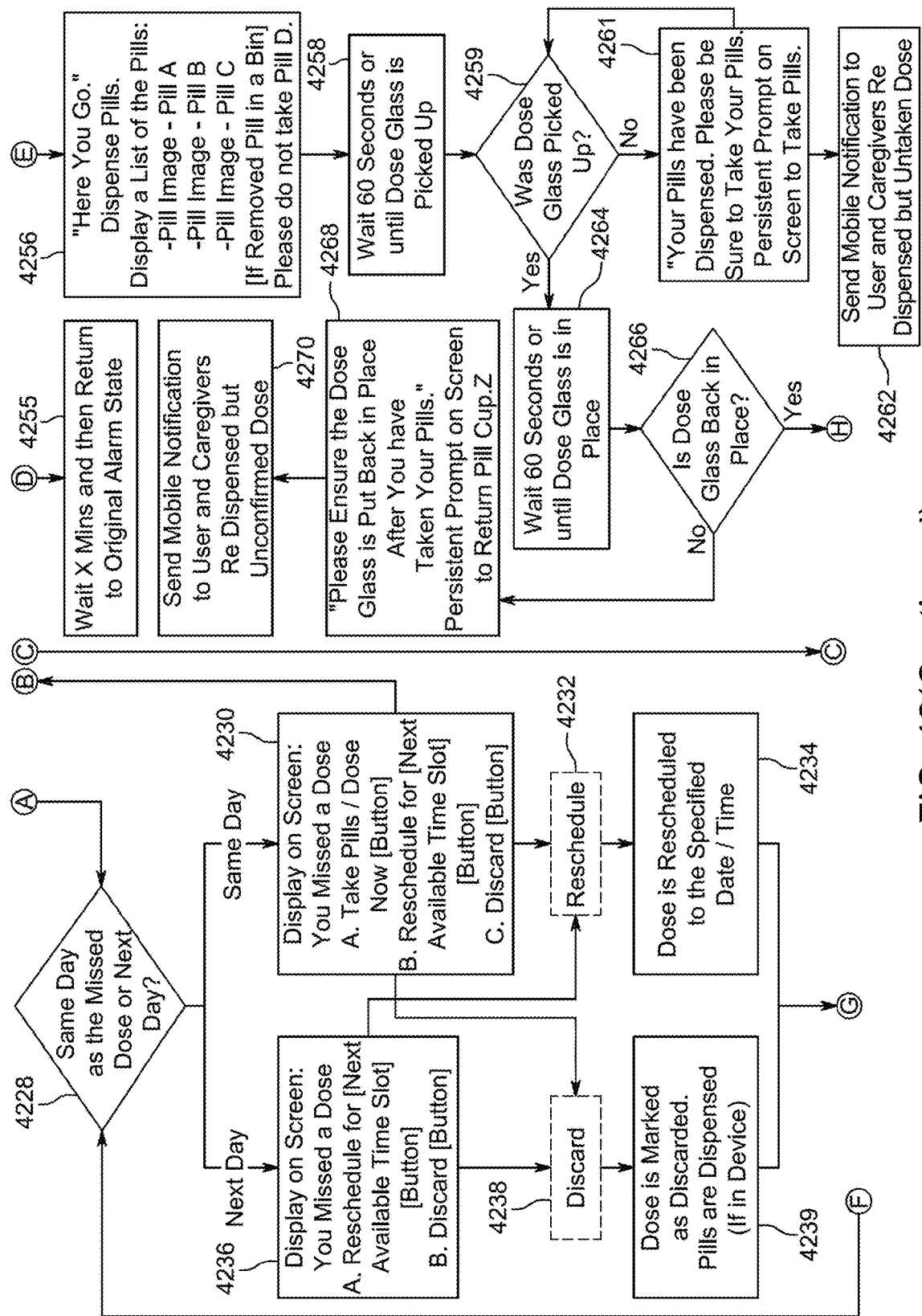
Figure 42:
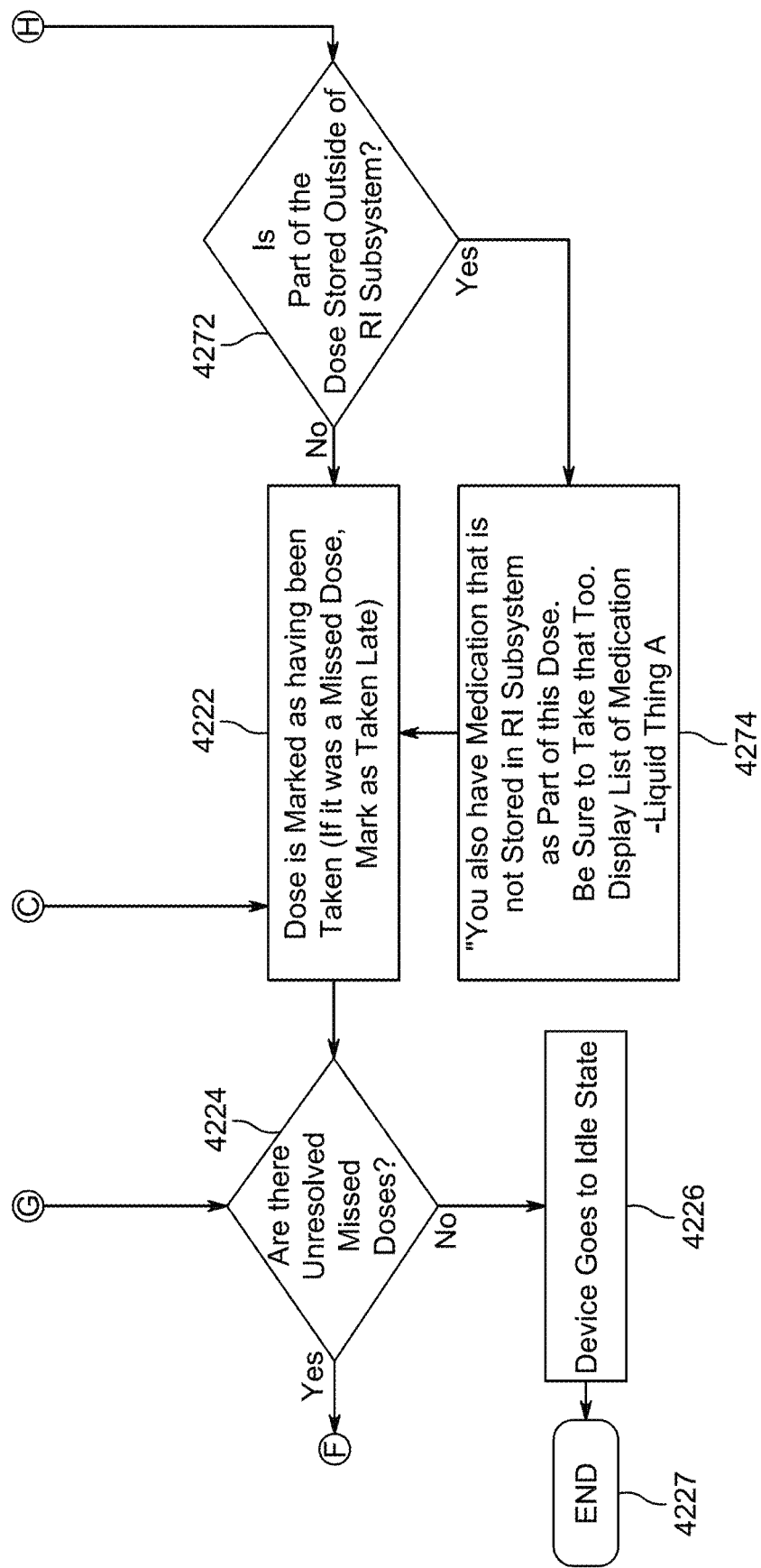

FIG. 42 shows an illustrative pill dispensing process 4200 according to an embodiment. Process 4200 may begin at step 4201. At step 4202, an alarm or wakeup signal may cause a device such as a RI subsystem turn on and commence a pilling dispensing procedure. At step 4203, in response to the wakeup signal, the device may turn on. For example, the device may light up its virtual eyes on the touchscreen and light up a dispensing area. At step 4204, the device may determine whether it recognizes the user. For example, the device may use facial recognition software to identify the image of user captured by its camera, or the user may place his or her fingerprint on a fingerprint scanner to verify the user's identity.

If the user's identity is verified at step 4204, process 4200 may proceed to step 4205, which determines whether the user's recommend medicine is contained within or outside of the device. If the user's medicine is located outside of the device, process 4200 may inform the user which medicine he should take and whether he wishes to take the medicine now or later (at step 4210). If the user opts not to take the medicine (at step 4211), process 4200 may prompt the user as to when he would like to be reminded to take it (at step 4212). The user may input his response at step 4213. The user may specify, for example, an exact time of reminder or a set oa timer defining the number of minutes or hours to be reminded. At step 4214, the device may confirm when it provide the reminder and go into an idle state at step 4215. When the timer elapses or the reminder time is reached, process 4200 may restart at step 4201.

Referring back to step 4210, if the user opts to take the medicine (at step 4220), process 4200 may mark the medicine dose as having been taken (or marked as taken late if it was missed) at step 4222. At step 4224, a determination is made as to whether there are any unresolved missed doses. If NO, process 4200 may enter into an idle state (at step 4226) and process 4200 may end at step 4227. If the determination at step 4224 is YES, process 4200 may proceed to step 4228.

At step 4228, a determination is made whether a missed dose occurred on the same day or the next day. If the missed dose occurred on the same day, process 4200 present information pertinent to missing the dose that day (at step 4230). For example, the user may be presented with the options to take the pill now, reschedule to take the pill, discard or decide not to take the pill. If, at step 4228, the missed dose occurred on the next day, process 4200 may present information pertinent to missing the dose the next day (at step 4236). For example, the user may be presented with an option to reschedule or discard the dose. If the user opts to reschedule (at step 4232), process 4200 may reschedule a specific date and time for the user to take the dose (at step 4234) and then proceed to step 4224. If the user opts to discard the dose (at step 4238), process 4200 may mark the dose as discarded (at step 4239) and then proceeds to step 4224. In some embodiments, if the pills are contained in the device, and are marked as discarded, they may be dispensed.

Returning to step 4205, if the user's medicine is located within the device, process 4200 may inform the user it is time to take his pills whether he wishes them dispensed (at step 4250). If the user opts not to take the medicine (at step 4211), process 4200 may prompt the user as to when he would like to be reminded to take it (at step 4212). If the user opts to take the medicine (at step 4251), a determination may made be as to whether a pill cup is present. If NO, the system may instruct the user to place the pill in cup in place (at step 4254) and the system may wait a fixed period of time before returning to the idle state (step 4255). If the user timely places the pill cup in place, process 4200 may proceed to step 4256). Process 4200 may proceed to step 4256 if the pill cup is determined to be in place.

At step 4256, the device may dispense all the pills the user needs to consume. In addition, the device may display of list of the pills the user should take. At step 4258, process 4200 may wait a fixed period of time (e.g., 60 seconds) or until the pill cup is picked up before proceeding to step 4259. At step 4259, a determination is made as to whether the pill cup was picked up. If the cup is not picked up, process 4200 may provide reminders by providing audio and/or visual cues (at step 4261) or sending mobile notifications to the user's or caretaker's mobile phone (at step 4262). Process 4200 may return to step 4259 from step 4261 or 4262.

At step 4264, process 4200 may wait another fixed period of time or until the pill cup is placed back in its place in the device. At step 4264, a determination is made as to whether the pill cup has been put back in place in the device. If NO, process 4200 may provide a notice informing the user to place cup back in place after the user has consumed the pill(s) (at step 4268). In addition, mobile notifications may be sent to the user's or caretaker's mobile device at step 4270. If the pill cup is replaced or in place, process 4200 may determine whether part of the dose is located outside of the device at step 4272. If the determination at step 4272 is YES, process 4200 may inform the user to take the medicine that is not stored in the device (at step 4274). In addition, the device may display a list of the medications that user should take. If the determination at step 4272 is NO, process 4200 may proceed to step 4222 (previously discussed).

If, at step 4204, the user is not recognized, process 4200 may determine whether more than a fixed period of time (e.g., sixty minutes) has elapsed since a scheduled time for a dose (at step 4276). If the determination at step 4276 is NO, process 4200 may send one or more mobile messages to the user's mobile phone (at step 4278). For example, the notifications may be sent to user's phone at different time periods within the fixed period of time. The process 4200 may proceed to step 4285, in which a user activates a rescheduling program to reschedule admission of the dosage (at step 4286). Process 4200 may continue to step 4212 (as previously discussed). If the determination at step 4276 is YES, process 4200 may mark the dose as missed (at step 4279) and send a notification to the user's or caretaker's phone to inform of the missed dose (at step 4280). At step 4280, the system may display a persistent infographic that a dose was missed. If the user interacts with the device (at step 4284), process 4200 may proceed to step 4228 (previously discussed).

It should be appreciated that the steps shown in FIG. 42 are merely illustrative and that additional steps may be added, that some steps may be omitted, or the order of the steps may be rearranged.

Further Description of FIGS. 1-42

One, some, or all of the processes described with respect to FIGS. 1-42 may each be implemented by software, but may also be implemented in hardware, firmware, or any combination of software, hardware, and firmware. Instructions for performing these processes may also be embodied as machine- or computer-readable code recorded on a machine- or computer-readable medium. In some embodiments, the computer-readable medium may be a non-transitory computer-readable medium. Examples of such a non-transitory computer-readable medium include but are not limited to a read-only memory, a random-access memory, a flash memory, a CD-ROM, a DVD, a magnetic tape, a removable memory card, and a data storage device (e.g., memory 13 and/or data structure 19 of FIG. 1 and/or memory 113 and/or data structure 119 of FIG. 1A). In other embodiments, the computer-readable medium may be a transitory computer-readable medium. In such embodiments, the transitory computer-readable medium can be distributed over network-coupled computer systems so that the computer-readable code may be stored and executed in a distributed fashion. For example, such a transitory computer-readable medium may be communicated from HMS subsystem 10 to a subsystem 100, from a subsystem 100 to HMS subsystem 10, and/or from one subsystem 100 to another subsystem 100 using any suitable communications protocol (e.g., the computer-readable medium may be communicated to a subsystem 100 via communications component 14/114 (e.g., as at least a portion of a data structure 119)). Such a transitory computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal.

It is to be understood that any, each, or at least one module or component or subsystem of the disclosure may be provided as a software construct, firmware construct, one or more hardware components, or a combination thereof. For example, any, each, or at least one module or component or subsystem of system 1 may be described in the general context of computer-executable instructions, such as program modules, that may be executed by one or more computers or other devices. Generally, a program module may include one or more routines, programs, objects, components, and/or data structures that may perform one or more particular tasks or that may implement one or more particular abstract data types. It is also to be understood that the number, configuration, functionality, and interconnection of the modules and components and subsystems of system 1 are merely illustrative, and that the number, configuration, functionality, and interconnection of existing modules, components, and/or subsystems may be modified or omitted, additional modules, components, and/or subsystems may be added, and the interconnection of certain modules, components, and/or subsystems may be altered.

The terminology used herein is for the purpose of describing particular embodiments only and is not intended to be limiting. As used herein, the term "and/or" includes any and all combinations of one or more of the associated listed items. As used herein, the singular forms "a," "an," and "the" are intended to include the plural forms as well as the singular forms, unless the context clearly indicates otherwise. It is further to be understood that the terms "comprises" and/or "comprising" specify the presence of stated features, steps, operations, elements, components, and/or components, but do not preclude the presence or addition of one or more other features, steps, operations, elements, components, and/or groups thereof.

While there have been described systems, methods, and computer-readable media for a healthcare management service, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

Therefore, those skilled in the art will appreciate that the invention can be practiced by other than the described embodiments, which are presented for purposes of illustration rather than of limitation.

What is claimed is:

1. A pill dispenser comprising:
a body,
a motor supported by the body,
an outlet port formed on the body;
a container comprising a plurality of compartments, and
a processor configured to:
    receive, from a camera, image information representing an image of a user,
    identify the user using the captured image via electronic facial recognition, and
    in response to the user being identified as an authorized user, awaken the pill dispenser from a low-power mode and perform a pill dispensing procedure, wherein the processor is configured to perform the pill dispensing procedure by:
  identifying, among the plurality of compartments, the compartment in which one or more pills are stored; and
  actuating the motor to move the container relative to the body, wherein the actuating comprises aligning the identified compartment to the outlet port.

2. The pill dispenser of claim 1, wherein the pill dispenser comprises the camera.

3. The pill dispenser of claim 1, wherein the processor is configured to identify the user via electronic facial recognition by:
  determining one or more parameters from the image information;
  comparing the determined one or more parameters to one or more reference parameters for the authorized user; and
  in response to the comparing, determining that the user is the authorized user.

4. The pill dispenser of claim 1, wherein the processor is configured to identify the user via electronic facial recognition by:
  uploading the image information to a cloud server; and
  receiving notification from the cloud server that the user is an authorized user.

5. The pill dispenser of claim 1, wherein the processor is configured to identify the compartment in which one or more pills are stored using a pill schedule associated with the user.

6. The pill dispenser of claim 1, wherein the processor is further configured to display a list of pills to be dispensed to the user on a display.

7. The pill dispenser of claim 6, wherein the pill dispenser comprises the display.

8. The pill dispenser of claim 1, wherein the processor is further configured to, after actuating the motor to move the container relative to the body, determine whether a receptacle has been removed from under the outlet port.

9. The pill dispenser of claim 1, wherein the processor is further configured to, if it is determined that the receptacle has not been removed from under the outlet port, output a notification informing the user that the receptacle has not been removed.

10. A pill dispenser comprising:
  a body;
  a pill container supported by the body;
  an outlet port formed on the body; and
  a processor configured to:
    determine that a user has entered a detectable sphere based on a signal received from a sensor,
    identify that the user is an authorized user,
    in response to both the determining and the identifying, and further in response to receiving a command from a user, awaken the pill dispenser from a low-power mode and control the container to dispense one or more pills through the outlet port.

11. The pill dispenser of claim 10, wherein the sensor is a camera.

12. The pill dispenser of claim 11, wherein the processor is configured to identify that the user is an authorized user via facial recognition.

13. The pill dispenser of claim 12, wherein the processor is configured to identify that the user is an authorized user by:
  determining one or more parameters from an image captured with the camera;
  comparing the determined one or more parameters to one or more reference parameters for the authorized user; and
  in response to the comparing, determining that the user is the authorized user.

14. The pill dispenser of claim 10, wherein the processor is configured to control the container so as to align a particular compartment of the pill container to the outlet port.

15. A pill dispenser comprising:
  a body;
  a motor supported by the body;
  an outlet port formed on the body;
  a container comprising a plurality of compartments;
  a spring loaded door;
  a removable cover positioned on a top surface of the container, the removal cover comprising a plurality of cover compartments aligning with respective compartments of the plurality of compartments;
  a mechanical rocker coupled to the body and configured to open the spring loaded door to permit insertion of pills into a compartment of the plurality of compartments; and
  a processor configured to:
    actuate the motor to move the container relative to the body to dispense a pill located in a first compartment of the plurality of compartments into a receptacle through the outlet port, wherein the actuating comprises aligning the first compartment of the plurality of compartments to the outlet port, and
    determine whether a receptacle has been removed from under the outlet port using an electromagnetic sensor.

16. The pill dispenser of claim 15, wherein the electromagnetic sensor comprises a radio frequency identification (RFID) tag or a near field communication (NFC) tag.

17. The pill dispenser of claim 15, wherein the electromagnetic sensor is disposed on the receptacle.

18. The pill dispenser of claim 15, wherein the processor is further configured to determine, using a pill schedule associated with the user, that one or more pills to be dispensed to the user are stored in the first compartment.

19. The pill dispenser of claim 15, wherein the processor is further configured display a list of pills to be dispensed to the user on a display.

* * * * *